(12) United States Patent
Martin-Villalba et al.

(10) Patent No.: US 9,309,320 B2
(45) Date of Patent: Apr. 12, 2016

(54) NEUTRALIZATION OF CD95 ACTIVITY BLOCKS INVASION OF GLIOBLASTOMA CELLS IN VIVO

(75) Inventors: Ana Martin-Villalba, Heidelberg (DE); Susanne Kleber, Heidelberg (DE); Benedikt Wiestler, Schriesheim (DE); Peter G. Krammer, Heidelberg (DE); Christel Herold-Mende, Bammental (DE); Ignacio Sancho-Martinez, Heidelberg (DE)

(73) Assignees: Deutsches Krebsforschungszentrum Stiftung Des Oeffentlichen Rechts, Heidelberg (DE); Universitaetsklinikum Heidelberg, Heidelberg (DE)

( * ) Notice: Subject to any disclaimer, the term of this patent is extended or adjusted under 35 U.S.C. 154(b) by 527 days.

(21) Appl. No.: 12/521,625

(22) PCT Filed: Dec. 28, 2007

(86) PCT No.: PCT/EP2007/011461
§ 371 (c)(1),
(2), (4) Date: Sep. 9, 2009

(87) PCT Pub. No.: WO2008/080623
PCT Pub. Date: Jul. 10, 2008

(65) Prior Publication Data
US 2010/0322922 A1 Dec. 23, 2010

Related U.S. Application Data

(60) Provisional application No. 60/877,367, filed on Dec. 28, 2006.

(51) Int. Cl.
| A61K 39/00 | (2006.01) |
| A61K 38/00 | (2006.01) |
| C07K 16/28 | (2006.01) |
| C07K 14/705 | (2006.01) |
| G01N 33/566 | (2006.01) |
| G01N 33/574 | (2006.01) |

(52) U.S. Cl.
CPC .......... *C07K 16/2875* (2013.01); *A61K 38/00* (2013.01); *C07K 14/70575* (2013.01); *C07K 14/70578* (2013.01); *G01N 33/566* (2013.01); *G01N 33/57407* (2013.01); *A61K 2039/505* (2013.01); *C07K 16/2878* (2013.01); *C07K 2317/76* (2013.01); *C07K 2319/00* (2013.01); *C07K 2319/30* (2013.01); *G01N 2500/00* (2013.01)

(58) Field of Classification Search
None
See application file for complete search history.

(56) References Cited

U.S. PATENT DOCUMENTS

| 6,060,238 A | 5/2000 | Dixit | |
| 7,445,794 B1* | 11/2008 | Newell et al. | 424/450 |
| 8,007,813 B2* | 8/2011 | Walczak | 424/192.1 |
| 2003/0170244 A1* | 9/2003 | Pluenneke et al. | 424/146.1 |
| 2004/0024050 A1* | 2/2004 | Smith et al. | 514/449 |

FOREIGN PATENT DOCUMENTS

| WO | 9629350 A1 | 9/1996 |
| WO | 99/55134 A | 11/1999 |
| WO | 2004/085478 A | 10/2004 |

OTHER PUBLICATIONS

Choi et al., Neuroscience Letters, 2003, 352:21-24.*
Kleber, XP002483066, Jan. 3, 2006.*
O'Reilly et al., "Membrane-bound but not Secreted Fas Ligand is Essential for Fas-Induced Apoptosis and Prevention of Autoimmunity and Cancer", Nature, Oct. 1, 2009; 461 (7264): 659-663.
Chen et al., "CD95 promotes tumour growth", Nature, vol. 465, May 27, 2010, pp. 492-496.
Green, "A wolf in wolf's clothing", Nature, vol. 465, May 27, 2010, pp. 433-434.
Apogenix: Death Receptor CD95 Promotes Tumour Growth, pp. 1-2, May 27, 2010.
Kleber, "Gamma-Bestrahlung fuehrt zur CD95-abhaengiger Invasivitaet in apoptoseresistenten Glioblastomzellen", Jan. 3, 2006, abstract only.
Barnhart et al, "CD95 ligand induces motility and invasiveness of apoptosis-resistant tumor cells", The EMBO Journal, Aug. 4, 2004, vol. 23, No. 15, pp. 3175-3185.
BD Biosiences Produce Catalog Pharmingen 2003, p. 363.
Hauptschein et al, "Functional proteomic screen indentifies a modulating role for CD44 in death receptor-mediated apoptosis", Cancer Research, Mar. 1, 2005, vol. 65, No. 5, pp. 1887-1896.
Weller et al., "Anti-Fas/APO-1 antibody-mediated apoptosis of cultured human glioma cells. Induction and modulation of sensitivity by cytokines", The Journal of Clinical Investigation, vol. 94, No. 3, Sep. 1994, pp. 954-964.
European Search Report dated Feb. 13, 2012 in corresponding application No. 11190918.0. 9 pgs.
Strege et al., "Protein expression of Fas, Fas ligand, Bcl-2 and TGFβ2 and correlation with survival in initial and recurrent human gliomas", Journal of Neuro-Oncology, 67, 2004, pp. 29-39.

(Continued)

*Primary Examiner* — Hong Sang
(74) *Attorney, Agent, or Firm* — Perkins Coie LLP; Viola T. Kung

(57) ABSTRACT

The present invention relates to methods for treating an individual with high grade glioblastoma multiforme by preventing or disrupting the binding of CD95 to its ligand, CD95L, in vivo, whereupon that neutralization of CD95 activity reduces undesirable glial cell migration and invasion into body tissue.

6 Claims, 55 Drawing Sheets

(56) References Cited

OTHER PUBLICATIONS

Translation of Japanese Office Action in parallel application No. JP 2009 543 400 dated Mar. 18, 2013, 13 pgs.
Information sheet of the NOK 1® product of Santa Cruz Biotechnology (2 pg) Sep. 8, 2011.
Information sheet of BioLegend, Purified Anti-human CD178 Fas-L Antibody, (2 pgs), Sep. 8, 2011.
Information sheet of abcam, Fas Ligand antibody [NOK-1] (Phycoerythrin)(ab93575), Sep. 8, 2011.
Louis et al., The 2007 WHO Classification of Tumours of the Central Nervous System, Acta Neuropathol (2007) 114:97-109.
Tran et al., Inhibiting TGF-B signaling restores immune surveillance in the SMA-560 glioma model, Neuro-Oncology, Jul. 2007, pp. 259-270.
Legembre et al., "The relevance of NF-KB for CD95 signaling in tumor cells", Cell Cycle 2004, vol. 3, No. 10, pp. 1235-1239, e-87-91.
Legembre et al., "Identification of SNF1/AMP kinase-related kinase as an NF-kB-regulated anti-apoptotic kinase involved in CD95-induced motility and invasiveness", J. Biol. Chem., 2004, vol. 279, No. 45, pp. 46742-46747.

* cited by examiner a T98G b LN18

Fig. 19 A
Fig. 19 B
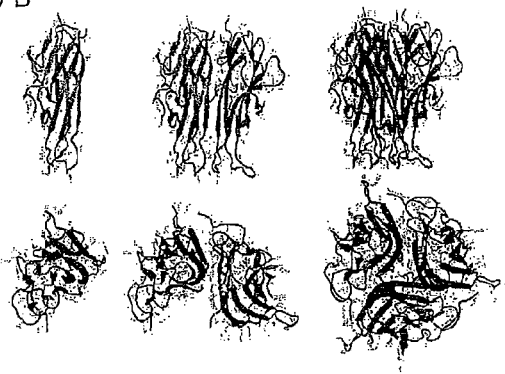
Fig. 19 C
1   METDTLLLWVLLLWVPGSTGELRKVAHLTGKSNSRSMPLEWEDTYGTVLLSGVKYKKGGL
61  VINETGLYFVYSKVYFRGQSCNNLPLSHKVYMRNSKYPQDLVMMEGKNMSYCTTGQMWAR
121 SSYLGAVFNLTSADHLYVNVSELSLVNFEESQTFFGLYKLGSSGSSGSSGSGYIPEAPRD
181 GQAYVRKDGEWVLLSTFLSGPSSSSSHHHHHHSAWSHPQFEK
Fig. 19 D
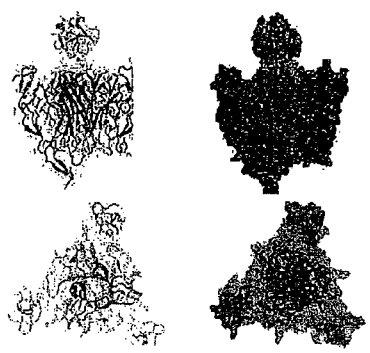

TABLE 1. Summary of clinical data from tumor patients.

| No. | Sex | Age at surgery (y) | Diagnosis | Survival time (weeks) |
|---|---|---|---|---|
| NCH37 | male | 52 | Gliosarcoma WHO IV | 40 |
| NCH82 | male | 56 | GBM | 16 |
| NCH89 | female | 41 | GBM | 29 |
| NCH125 | male | 43 | GBM | 57 |
| NCH149 | male | 54 | GBM | 71 |
| NCH156 | male | 54 | GBM | 69 |
| NCH160 | male | 58 | GBM | 54 |
| NCH199 | male | 38 | secondary GBM | 28 |
| NCH270 | male | 72 | GBM | 32 |
| NCH277 | female | 78 | GBM | 173 |
| NCH316 | female | 72 | GBM | 94 |
| NCH323 | male | 25 | Astrocytoma WHO II | alive |
| NCH325 | male | 31 | GBM | alive |
| NCH342 | male | 44 | GBM | 80 |
| NCH351 | male | 37 | GBM | 60 |
| NCH354 | female | 38 | GBM | 96 |
| NCH356 | male | 67 | GBM | 86 |
| NCH357 | male | 29 | GBM | 64 |
| NCH378 | female | 71 | GBM | 40 |
| NCH408 | male | 35 | Oligodendroglioma WHO III | alive |
| NCH417 | male | 69 | GBM | - |
| NCH419 | female | 61 | WHOIII-IV | alive |

| No. | Tumor detection | Diagnosis | Time post-irradiation (w) | Age at surgery (y) | Post-recidive Survival time (w) |
|---|---|---|---|---|---|
| 19 | original | GBM | | | |
| 408 | recurrent | | 20 | 51 | 38 |
| 115 | original | GBM | | | |
| 655 | recurrent | | 20 | 56 | 56 |
| 253 | original | GBM | | | |
| 90717 | recurrent | | 2 | 56 | 91 |
| 724 | original | GBM | | | |
| 202 | recurrent | | 4 | 56 | 25 |
| 554 | original | GBM | | | |
| 910 | recurrent | | 15 | 59 | 71 |
| 251 | original | GBM | | | |
| 30 | recurrent | | 29 | 66 | 58 |
| 746 | original | GBM | | | |
| 388 | recurrent | | 32 | 54 | 69 |
| 809 | original | GBM | | | |
| 715 | recurrent | | 35 | 64 | 53 |
| 259 | original | GBM | | | |
| 860 | recurrent | | 17 | 60 | 64 |

NEUTRALIZATION OF CD95 ACTIVITY BLOCKS INVASION OF GLIOBLASTOMA CELLS IN VIVO

CROSS REFERENCE TO RELATED APPLICATION

This application is a 35 U.S.C. 371 National Phase Entry Application from PCT/EP2007/011461, filed Dec. 28, 2007, which claims the benefit of U.S. Provisional 60/877,367 filed on Dec. 28, 2008, the disclosure of which is incorporated herein in its entirety by reference.

FIELD OF THE INVENTION

The present invention relates to methods for treating an individual with high grade glioblastoma multiforme by preventing or disrupting the binding of CD95 to its ligand, CD95L, in vivo, whereupon neutralization of CD95 activity dramatically reduces the migration of cells invading the contralateral hemisphere.

BACKGROUND

Invasion of surrounding brain tissue by isolated tumor cells represents one of the main obstacles to an effective therapy of glioblastoma multiforme (GBM). Gliomas encompass the majority of tumors originating in the central nervous system (CNS). In adults, the most common tumors are high-grade neoplasms derived from astrocytes or oligodendrocytes. The World Health Organization classifies these malignant tumors according to their degree of anaplasia into grade II (diffuse astrocytoma), grade III (anaplastic astrocytoma) and grade IV (GBM)[1].

Gliomas account for more than 50% of all brain tumors and are by far the most common primary brain tumors in adults. Despite, development of new diagnostic technologies, the survival rate is extremely low. Only 3% are still alive five years after diagnosis. The clinical outcome of malignant gliomas depends on the invasion of isolated tumor cells in the nomal brain tissue. Migrating cells can escape the surgical ablation of the tumor and are then the prime targets of post-surgical radiotherapy and adjuvant chemotherapy. Chemotherapeutic agents and irradiation act primarily by inducing apoptosis. This induction of apoptosis often involves activation of the CD95 (Apo-1/Fas) death receptor/ligand system. Nevertheless, most malignant glioma cells are resistant to CD95-induced apoptosis. Here we show that triggering of CD95 increases migration/invasion in apoptosis-resistant human long-term and primary glioma cultures. That is, triggering CD95 may entail initiating CD95 activity by using an agonistic antibody to CD95 or recombinant CD95L.

The tendency of primary glioma tumors of migration over apoptosis increases with the degree of malignancy. CD95 mediates migration via the PI3K/ILK/GSK3-beta;/MMP pathway in a caspase-independent manner. Furthermore we tried to figure out the linker molecule downstream of CD95. A possible candidate was Phosphoprotein enriched in Diabetes/Phosphoprotein enriched in Astrocytes-15-kDalton" (PED/PEA-15). Knockdown experiments excluded PED/PEA-15 as linker molecule in the signaling pathway of migration mediated through CD95/CD95L-System. Most importantly, gamma-irradiation also increased migration of cells resistant to CD95-induced death. Irradiation-mediated migration could be blocked by neutralization of CD95L. Thus, a tumor's reaction to CD95 stimulation should dictate subsequent therapy options. See Kleber, S., "Gamma irradiation leads to CD95 dependent invasion in apoptosis resistant glioblastoma cells," Ph.D. Thesis, Deutsches Krebsforschungszentrum, University of Heidelberg, Jan. 3, 2006 (urn: nbn:de:bsz:16-opus-59926, which is incorporated herein by reference in its entirety.

The main types of gliomas are ependymomas, astrocytomas, and oligodendrogliomas, although there also exist mixed cellular forms of glioma cell conditions, such as oligoastrocytomas.

In addition to a cellular characterization, gliomal tumors are also characterized according to pathology and the seriousness of cellular invasion, which is typically recognized by those in the field as a "grading" classification system.

The most commonly used grading system is the World Health Organization (WHO) grading system for astrocytomas. The WHO system assigns astrocytomas a grade from I to IV, with I being the least aggressive and IV being the most aggressive. Thus, pilocytic astrocytoma is an example of a WHO Grade I glioma; diffuse astrocytoma is an example of WHO Grade II; anaplastic (malignant) astrocytoma is an example of WHO Grade III; and glioblastoma multiforme is an example of WHO Grade IV. The latter is the most common glioma in adults and, unfortunately, has the worst prognosis for inflicted patients.

Generically, the "low grade" gliomas are typically well-differentiated, slower growing, biologically less aggressive, and portend a better prognosis for the patient; while the "high grade" gliomas, are undifferentiated or anaplastic, fast growing and can invade adjacent tissues, and carry a worse prognosis. High grade gliomas are highly vascular tumors and have a tendency to infiltrate tissues, create necrosis and hypoxia, and destroy the blood-brain barrier where the tumor is located.

There also are infratentorial gliomas, which occur mostly in children and supratentorial in adults. The infratentorial gliomas are located in all interior cerebral areas below the undersurface of the temporal and occipital lobes, extending to the upper cervical cord, and includes the cerebellum. The supratentorial region is located above the tentorium cerebelli and contains the forebrain.

Tumor grade is an important prognostic factor: median survival for grade III astrocytomas is 3 to 4 years and for grade IV astrocytomas 10 to 12 months. The most frequent glioma (65%) is the GBM[1]. Cellular resistance to multiple proapoptotic stimuli and invasion of migrating tumor cells into the normal surrounding brain tissue are the main obstacles to an effective therapy.

The current treatment of malignant gliomas (grade III and IV) involves surgery, followed by irradiation and chemotherapy. Chemotherapeutic agents and γ-irradiation act primarily by inducing apoptosis. Induction of apoptosis often involves activation of the CD95/CD95-ligand (CD95L; Apo1 L/FasL) death system[2,3]. Binding of trimerized CD95L by the CD95 receptor leads to recruitment of the adapter protein FADD (Fas-associated death domain, MORT1)[4] and caspase-8 and -10 into a death-inducing signaling complex (DISC)[5]. FADD contains a death domain (DD) and a death-effector domain (DED). Via its DD, FADD binds to the DD of CD95[6]. The DED recruits the DED-containing procaspase-8 into the DISC[7]. Procaspase-8 at the DISC is activated through self-cleavage and commits the cell to apoptosis by activation of downstream effector caspases[8].

The CD95/CD95L system is used by malignant glioma cells to increase their invasion capacity. CD95 induces cell invasion via the PI3K/ILK/GSK3β pathway and subsequent expression of metalloproteinases. Increased CD95L expression is exhibited by irradiated glioma cells that escape surgical ablation. Irradiation-induced CD95 activity increased glioma cell migration. In a murine syngenic model of intracranial GBM, CD95/CD95L expression was strikingly upregulated upon interaction with the surrounding brain stroma.

The degree of CD95 and CD95L expression positively correlates with the tumor grade. Here we show that triggering of CD95 caused apoptosis in less malignant tumors (WHO I-II) while the grade IV tumors were resistant to CD95-induced apoptosis. In these highly malignant cells, CD95 mediates migration/invasion. Binding of CD95 by the CD95L activates PI3K and ILK, thereby leading to inhibition of GSK3β and to the induction of metalloproteinases. Irradiation of apoptosis-resistant cells increased expression of CD95 and CD95L, which in turn increased metalloproteinase expression and subsequently, migration/invasion. In a syngenic mouse model of intracranial gliomas, CD95 and CD95L expression was upregulated upon interaction with the surrounding stroma. Neutralization of CD95 activity dramatically reduced the number of cells invading the contralateral hemisphere.

SUMMARY

The present invention provides a method for treating an individual with high grade glioma, comprising administering an agent that neutralizes CD95 activity to an individual with high grade glioma.

In one embodiment, the agent that neutralizes CD95 activity is a compound that prevents CD95 from binding to CD95L or disrupts a CD95/CD95L complex.

In one embodiment the compound binds to CD95 or binds to CD95L or binds to the CD95/CD95L complex.

In another embodiment, the compound is an antibody that binds to CD95. In another embodiment, the compound is an antibody that binds to CD95L. The antibodies according to the invention may be monoclonal, polyclonal or chimeric. However, also single chain antibodies or functional antibody fragments ma be used. In one embodiment, the antibody that binds to CD95 is Nok1. Thus, the present invention contemplates any neutralization agent or "inhibitor" of CD95 or CD95L or CD95R (the CD95 receptor) activity.

For the production of antibodies according to the invention, various hosts including goats, rabbits, rats, mice, humans, and others, may be immunized by injection with the protein or any fragment or oligopeptide thereof which has immunogenic properties. Depending on the host species, various adjuvants may be used to increase immunological response. It is preferred that the peptides, fragments or oligopeptides used to induce antibodies to the protein have an amino acid sequence consisting of at least five amino acids, and more preferably at least 10 amino acids. Monoclonal antibodies to the proteins may be prepared using any technique that provides for the production of antibody molecules by continuous cell lines in culture. These include, but are not limited to, the hybridoma technique, the human B-cell hybridoma technique. In addition, techniques developed for the production of 'chimeric antibodies', the splicing of mouse antibody genes to human antibody genes to obtain a molecule with appropriate antigen specificity and biological activity can be used. The antibodies may be used with or without modification, and may be labeled by joining them, either covalently or non-covalently, with, for example, a reporter molecule.

Various immunoassays may be used for screening to identify antibodies having the desired specificity. Numerous protocols for competitive binding and immunoradiometric assays using either polyclonal or monoclonal antibodies with established specificities are well known in the art. Such immunoassays typically involve the measurement of complex formation between the protein, ie. CD95 and its specific antibody. A two-site, monoclonal-based immunoassay utilizing monoclonal antibodies reactive to two non-interfering protein epitopes are preferred, but a competitive binding assay may also be employed.

One inhibitor may be a CD95-ligand (Fas ligand; APO1 ligand) inhibitor. For example, CD95-ligand inhibitors may be selected from (a) an inhibitory anti-CD95 ligand-antibody or a fragment thereof; (b) a soluble CD95 receptor molecule or a CD95 ligand-binding portion thereof; and (c) a Fas ligand inhibitor selected from FLINT, DcR3 or fragments thereof.

Also contemplated are inhibitory anti-CD95L-antibodies and antigen-binding fragments thereof and soluble CD95R molecules or CD95L-binding portions thereof. Examples of suitable inhibitory anti-CD95L antibodies are disclosed in EP-A-0 842 948, WO 96/29350, and WO 95/13293 as well as chimeric or humanized antibodies obtained therefrom, cf. e.g. WO 98/10070, all of which are incorporated herein by reference. Further preferred are soluble CD95 receptor molecules, e.g. a soluble CD95 receptor molecule without transmembrane domain as described in EP-A-0 595 659 and EP-A-0 965 637 or CD95R peptides as described in WO 99/65935, all of which are herein incorporated by reference.

In one embodiment, a CD95L inhibitor which comprises an extracellular domain of the CD95R molecule, such as amino acids 1 to 172 (MLG . . . SRS) of the mature CD95 sequence according to U.S. Pat. No. 5,891,434, which is incorporated herein by reference, which may be fused to a heterologous polypeptide domain, particularly a Fc immunoglobulin molecule including the hinge region e.g. from the human IgG1 molecule. One fusion protein comprises an extracellular CD95 domain and a human Fc domain is described in WO 95/27735, which is herein incorporated by reference. Thus, according to a preferred embodiment, the agent which binds to CD95L is a fusion protein comprising an extracellular CD95 domain and a human Fc domain. According to an especially preferred embodiment, the agent that binds to CD95L is APG101 (CD95-FC, SEQ ID NO:1). APG101 comprises the domains CD95R-ECD (amino acids 17-172; ECD extracellular domain) and IgG1-Fc (amino acids 173-400).

APG101 and derivatives thereof are disclosed in WO95/27735 and WO2004/085478 which herein incorporated by reference.

The Fas ligand inhibitor FLINT or DcR3 or a fragment, e.g. soluble fragment thereof, for example the extracellular domain optionally fused to a heterologous polypeptide, particularly a Fc immunoglobulin molecule is described in WO 99/14330 or WO 99/50413 which are herein incorporated by reference. FLINT and DcR3 are proteins which are capable of binding the CD95 ligand.

In a further embodiment of the present invention, the inhibitor is a CD95R inhibitor which may be selected from (a) an inhibitory anti-CD95 receptor-antibody or a fragment thereof; and (b) an inhibitory CD95 ligand fragment. A fragment of an inhibitory anti-CD95 receptor antibody according to the in invention preferably presents the same epitope binding site as the corresponding antibody does. In another embodiment of the invention a fragment of an inhibitory anti-CD95 receptor antibody has substantially the same CD95R inhibiting activity as the corresponding antibody. An inhibitory CD95 ligand fragment preferably presents substantially the same inhibiting activity as the corresponding inhibitory CD95 ligand fragment does.

Examples of suitable inhibitory anti-CD95R-antibodies and inhibitory CD95L fragments are described in EP-A-0 842 948 and EP-A-0 862 919 which are herein incorporated by reference.

In still a further embodiment of the present invention the inhibitor is a nucleic acid effector molecule. The nucleic acid effector molecule may be DNA; RNA, PNA or an DNA-RNA-hybrid. It may be single stranded or double stranded. Expression vectors derived from retroviruses, adenovirus, herpes or vaccina viruses or from various bacterial plasmids may be used for delivery of nucleotide sequences to the targeted organ, tissue or cell population. Such constructs may be used to introduce untranslatable sense or antisense sequences into a cell. Even in the absence of integration into the DNA, such vectors may continue to transcribe RNA molecules until they are disabled by endogenous nucleases. Transient expression may last for a month or more with a non-replicating vector and even longer if appropriate replication elements are part of the vector system.

The nucleic acid effector molecule may be in particular selected from antisense molecules, RNAi molecules and ribozymes which are capable of inhibiting the expression of the CD95R and/or CD95L gene. See, for instance, U.S. 20060234968, which is incorporated herein by reference. In another embodiment, the high grade glioma is a WHO Grade III or IV glioma. In a preferred embodiment, the high grade glioma is a WHO Grade IV glioma.

According to an especially preferred embodiment of the invention the agent neutralizing CD95 activity prevents an interaction between CD95 and the protein p85 of PI3K.

According to the present invention CD95 activity can be determined by the person skilled in the by any kind of suitable assay, such as outlined in Example 25 or Example 26.

The present invention also provides a pharmaceutical composition, comprising at least one agent that neutralizes CD95 activity to an individual with high grade glioma. In one embodiment, the agent is Nok1 or CD95-FC (APG101). CD95-FC binds to CD95L and thereby prevents its binding to CD95.

In another embodiment, the pharmaceutical composition comprises at least one agent that binds CD95 and at least one other agent that binds to CD95L. The present invention also provides a method for treating a patient with glioma by administering one of the pharmaceutical compositions contemplated herein. In one embodiment, the glioma is a Grade III or Grade IV WHO-classified glioma, or a "high grade" glioma.

In another preferred embodiment the pharmaceutical composition may comprise further active agents for the treatment of cancer and in particular for the treatment of high grade glioma.

The pharmaceutical compositions compositions may be administered alone or in combination with at least one other agent, such as stabilizing compound, which may be administered in any sterile, biocompatible pharmaceutical carrier, including, but not limited to, saline, buffered saline, dextrose, and water. The compositions may be administered to a patient alone or in combination with other agents, drugs or hormones. The pharmaceutical compositions utilized in this invention may be administered by any number of routes including, but not limited to, oral, intravenous, intramuscular, intra-arterial, intramedullary, intrathecal, intraventricular, transdermal, subcutaneous, intraperitoneal, intranasal, enteral, topical, sublingual or rectal means.

In addition to the active ingredients, these pharmaceutical compositions may contain suitable pharmaceutically-acceptable carriers comprising excipients and auxiliaries, which facilitate processing of the active compounds into preparations, which can be used pharmaceutically. Further details on techniques for formulation and administration may be found in the latest edition of Remington's Pharmaceutical Sciences (Maack Publishing Co., Easton, Pa.).

Pharmaceutical compositions suitable for use in the invention include compositions wherein the active ingredients are contained in an effective amount to achieve the intended purpose. The determination of an effective dose is well within the capability of those skilled in the art. For any compounds, the therapeutically effective dose can be estimated initially either in cell culture assays, e.g., of preadipocyte cell lines or in animal models, usually mice, rabbits, dogs or pigs. The animal model may also be used to determine the appropriate concentration range and route of administration. Such information can then be used to determine useful doses and routes for administration in humans. A therapeutically effective dose refers to that amount of active ingredient, for example a nucleic acid or a protein of the invention or an antibody, which is sufficient for treating a specific condition. Therapeutic efficacy and toxicity may be determined by standard pharmaceutical procedures in cell cultures or experimental animals, e.g., ED50 (the dose therapeutically effective in 50% of the population) and LD50 (the dose lethal to 50% of the population). The dose ratio between therapeutic and toxic effects is the therapeutic index, and it can be expressed as the ratio, LD50/ED50. Pharmaceutical compositions, which exhibit large therapeutic indices, are preferred. The data obtained from cell culture assays and animal studies is used in formulating a range of dosage for human use. The dosage contained in such compositions is preferably within a range of circulating concentrations that include the ED50 with little or no toxicity. The dosage varies within this range depending upon the dosage from employed, sensitivity of the patient, and the route of administration. The exact dosage will be determined by the practitioner, in light of factors related to the subject that requires treatment. Dosage and administration are adjusted to provide sufficient levels of the active moiety or to maintain the desired effect. Factors, which may be taken into account, include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week or once every two weeks depending on half-life and clearance rate of the particular formulation. Normal dosage amounts may vary from 0.1 to 100,000 micrograms, up to a total dose of about 1 g, depending upon the route of administration. Guidance as to particular dosages and methods of delivery is provided in the literature and generally available to practitioners in the art. Those skilled in the art employ different formulations for nucleotides than for proteins or their inhibitors. Similarly, delivery of polynucleotides or polypeptides will be specific to particular cells, conditions, locations, etc.

Another aspect of the present invention relates to a method for screening for an agent, which modulates/effects, preferably neutralizes the activity of CD95, comprising the steps
    (a) incubating a mixture comprising
        (i) CD95 or a functional fragment thereof
        (ii) a candidate agent
    under conditions whereby CD95 or a functional fragment thereof has a reference activity;
    (b) detecting the activity of CD95 or a functional fragment thereof to determine an activity in the presence of the agent;

(c) determining a difference between the activity in the presence of the agent and the reference activity.

According to a preferred embodiment of such an assay, an agent to be screened for disrupts the interaction between CD95 and PI3K, preferably between CD95 and the p85 subunit of PI3K.

(a) The glioblastoma cell lines A172, T98G and LN18 were incubated with the indicated doses of LZ-CD95L (ng/ml), Staurosporin (1 µM), or left untreated (Co). After 24 h and 48 h DNA fragmentation was analyzed by FACS. (b) FACS analysis of CD95 surface expression in the A172, T98G and LN18. (c) Spheroid cultures were embedded into a collagen matrix and treated with LZ-CD95L (5 ng/ml). Invasion of single cells into the matrix was observed with a time-lapse microscope over 24 h. The distance of invading cells (n=10 per spheroid; 3 spheroids per treatment) to the border of the spheroid was depicted in the graph mean±S.E., *P<0.05. (d) Representative phase-contrast pictures of T98G and LN18 spheroids at 0 h and 24 h after treatment. Results are representative of three independent experiments.

Figure 2:
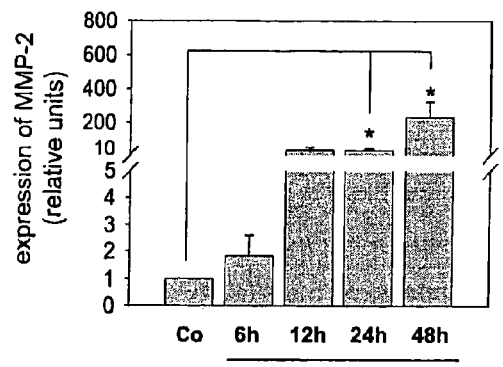
Figure 2:
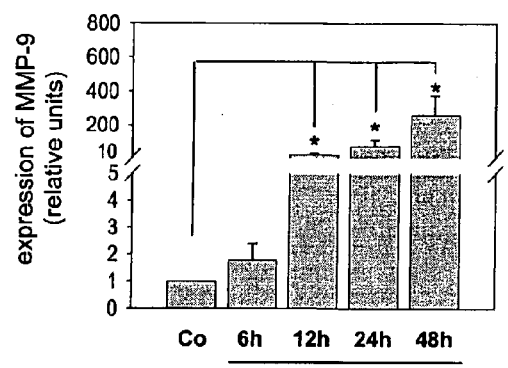
Figure 2:
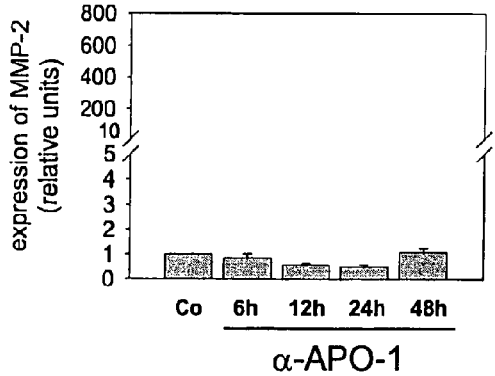
Figure 2:
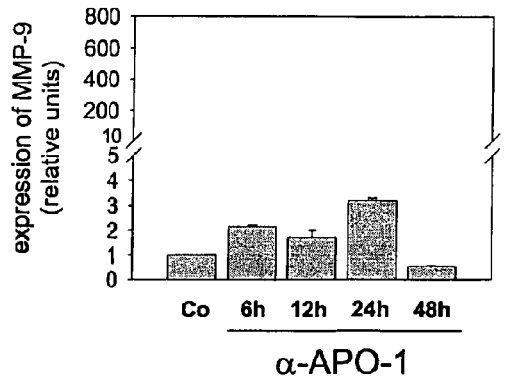

FIG. 2: Cells resistant to CD95-induced death upregulate MMP-2 and MMP-9.

T98G (FIG. 2(a)) and LN18 (FIG. 2(b)) cells were treated with α-Apo-1 (1 µg/ml) for the indicated times. Expression of MMP-2 and MMP9 was measured by quantitative real-time PCR. Data are results from five independent experiments as mean±S.E., *P<0.05, **P<0.01."

Figure 3:
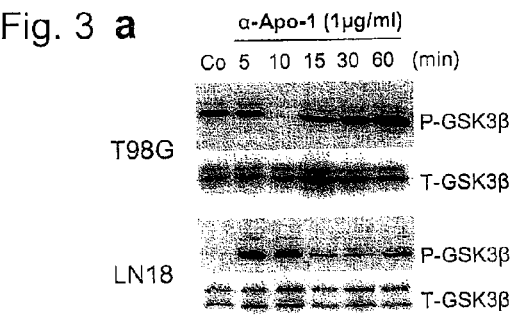
Figure 3:
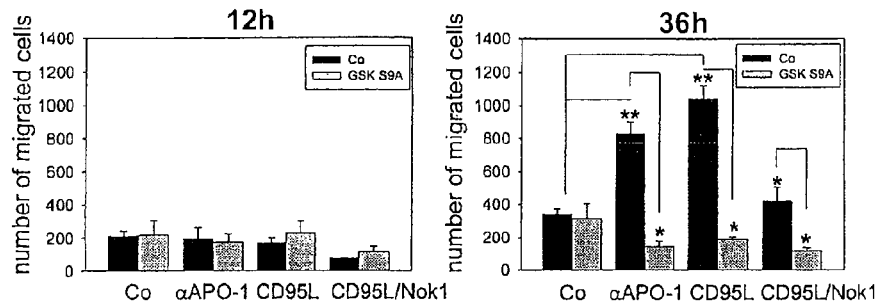
Figure 3:
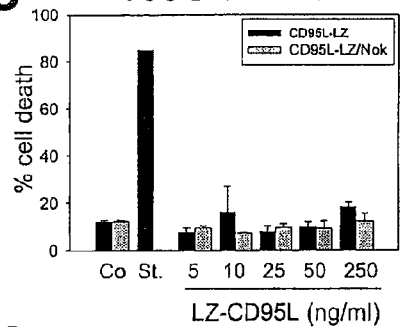
Figure 3:
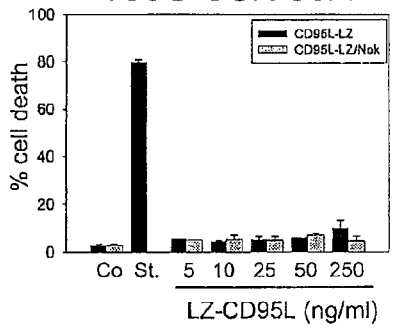
Figure 3:
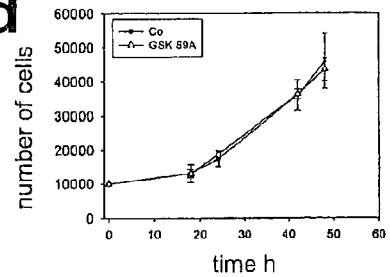
Figure 3:
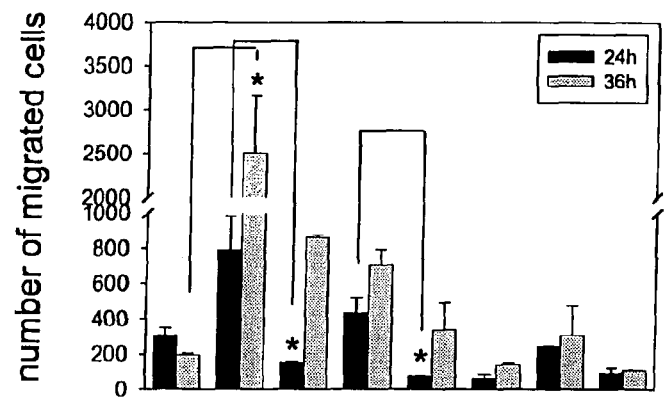
Figure 3:
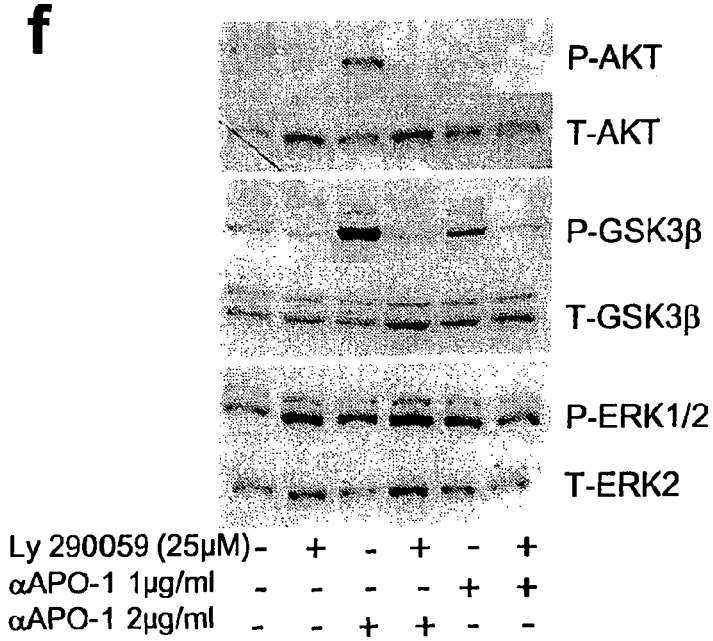
Figure 3:
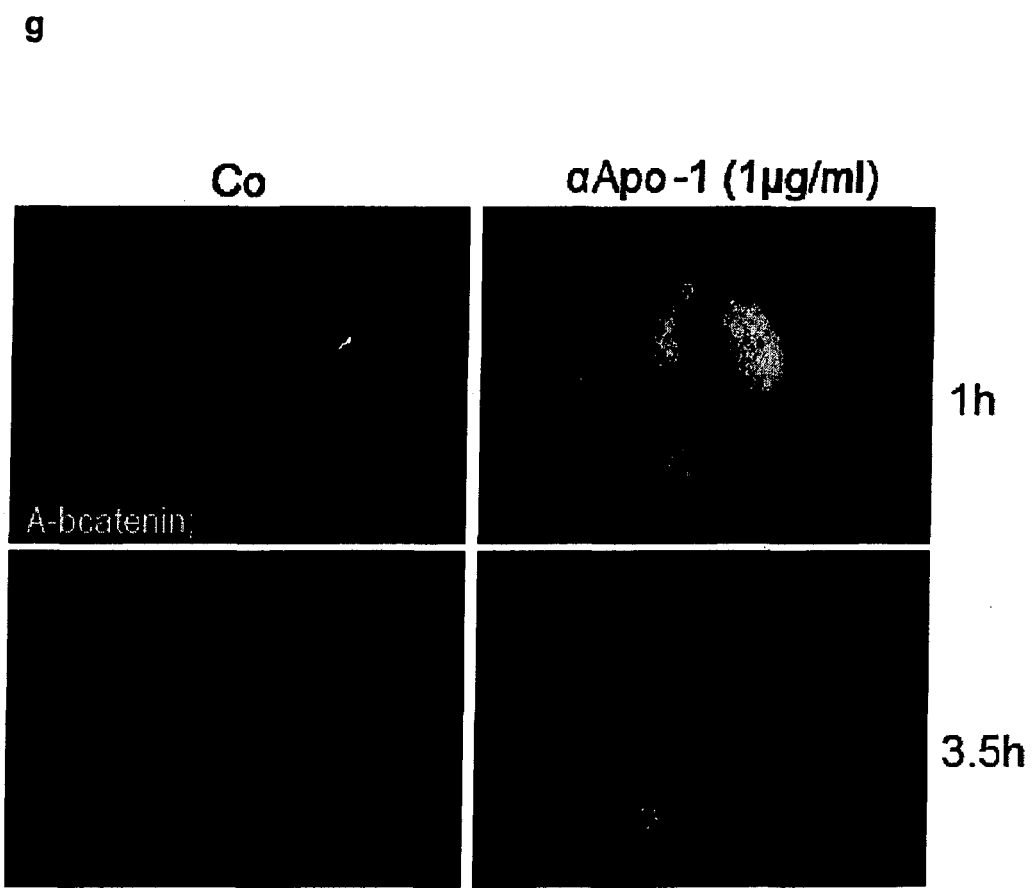
Figure 3:
Figure 3:
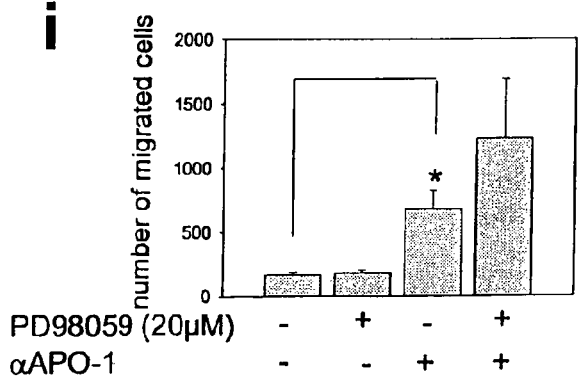

FIG. 3: CD95-induced migration is mediated via activation of ILK/AKT and the inhibition of GSK3β

(a) GSK3β was phosphorylated and thereby inhibited in T98G and LN18 cells upon treatment with α-Apo-1 (1 µg/ml). (b) T98G cells were infected with an empty lentiviral vector (Co) or a constitutively active GSK3β mutant (GSK S9A). GSK S9A infected T98G cells migrated significantly less than their empty vector counterparts upon treatment with α-Apo-1 (2 µg/ml) or LZ-CD95L (CD95L, 5 ng/ml) at 36 h. A neutralizing antibody to CD95L (Nok1 10 µg) blocked CD95L-induced migration of vector and GSK S9A infected cells. (c) GSK S9A infected T98G cells and the respective controls were stimulated with the indicated doses of LZ-CD95L (ng/ml) for 48 h and DNA fragmentation was analyzed by FACS. (d) Growth curves of T98G Co and GSK S9A are shown. (e) The ILK inhibitor (KP-SD1, 10 µM) blocked α-Apo-1-(2 µg/ml) and LZ-CD95L-induced (5 ng/ml) migration of T98G cells. (f) The PI3K inhibitor (LY 290059, 25 µM) blocked α-Apo-1-induced activation of AKT and inhibition of GSK3β in T98G cells. (g) Active β-catenin (green) was translocated to the nucleus upon stimulation with α-Apo-1 (1 µg/ml), phospho-GSK3β (red) did not change upon CD95 stimulation. DAPI (blue) was used to visualize the nuclei in T98G cells. (h) Cleavage of Caspase-8 in T98G, LN18 and Jurkat 16 (J16) was detected upon CD95 stimulation by Western Blotting. (i) The ERK inhibitor (PD 98059, 25 µM) did not interfere with the CD95-induced migration. Results are expressed as mean±S.E., *P<0.05, **P<0.01, and are representative of two experiments. P: phosphorylation, T: total.

Figure 4:
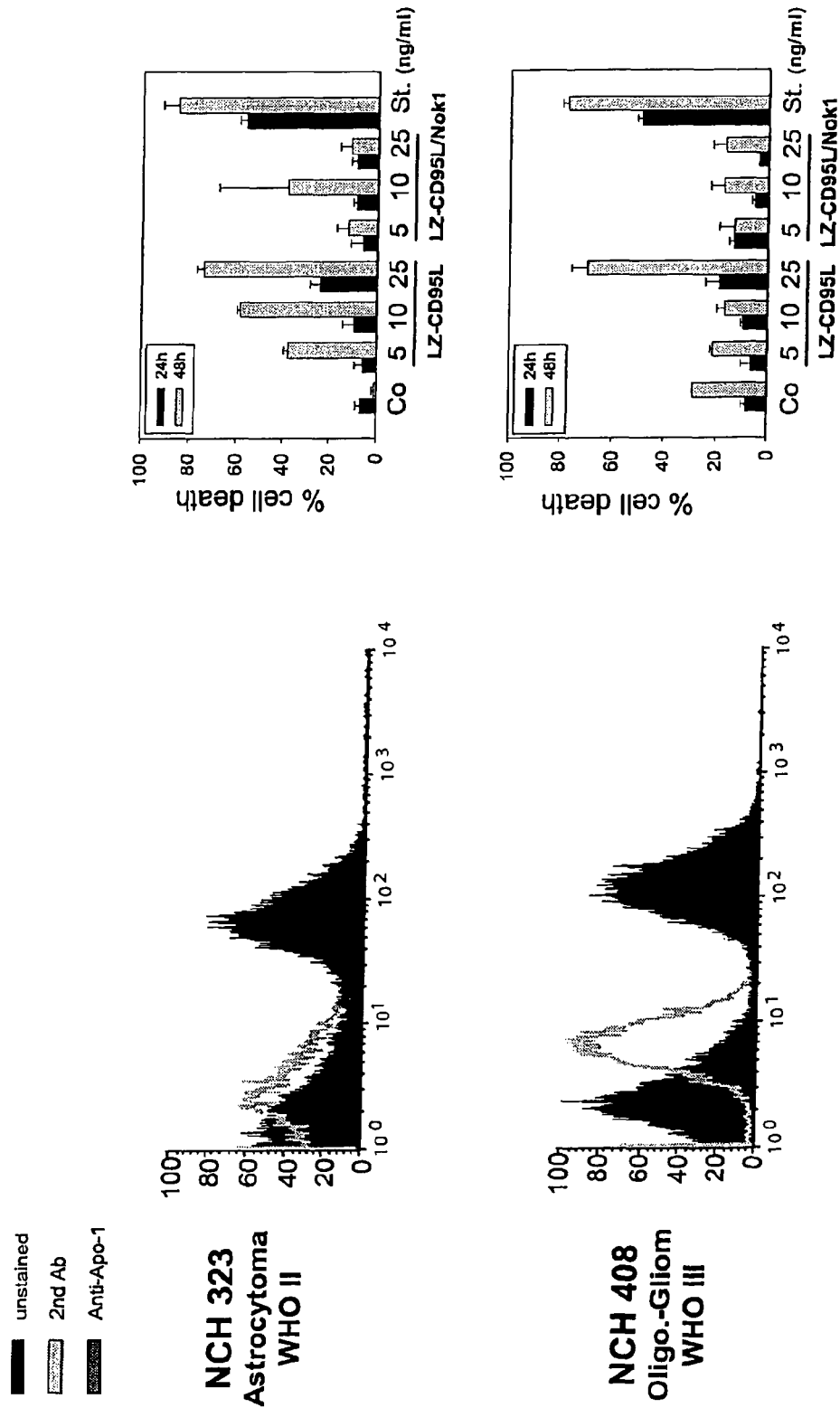
Figure 4:
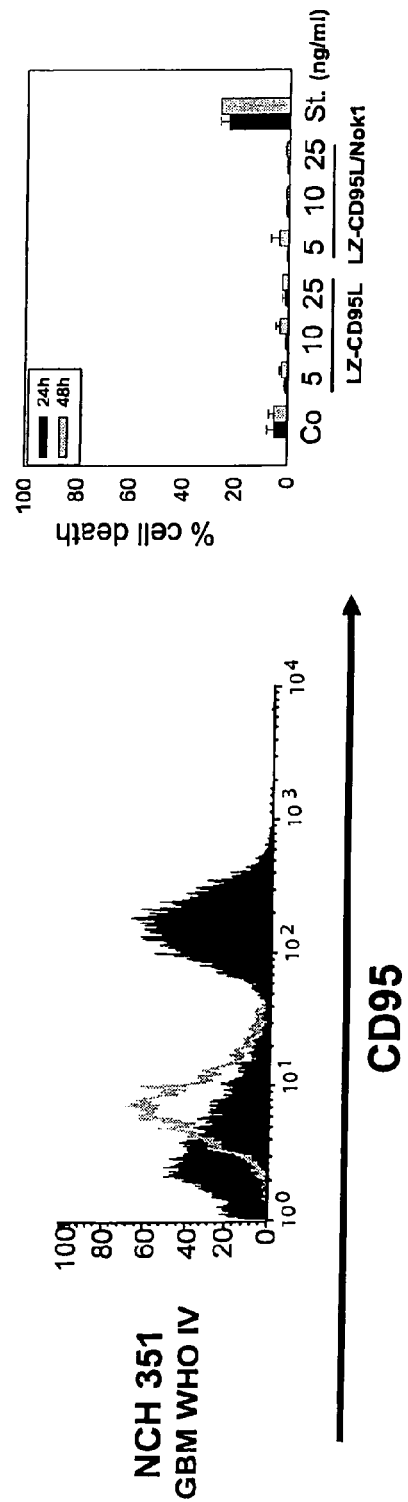

FIG. 4: Expression of the CD95/CD95L system in primary glioblastomas

FACS analysis of CD95 surface expression in primary astrocytoma, oligondendroglioma and glioblastoma cell lines with low passages (≤4). For DNA fragmentation cells were treated with indicated doses of LZ-CD95L (CD95L) for 24 h and 48 h and analyzed by FACS.

Figure 5:
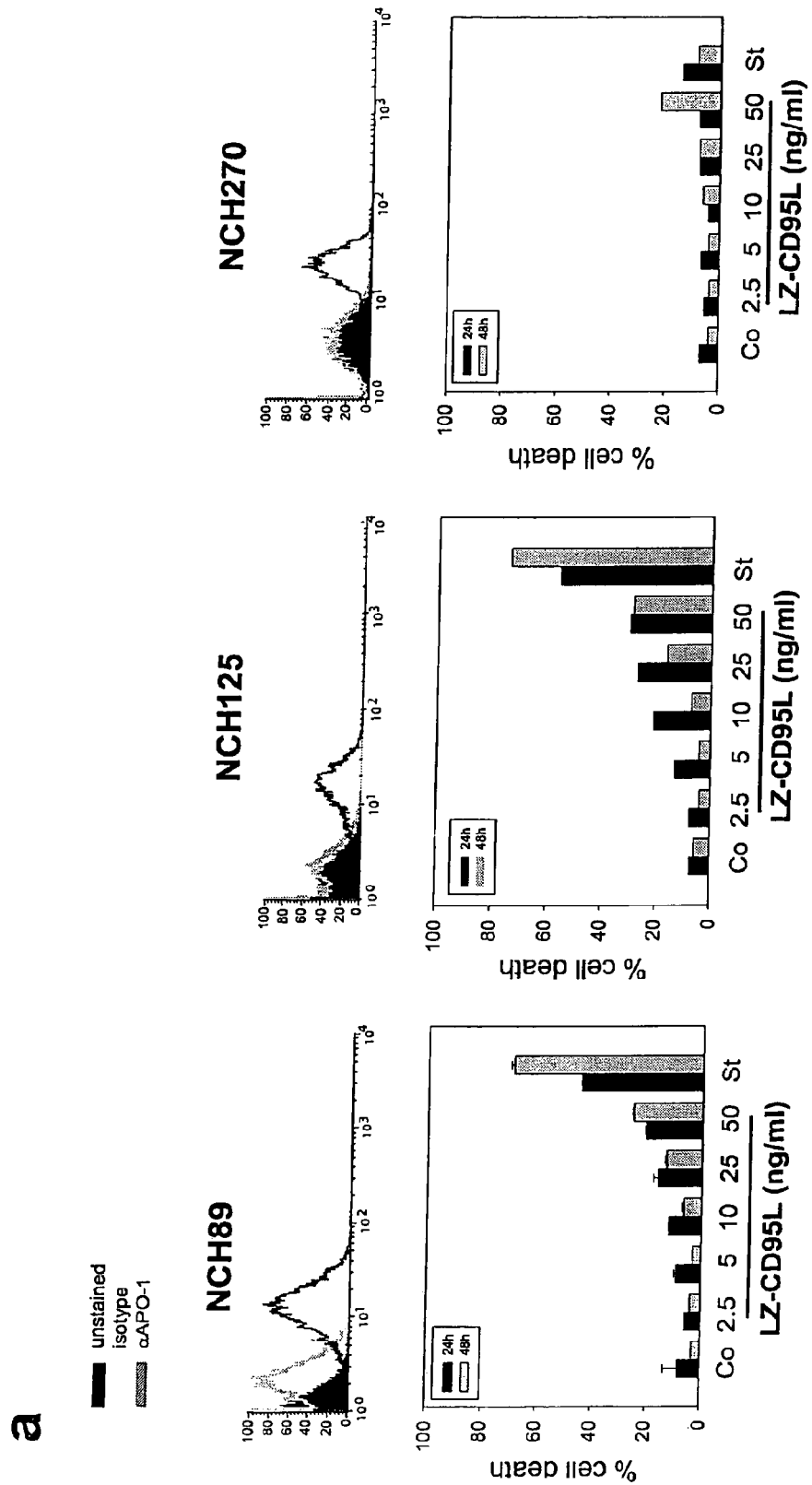
Figure 5:
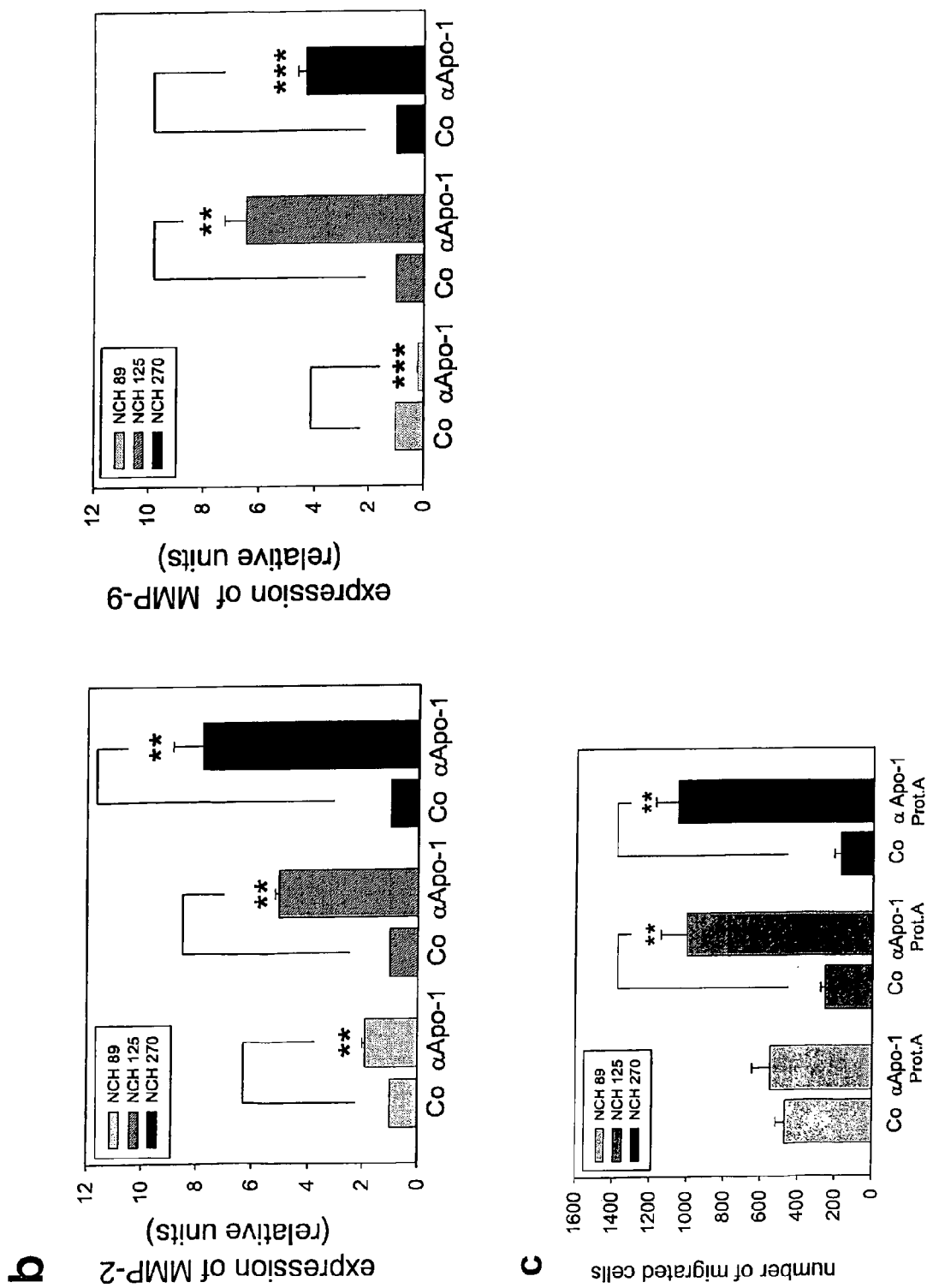

FIG. 5: Function of the CD95/CD95L system in apoptosis-resistant primary glioblastomas (a) FACS analysis of CD95 surface expression in primary NCH (89, 125 and 270) glioblastoma cell lines highly passaged (≥50). For DNA fragmentation cells were treated with indicated doses of LZ-CD95L (ng/ml) for 24 h and 48 h and analyzed by FACS Results are depicted as mean±S.D. and are representative for three independent experiments. (b) NCH 89, 125 and 270 cells showed an upregulation of MMP-2 and MMP9 mRNA levels 40 h after α-Apo-1 (1 µg/ml) treatment as detected by quantitative real-time PCR. Results are depicted as mean±S.E., *P<0.05, P<0.01, *P<0.005 and are representative for three independent experiments. (c) Migration assay for NCH 89, 125 and 270 cells treated with α-Apo-1 (0.1 µg/ml+ProteinA). Results are expressed as mean±S.E., *P<0.05, **P<0.01 and are representative of two independent experiments.

Figure 6:
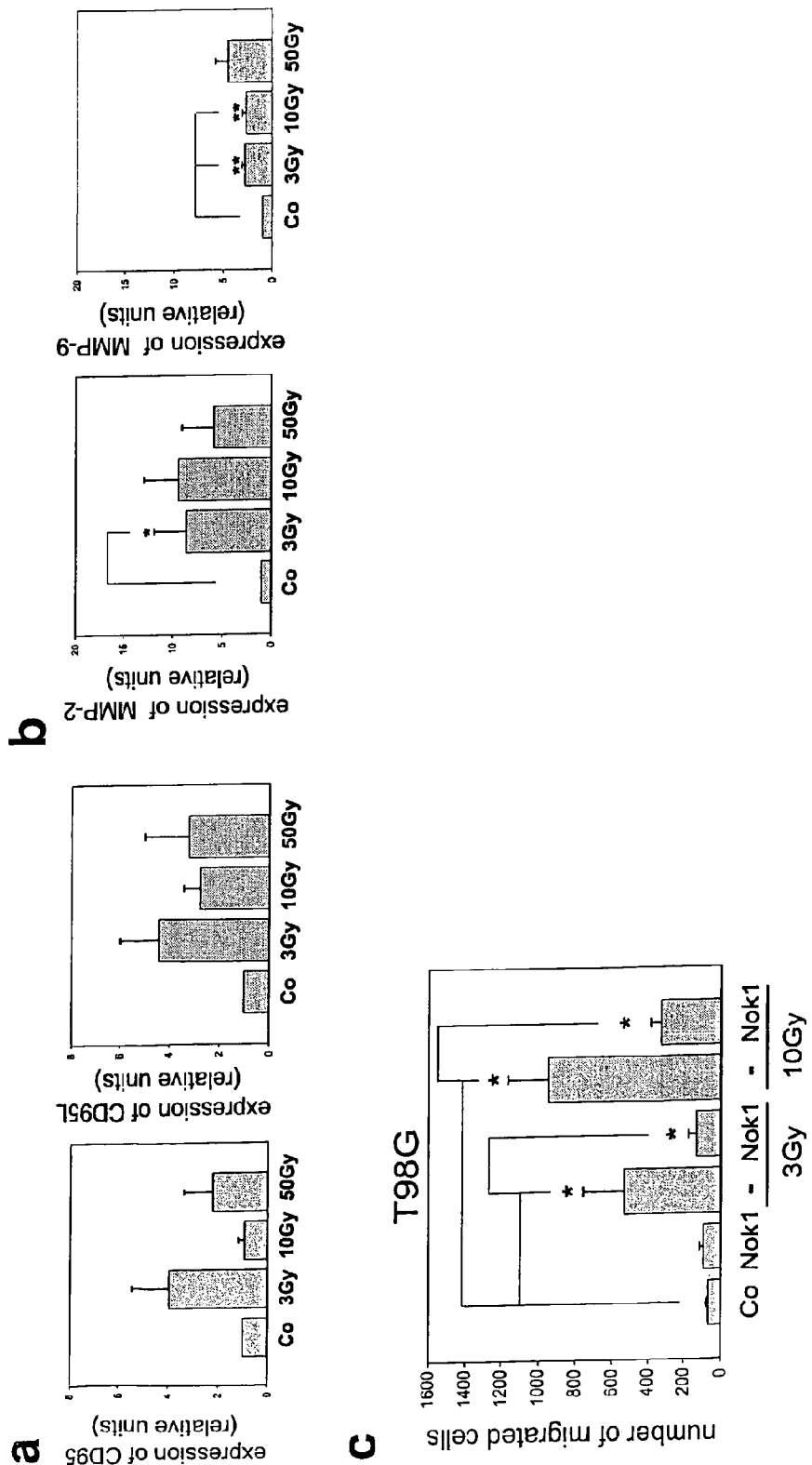
Figure 6:
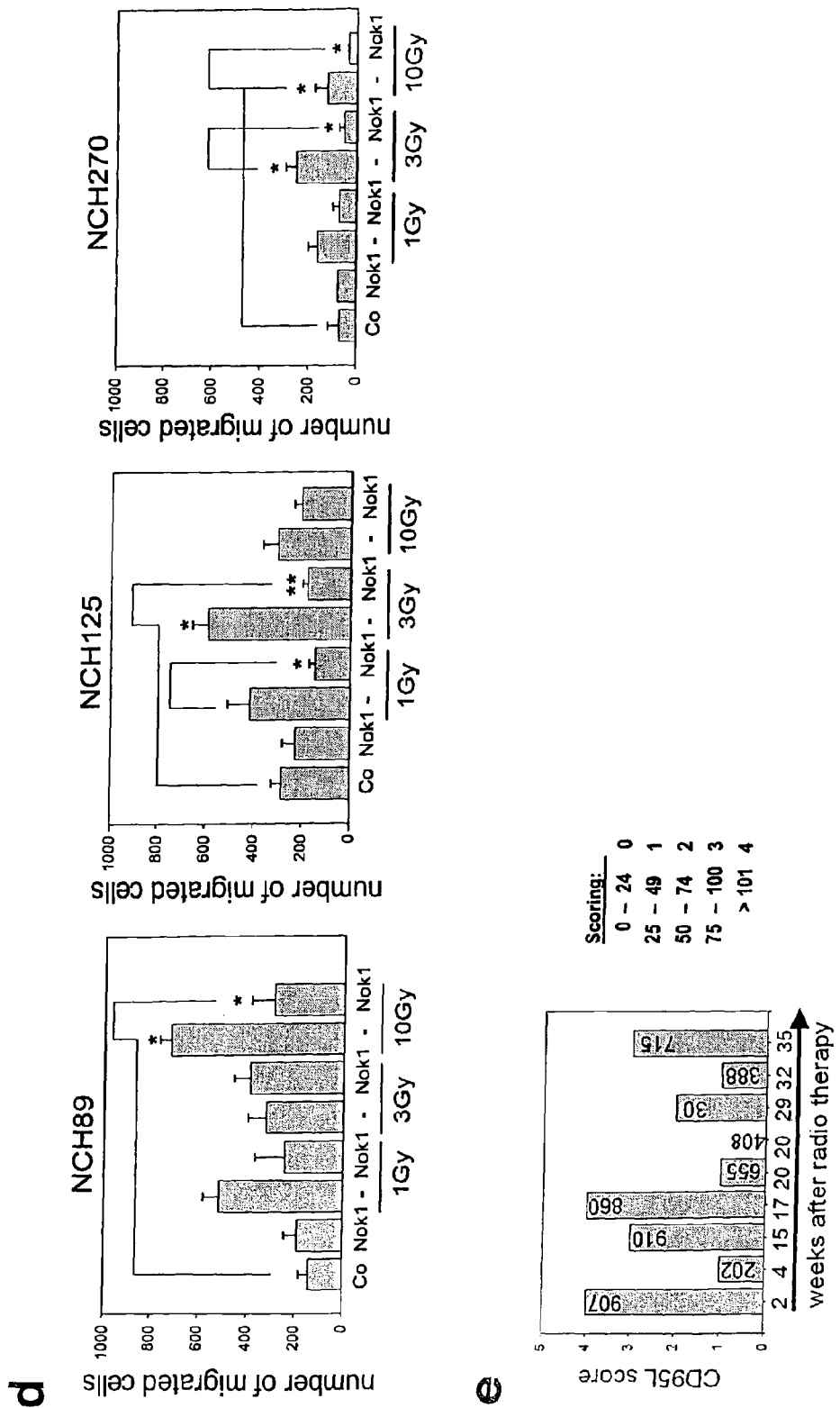
Figure 6:
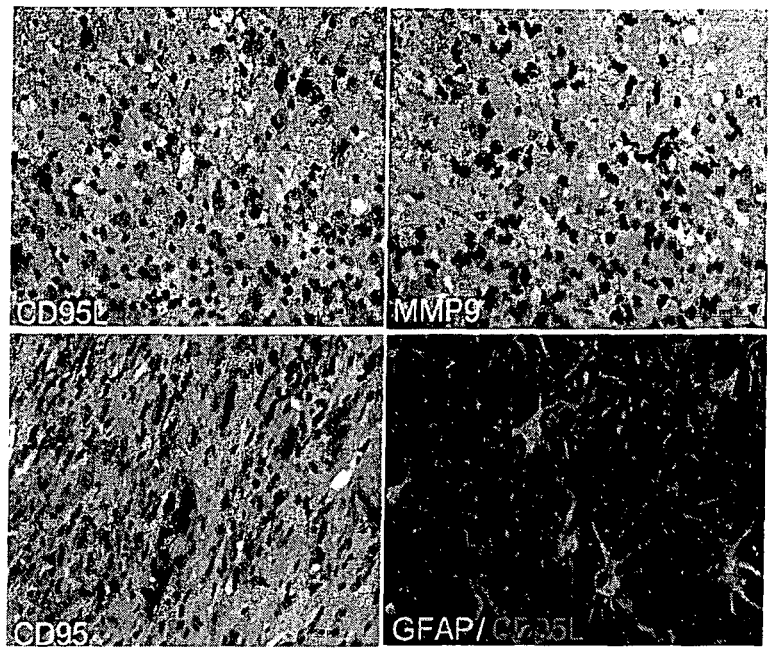

FIG. 6: γ-irradiation-induced migration in T98G and primary glioblastoma cells (a+b) T98G cells were γ-irradiated at the indicated doses and mRNA-levels of CD95 and CD95L (a) and MMP-2 and -9 (b) were determined by quantitative real-time PCR after 40 h. Results are depicted as mean±S.E., *P<0.05, **P<0.01 and are representative of three independent experiments. (c+d) Induction of migration in T98G (c) and primary NCH cells (NCH 125, 270 and 89) (d) upon γ-irradiation. A neutralizing antibody to CD95L (Nok1, 10 µg) blocked γ-irradiation-induced migration. Results are expressed as mean±S.E., *P<0.05 and representative for two independent experiments. (e) CD95L scoring of 9 different recurrent gliomas following radiotherapy. 3 areas per tumor were analyzed and the CD95L positive cells were counted and scores assigned according to the number of positive cells. Recurrent tumors analysed were NCH 907, 202, 910, 860, 655, 408, 30, 388 and 715. (f) Stainings were performed on consecutive recurrent tumor tissue sections for CD95L, CD95 and MMP9, as well as the double staining for GFAP (green) and CD95L (red).

Figure 7:
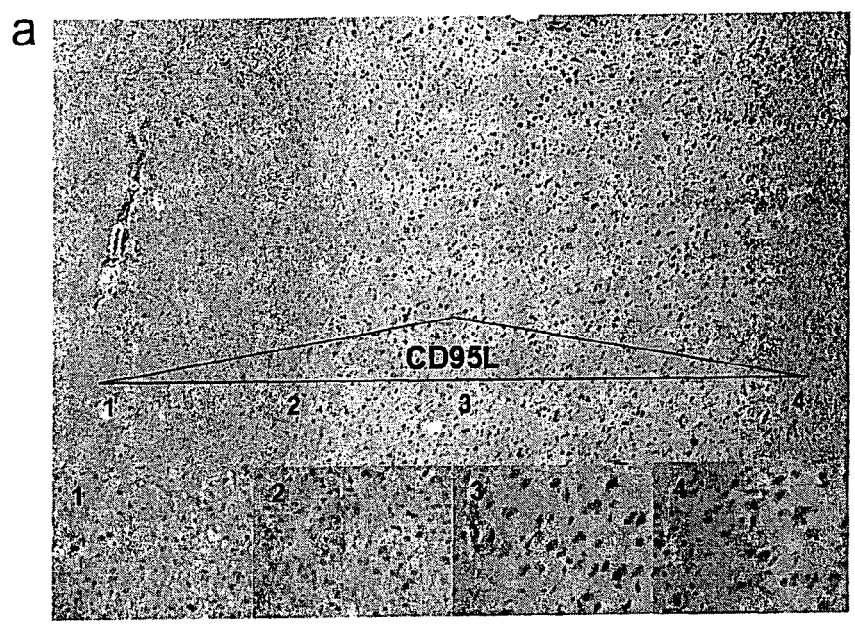
Figure 7:
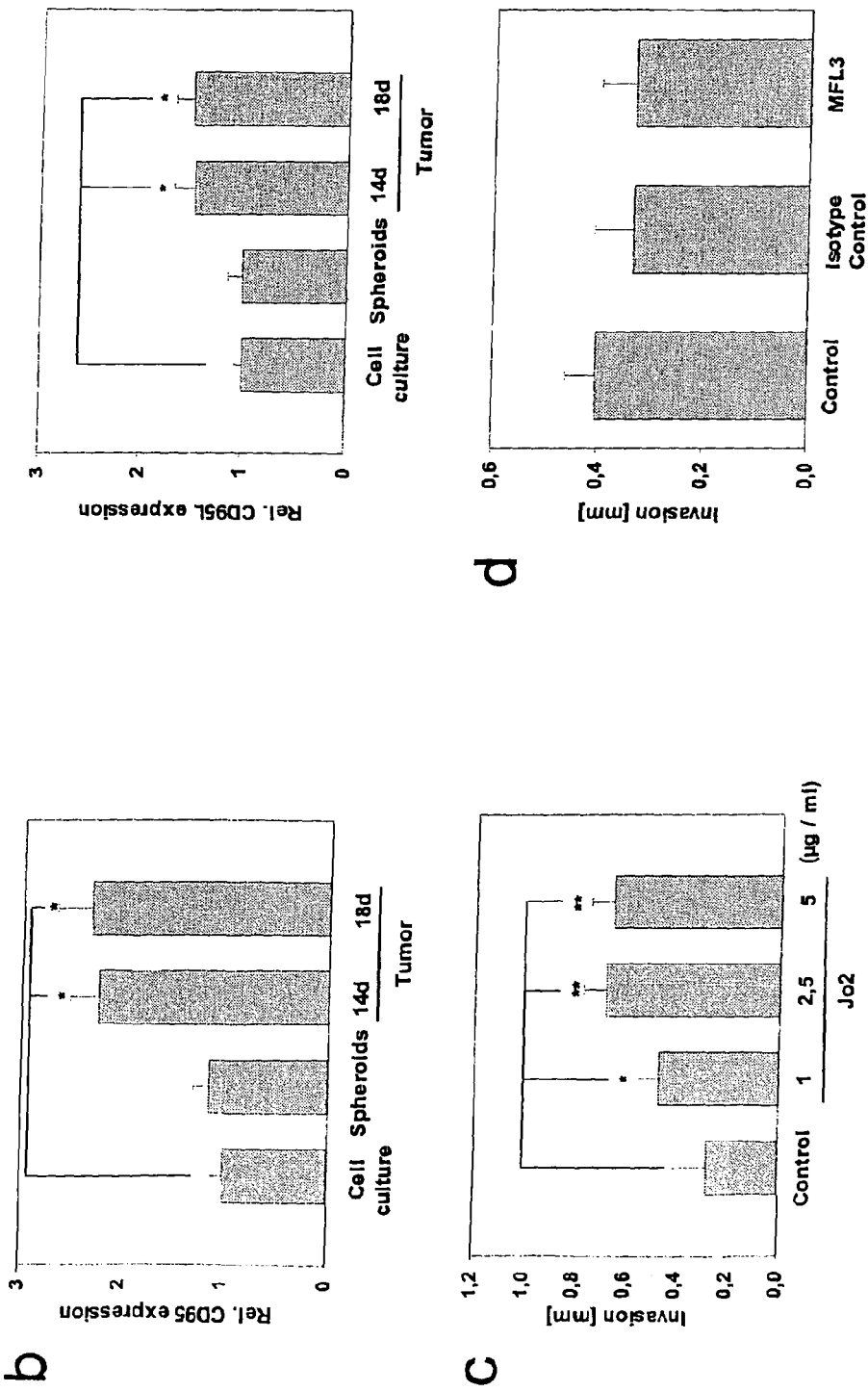
Figure 7:
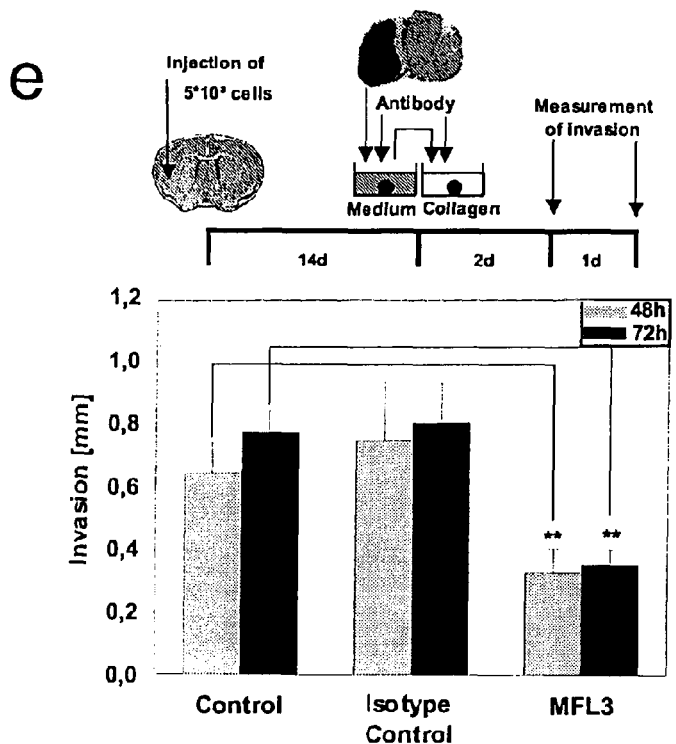
Figure 7:
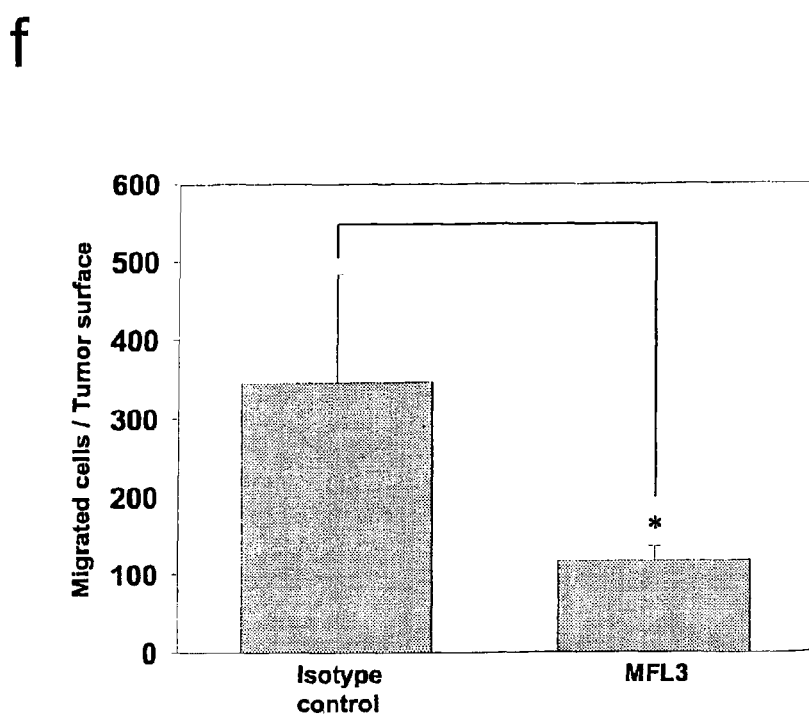

FIG. 7: CD95 and CD95L are upregulated on murine glioma cells in vivo and induce migration (a) Immunohistochemical staining for CD95L of primary GBM. (b-c) CD95 and CD95L surface expression on the murine glioma cell line SMA-560 was determined under normal cell culture conditions, after the formation of spheroids or following intracranial implantation. Changes of CD95 (b) and CD95L (c) (GeoMean from BD CellQuest Pro) under the aforementioned conditions were normalized to expression levels under cell culture conditions. Results represent three independent experiments and are expressed as mean±S.D., *P<0.05. (d) Spheroid cultures were embedded into a collagen matrix and treated with antibodies to CD95 (Jo2), a neutralizing antibody to CD95L (MFL3) or the appropriate isotype control antibody at the indicated concentrations. The migration of cells was monitored over 48 h and the distance of cells to the spheroid's border is depicted (n=10 cells, 3 spheroids per treatment). (e) Experimental setup. Migration of tumor explants into collagen after treatment with either MFL3 or the appropriate istoype control is depicted as described above (n=10, 3 spheroids per treatment). (f) Numbers of SMA-560 cells in the contralateral hemisphere of Vm/Dk mice either treated with MFL3 or the isotype control antibody were counted and normalized to tumor surface. Shown results are representative of two independent experiments and expressed as mean±S.D., *P<0.05, **P<0.001.

Figure 8:
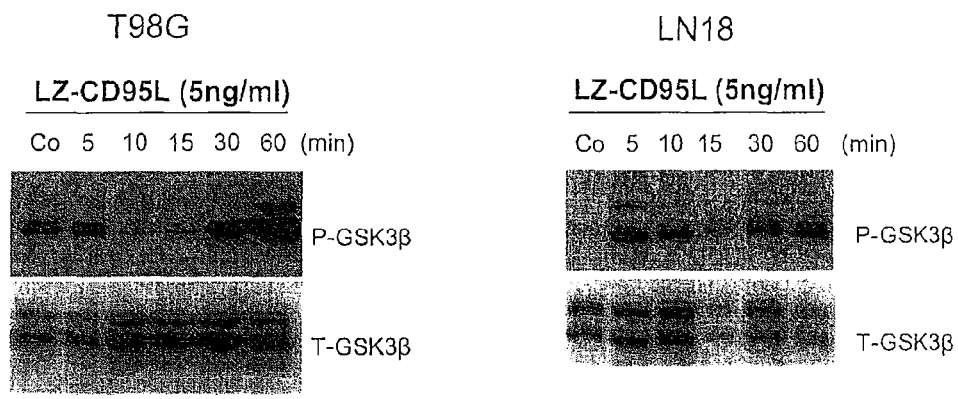
Figure 8:
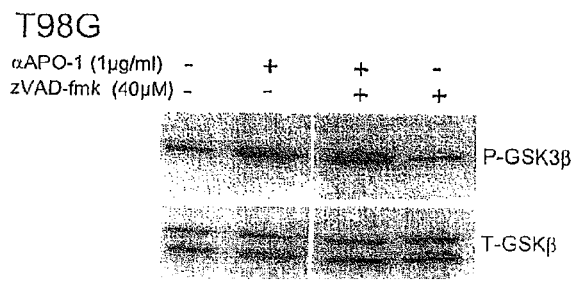
Figure 8:
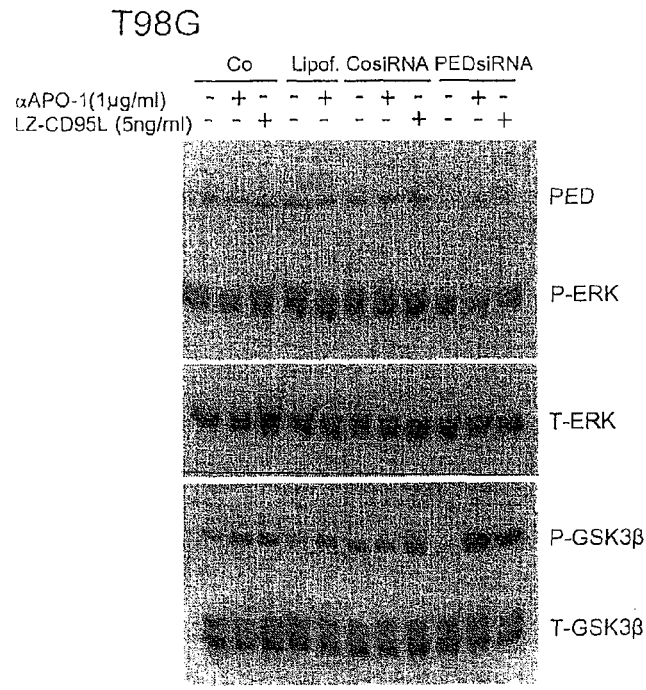

FIG. 8: Inhibition of GSK3β is Caspase Independent (a) GKS3β is phosphorylated and thereby inhibited in T98G and LN18 cells upon treatment with LZ-CD95L (5 ng/ml). (b) Preincubation with the caspase inhibitor zVAD-fmk (40 µM) did not interfere with α-Apo-1 (2 µg/ml)-induced inhibition of GSK3β. (c) PED knockdown with siRNA blocked the activation of ERK, but did not change the α-Apo-1-induced inhibition of GSK3β. Results are representative of two independent experiments.

Figure 9:
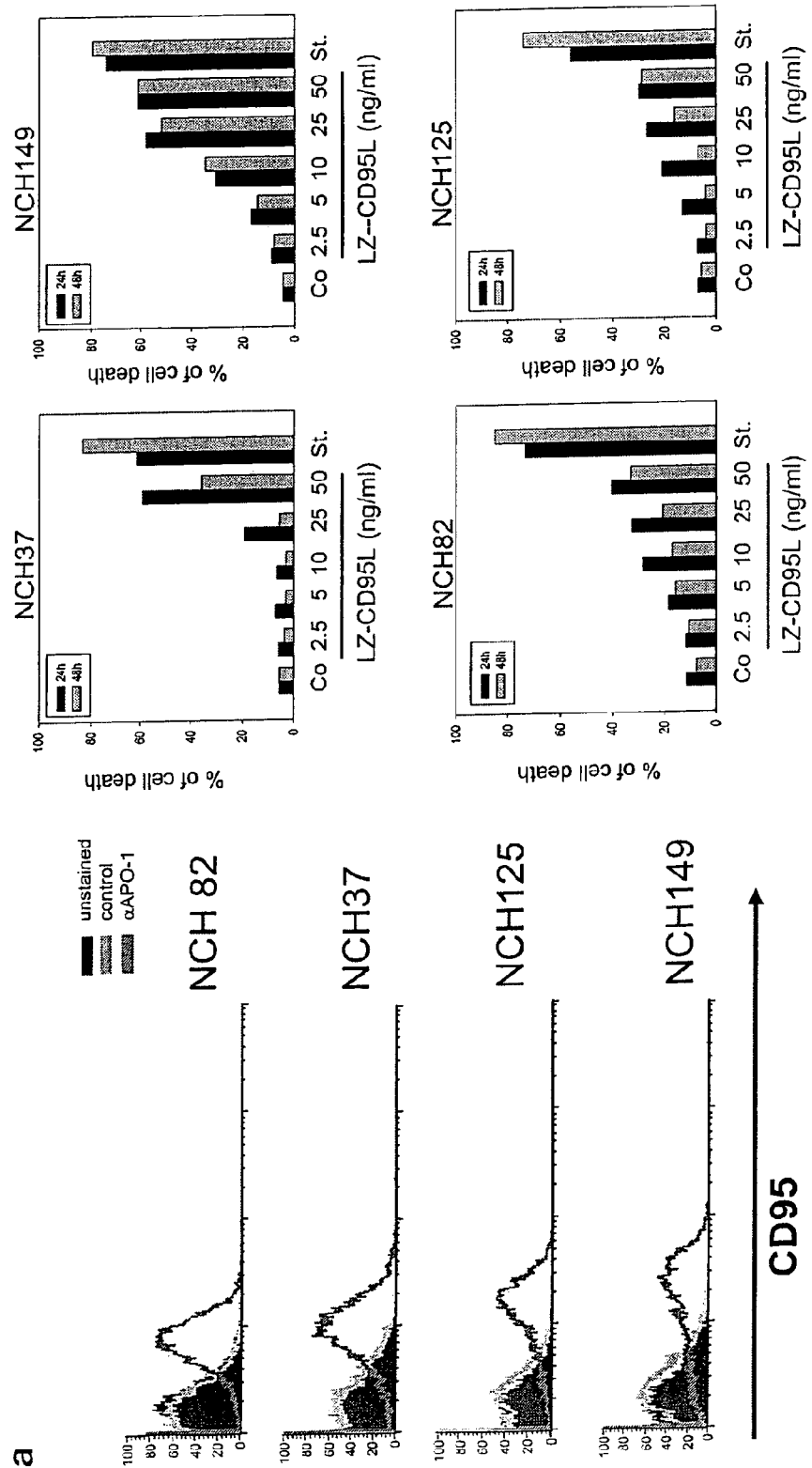
Figure 9:
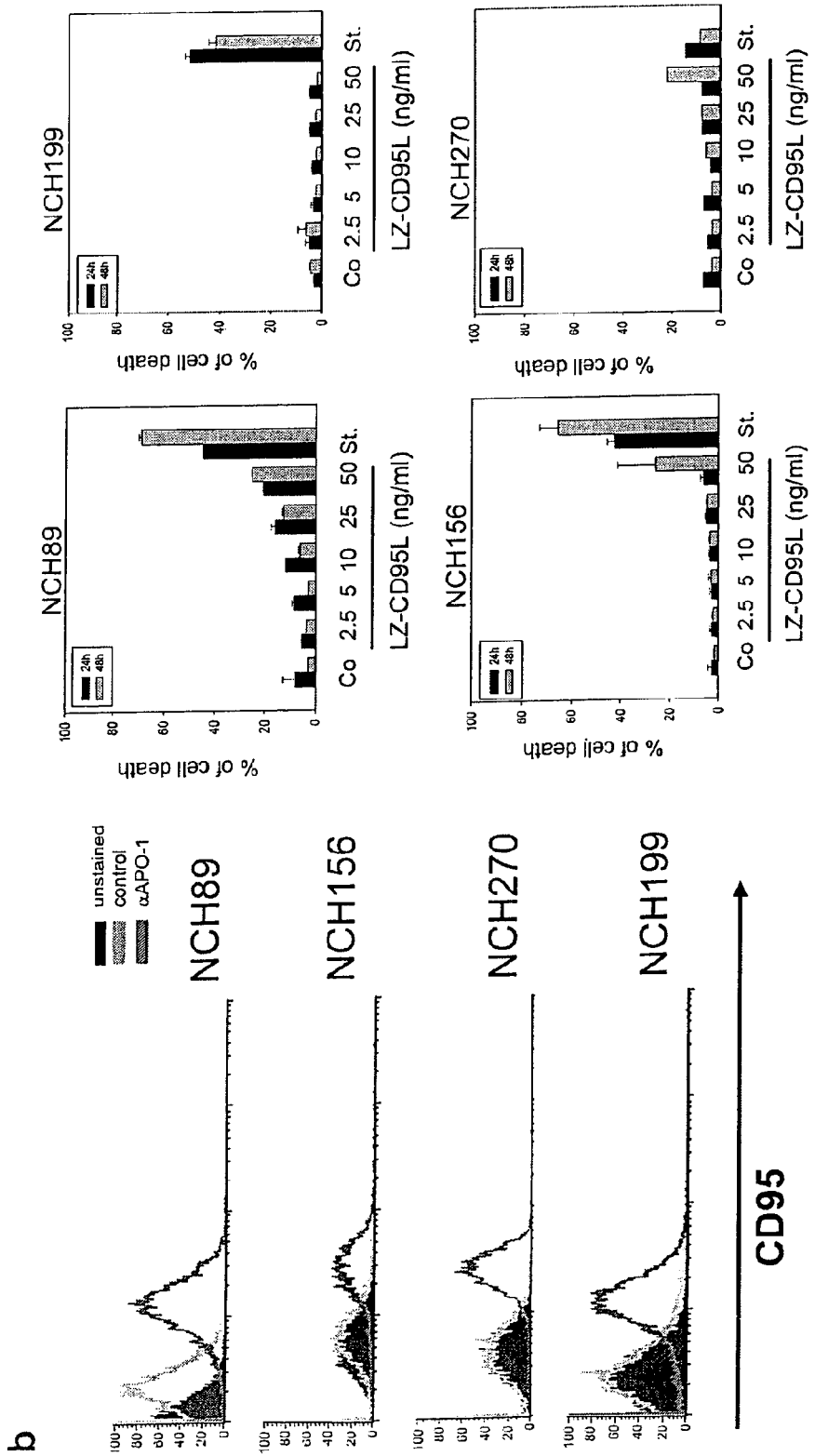
Figure 9:
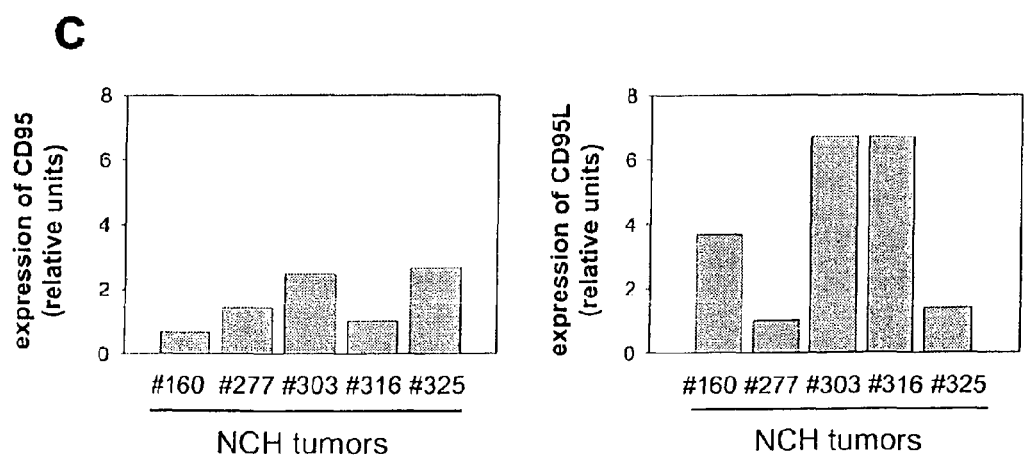

FIG. 9: Expression and function of the CD95/CD95L system in primary glioblastomas (a-b) FACS analysis of CD95 surface expression in primary glioblastoma cell lines (NCH 82, 37, 125, 149, 89, 156, 270 and 199) with high passages 50). For DNA fragmentation cells were treated with indicated doses of LZ-CD95L (ng/ml) for 24 h and 48 h and analyzed by FACS. Results are given as mean±S.D. and are representative of two independent experiments. (c) mRNA levels of CD95 and CD95L in human tumor tissue, determined by quantitative real-time PCR. Results are representative of two independent experiments.

Figure 10:
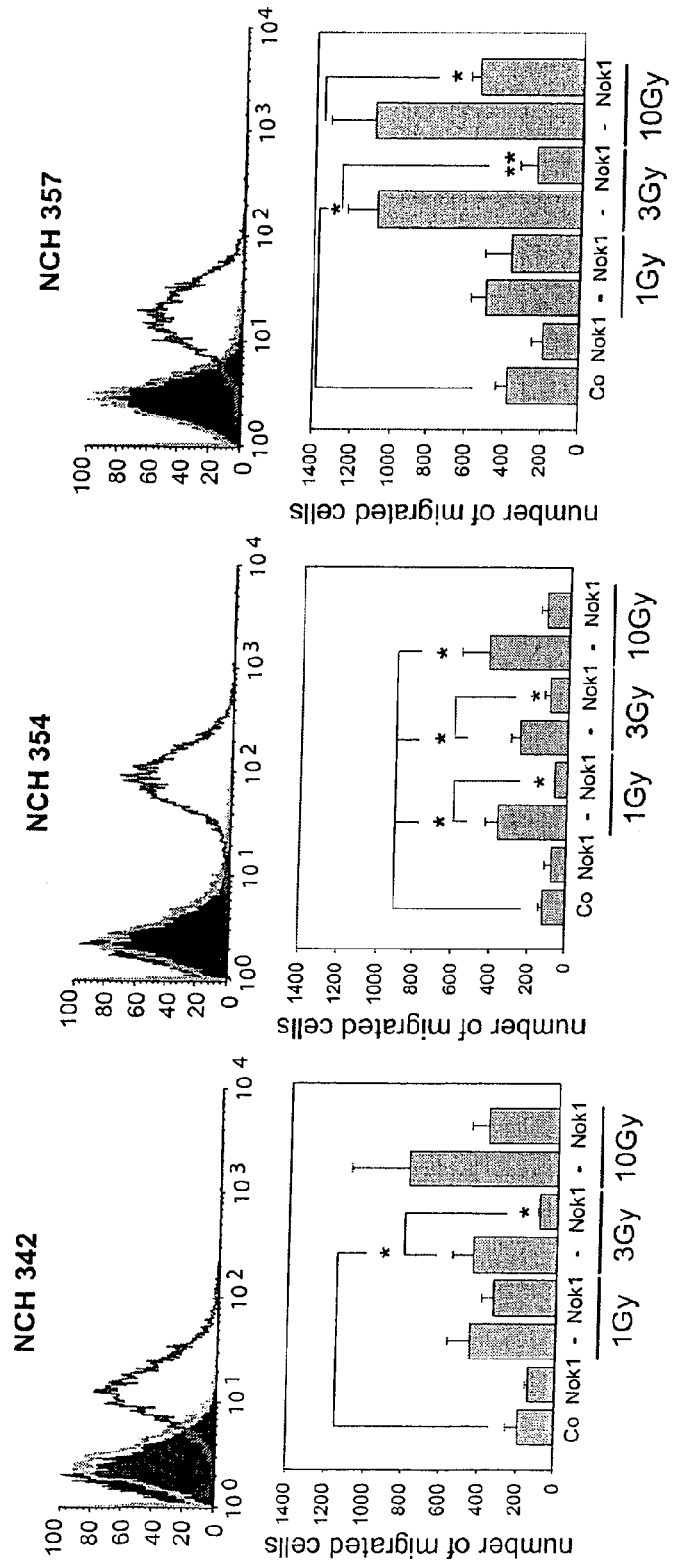
Figure 10:
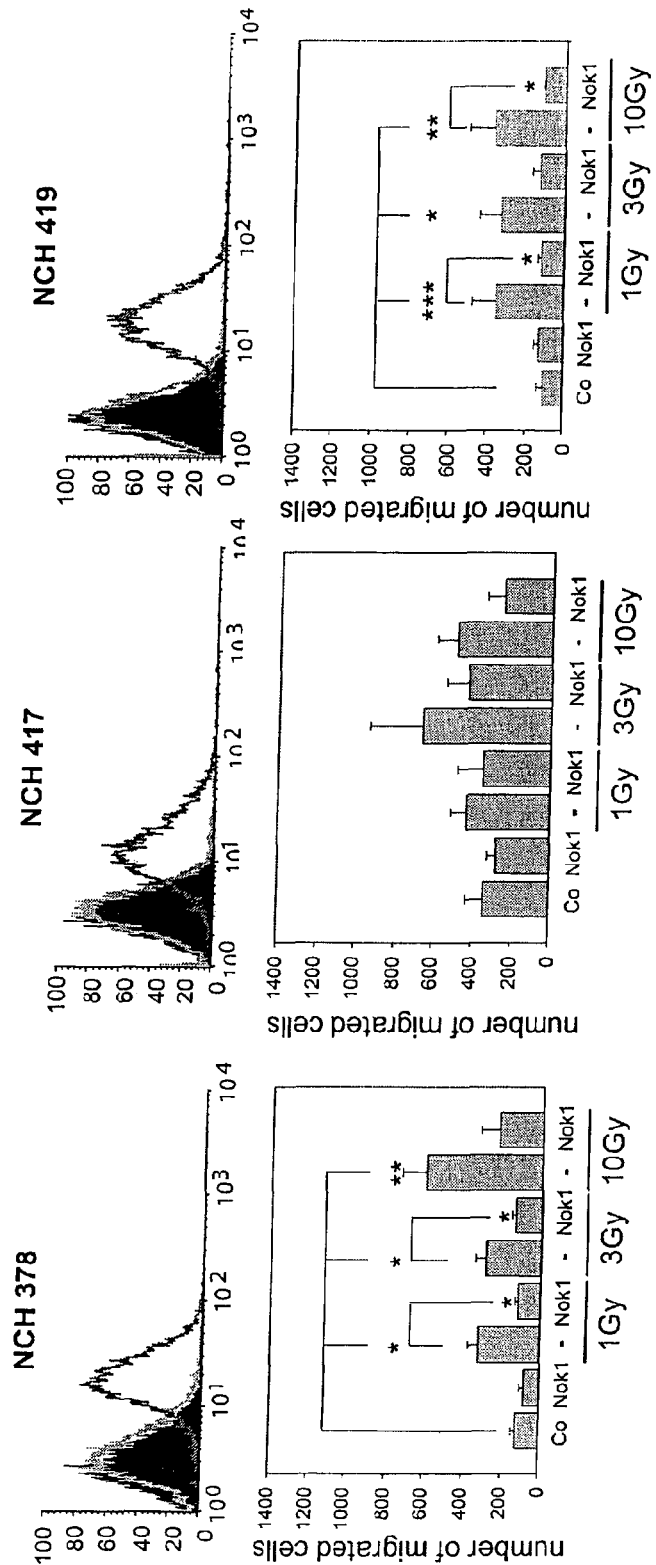
Figure 10:
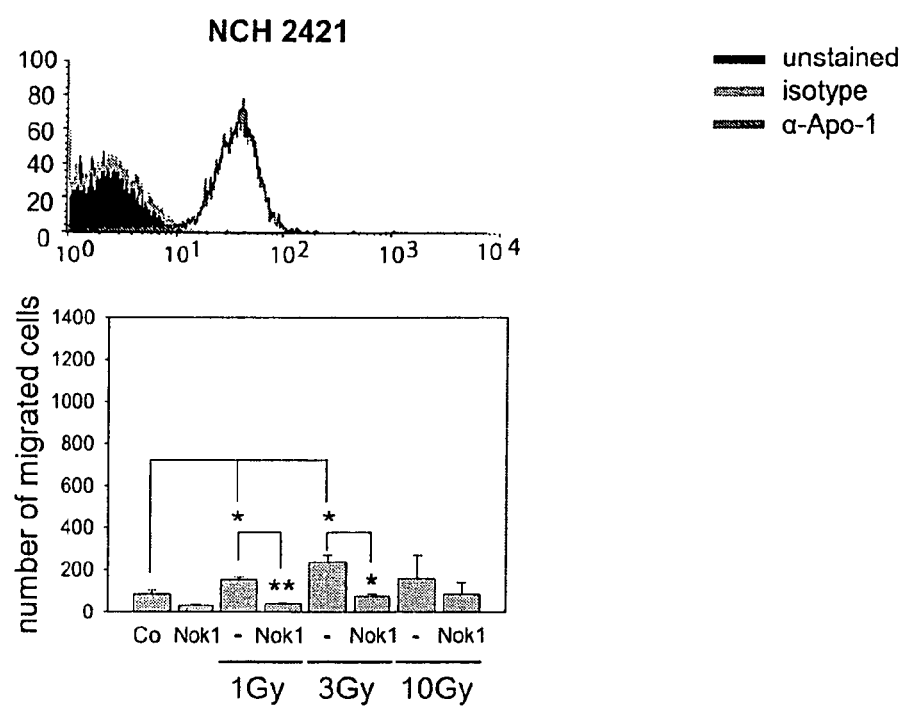

FIG. 10: Influence of irradiation on primary glioblastoma migration

FACS analysis of CD95 surface expression in primary glioblastoma cell lines (NCH 342, 354, 357, 378, 417, 419 and 2421). Induction of migration in these primary NCH cells upon γ-irradiation, which could be blocked by a neutralizing antibody to CD95L (Nok1, 10 µg). Results are expressed as mean±S.E., *P<0.05, P<0.01, *P<0.005 and representative of two independent experiments.

Figure 11:
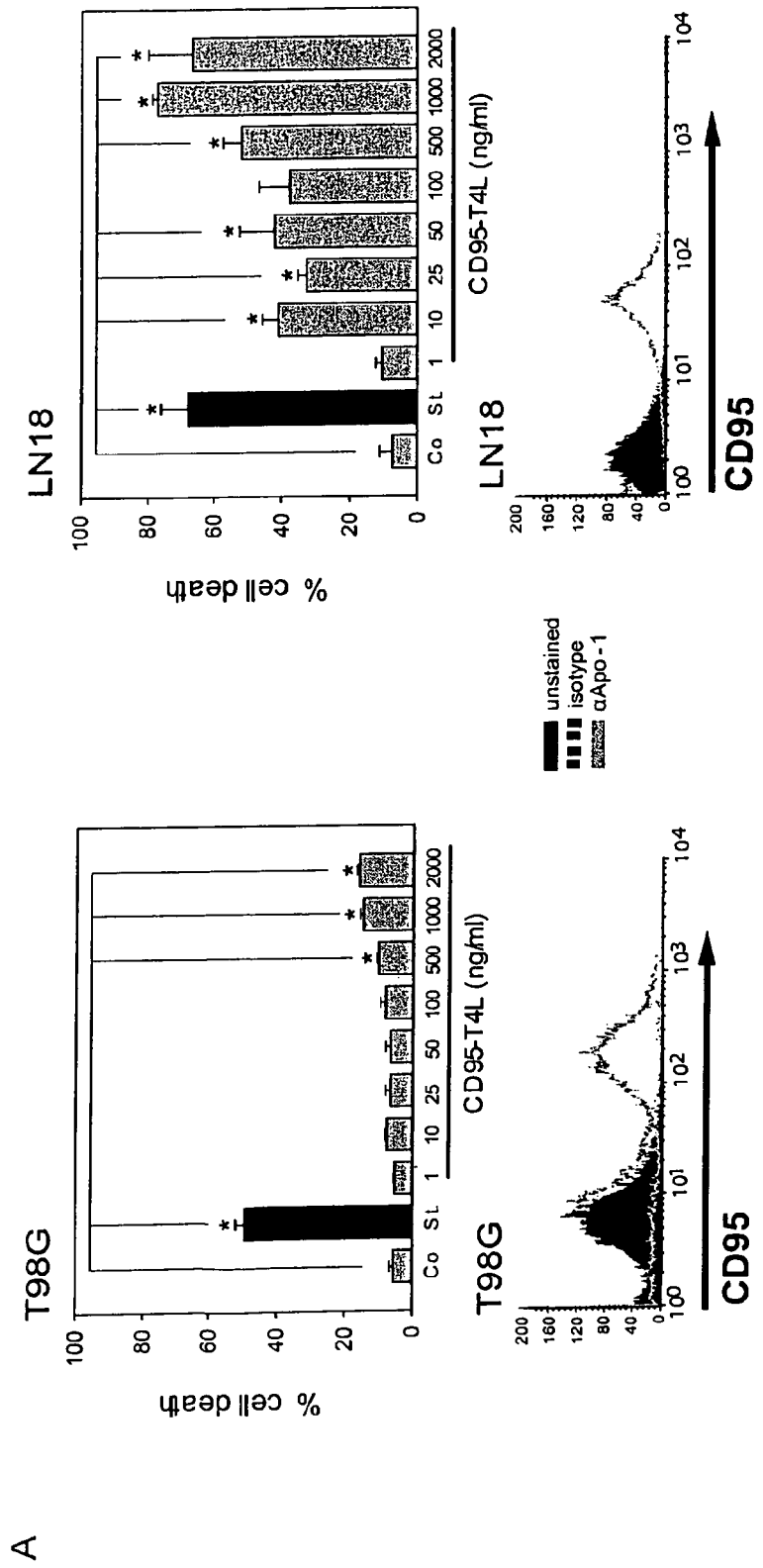
Figure 11:
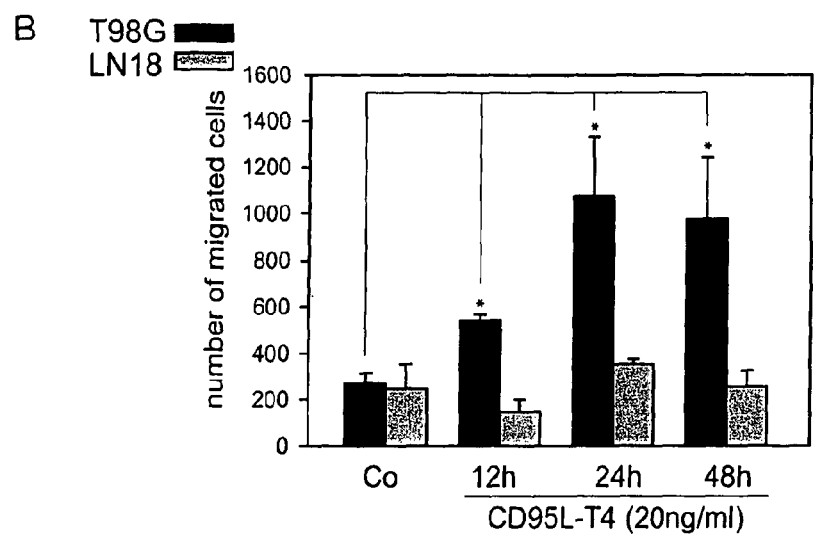
Figure 11:
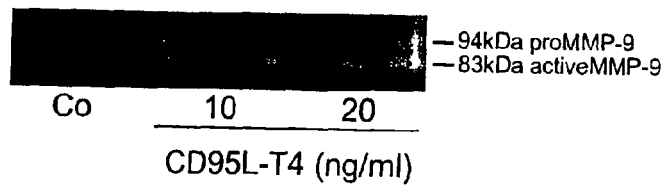
Figure 11:
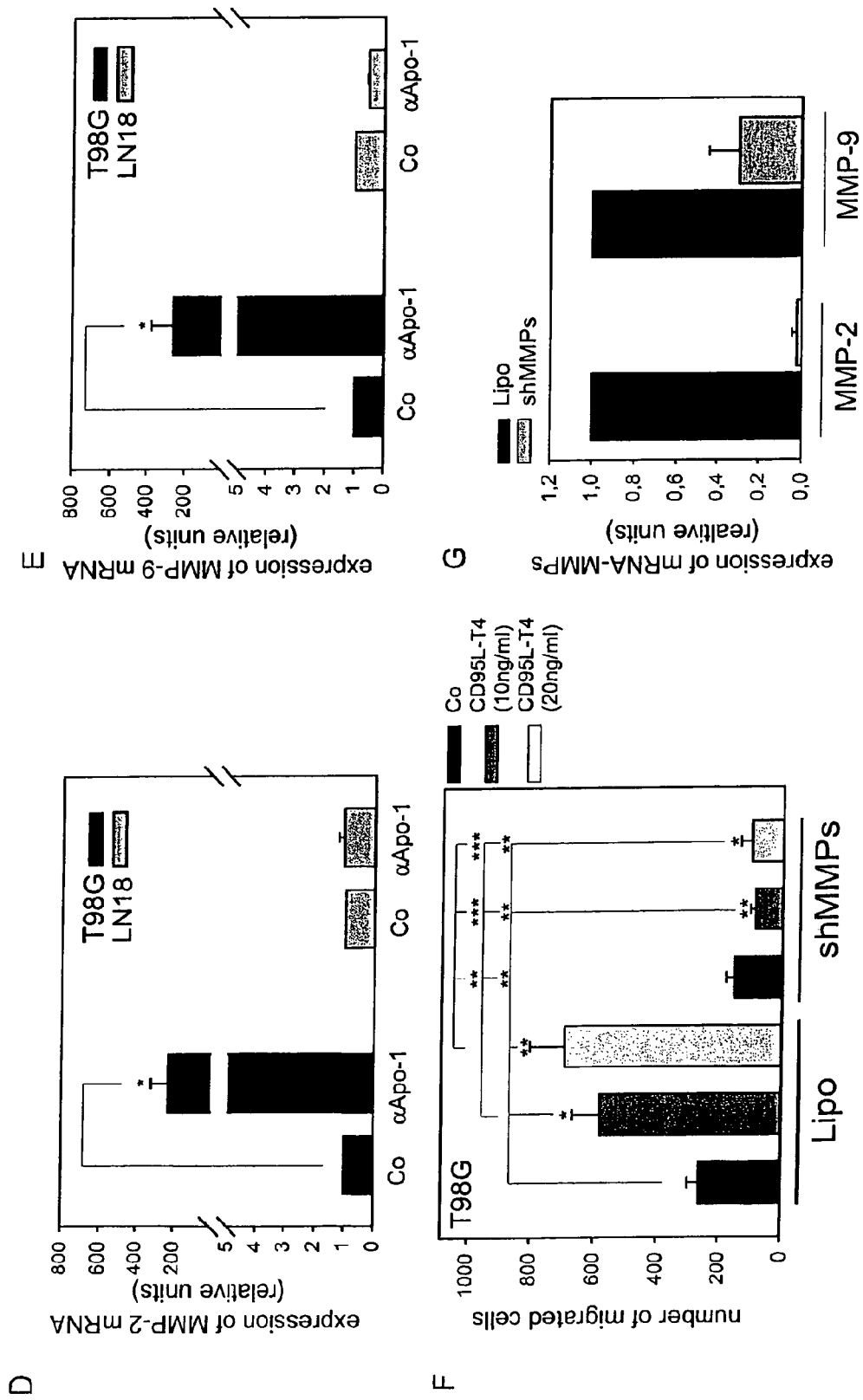

FIG. 11: CD95 triggers invasion of apoptosis resistant cells via MMPs (A) The glioblastoma cell lines T98G and LN18 were incubated with the indicated concentrations of CD95L-T4, Staurosporin (St., 1 µM) or left untreated (Co). After 24 h DNA fragmentation was analyzed by FACS (upper panel). FACS analysis of CD95 surface expression in the T98G and LN18 (lower panel). (B) T98G and LN18 cells were treated with CD95L-T4 or left untreated, to detect single cell migration through a Boyden chamber with 8 µm pore size. (C) T98G cells were treated with CD95L-T4 for 24 h or left untreated. Thereafter, MMP-9 activity was assessed by Gel Zymography. (D and E) T98G and LN18 cells were treated with αApo-1 for 48 h or left untreated. Expression of MMP-2 and MMP-9 was measured by quantitative real-time PCR. Data are results from five independent experiments as mean±S.E., *P<0.05. (F) T98G cells were transfected with a siRNA pool against MMP-2 and MMP-9 (shM-MPs) or with Lipofectamine alone (Lipo). 48 h after transfection, cells were treated with CD95L-T4, 48 h afterwards migration was measured in a two dimensional migration assay. (G) Expression of MMP-2 and MMP-9 as measured by quantitative-RT-PCR. Results are expressed as mean±S.E., *P<0.05; P<0.001; *P<0.0001 and are representative of at least two independent experiments.

Figure 12:
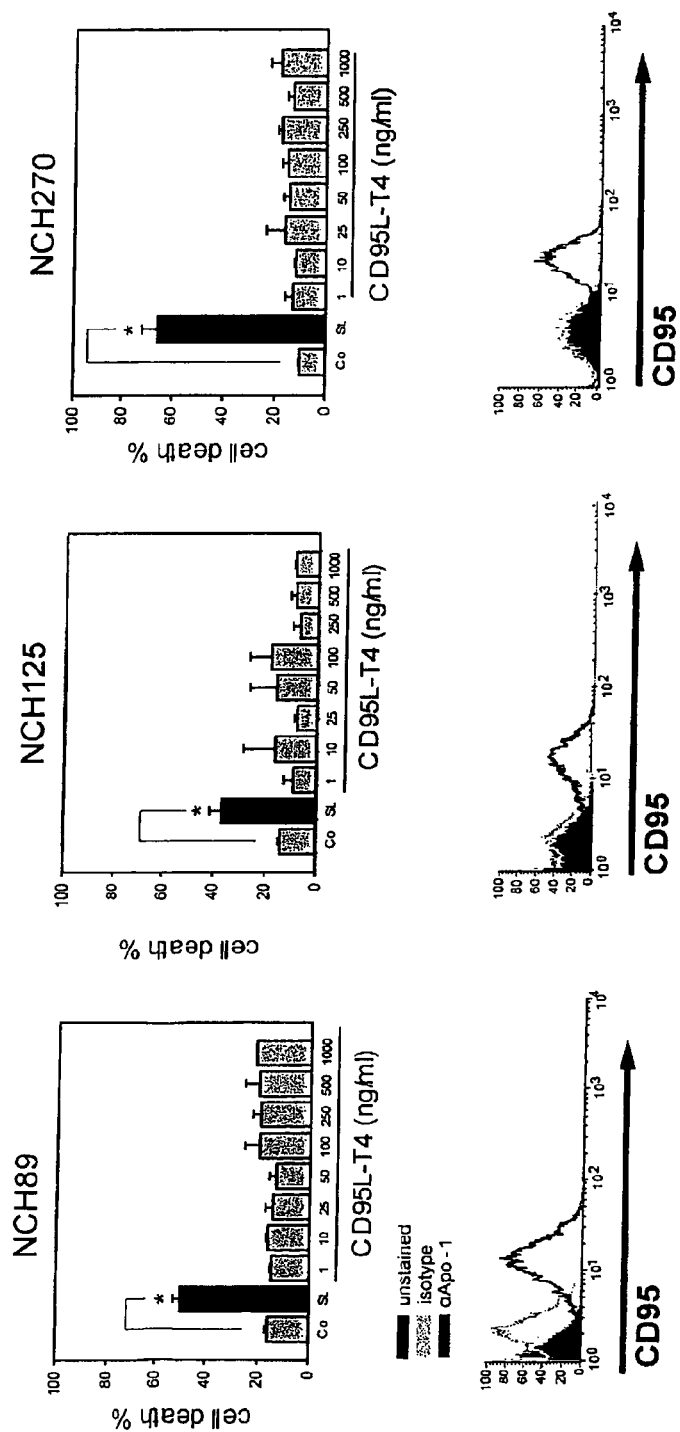
Figure 12:
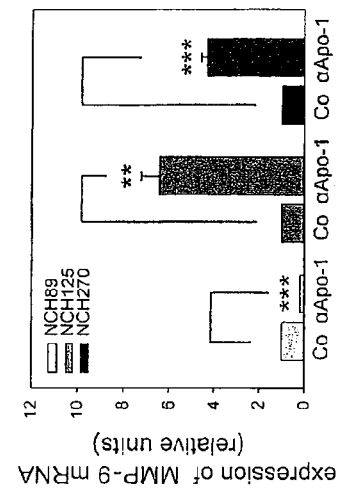
Figure 12:
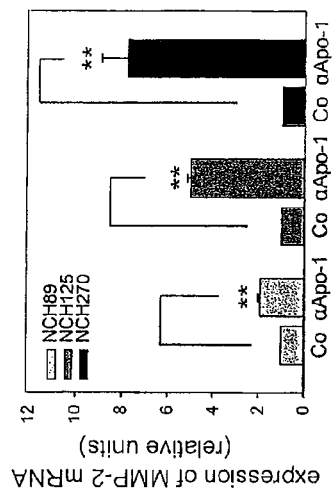
Figure 12:
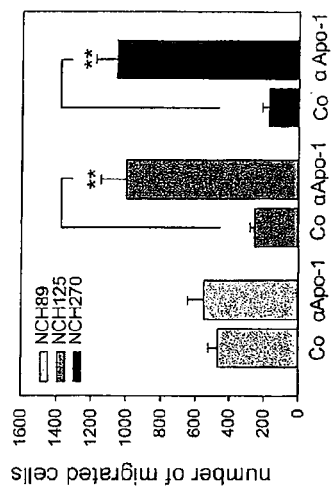
Figure 12:
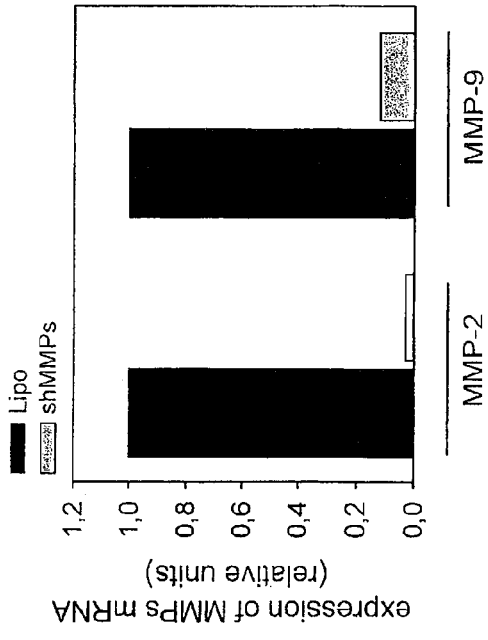
Figure 12:
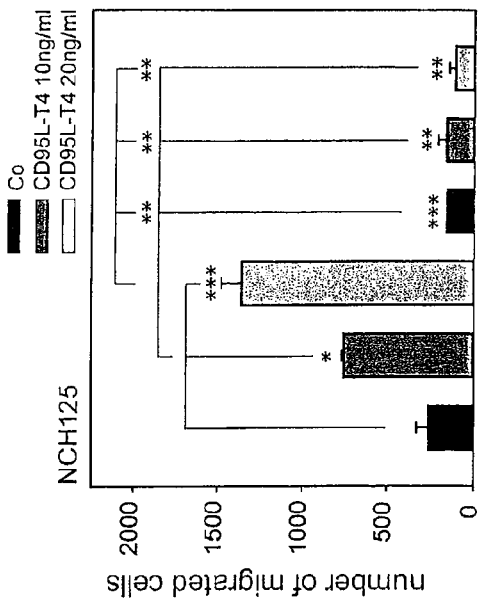

FIG. 12: CD95 triggers invasion of primary apoptosis-resistant glioma cells via MMPs (A) The short term cultured cell lines NCH89, 125 and 270 were incubated with the indicated concentrations of CD95L-T4, Staurosporin (St., 1 µM) or left untreated (Co). After 24 h DNA fragmentation was analyzed by FACS (upper panels). FACS analysis of CD95 surface expression in the NCH89, 125 and 270 (lower panels). (B) NCH cells were treated for 48 h with αApo-1 or left untreated, to detect single cell migration through a Boyden chamber with 8 µm pore size. Results are expressed as mean±S.E., **P<0.01 and are representative of three independent experiments. (C and D) NCH89, 125 and 270 cells were treated with α Apo-1 for 48 h. Expression of MMP-2 (C) and MMP-9 (D) was measured by quantitative real-time PCR. (E) NCH125 cells were transfected with a siRNA pool against MMP-2 and MMP-9 (shM-MPs) or with Lipofectamine alone (Lipo). 48 h after transfection, cells were treated with CD95L-T4, migration was measured in a two dimensional migration assay 48 h later. (F) Expression of MMP-2 and MMP-9 as measured by quantitative-RT-PCR. Results are expressed as mean±S.E., *P<0.05; P<0.001; *P<0.0001 and are representative of at least two independent experiments.

Figure 13:
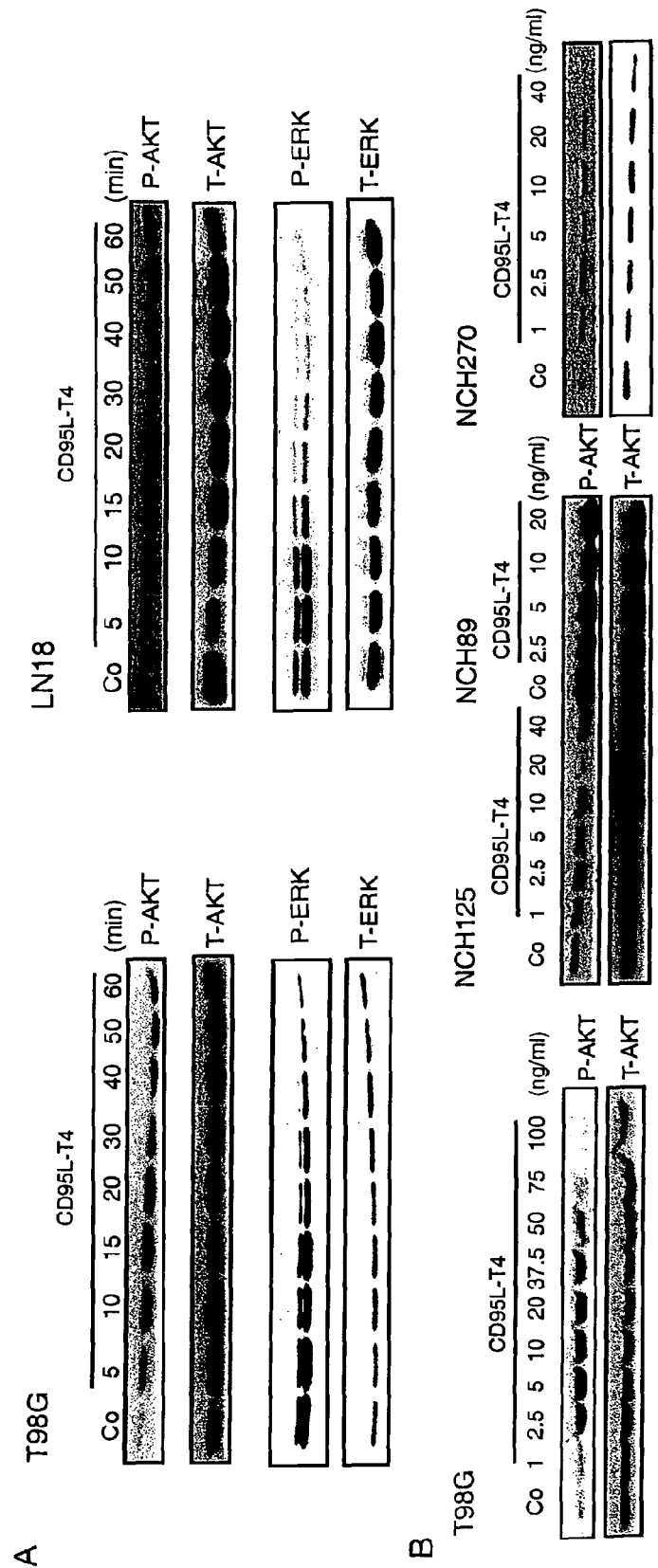
Figure 13:
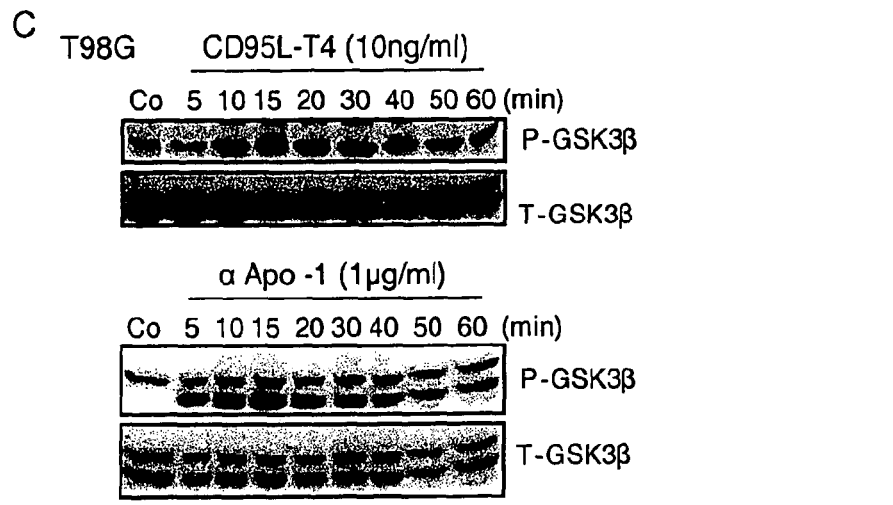
Figure 13:
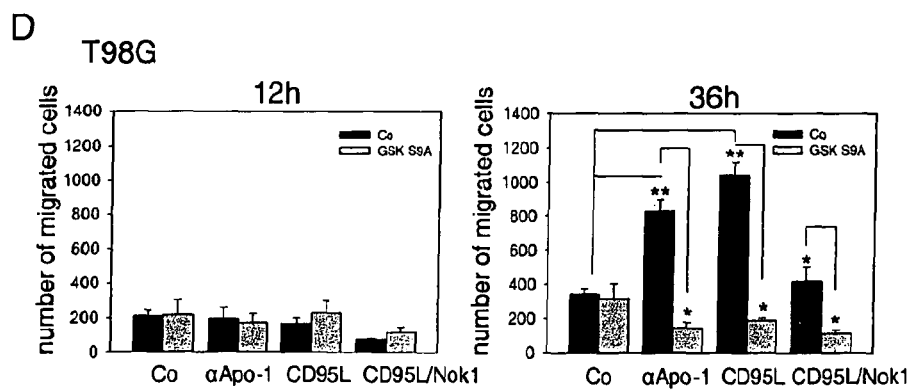
Figure 13:
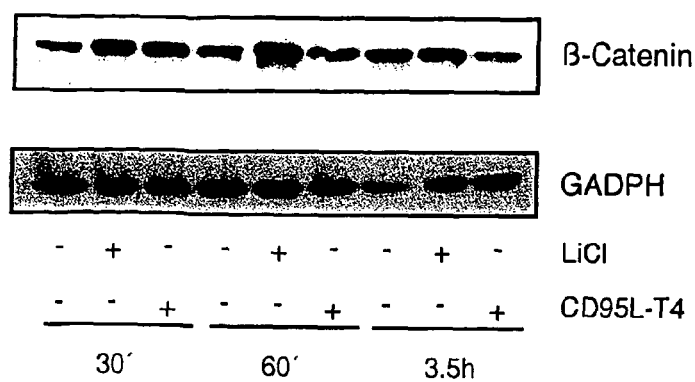
Figure 13:
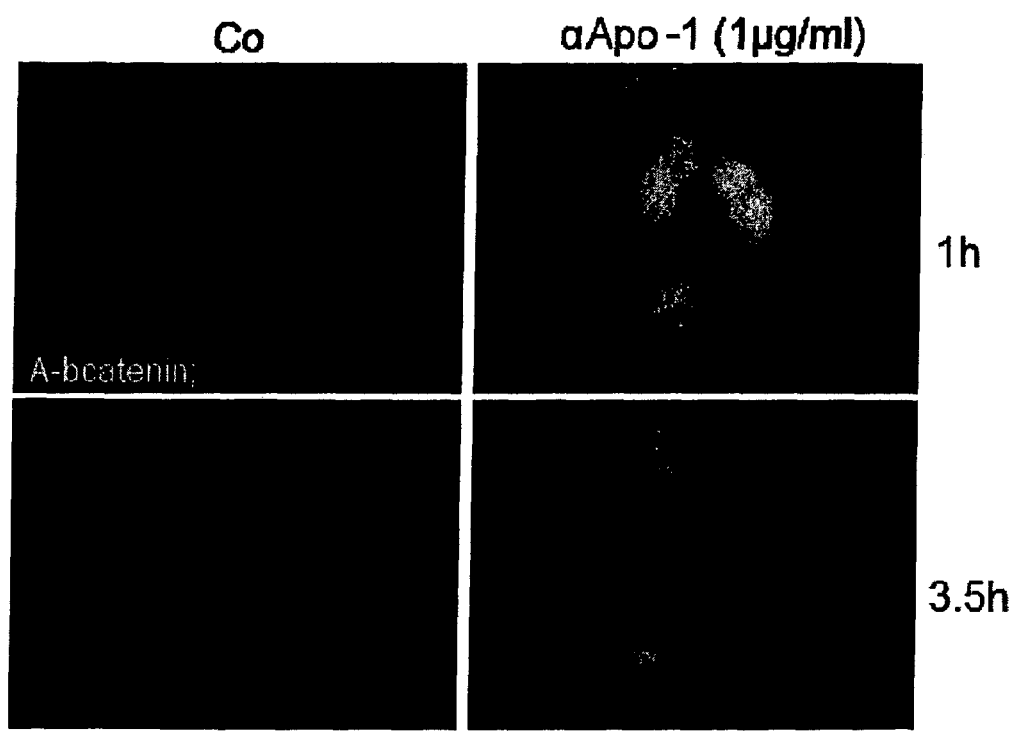
Figure 13:
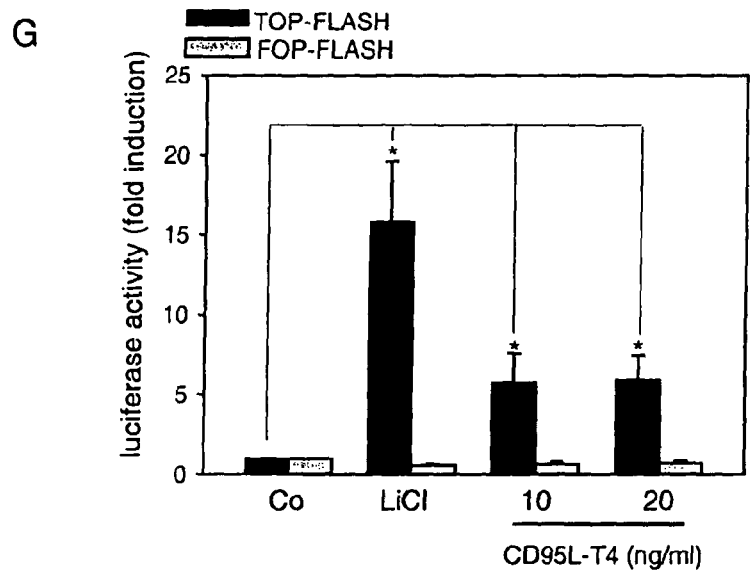
Figure 13:
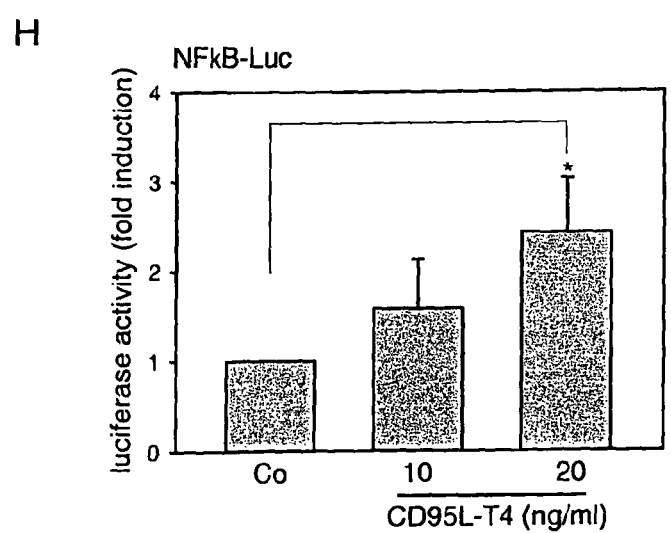

FIG. 13: CD95 induces migration via the PI3K/AKT/GSK3β Pathway (A) Phosphorylation of AKT and ERK is shown in T98G and LN18 cells upon treatment with CD95L-T4 at the indicated time points. (B) In T98G, LN18 and NCH125 and 270 cells, but not in NCH89, phosphorylation of AKT exhibited a concentration-dependent bell-shape after stimulation with CD95L-T4, respectively. (C) In T98G cells treatment with CD95L-T4 (10 ng/ml) and αApo-1 (1 µg/ml) induced GSK3b phosphorylation. Kinetics of GSK3b-inhibition exhibited a bell-shaped curve. (D) T98G cells were infected with an empty lentiviral vector (Co) or a constitutively active GSK3b mutant (GSK S9A). At 36 h GSK S9A infected T98G cells migrated significantly less than their empty vector counterparts upon treatment with αApo-1 or CD95L. A neutralizing antibody to CD95L (Nok1) blocked CD95L-induced migration of vector- and GSK S9A-infected cells. (E) b-Catenin accumulated in the cytosol of T98G cells 30 min after treatment with CD95L-T4 (10 ng/ml). (F) Active b-catenin (green) translocated into the nucleus upon stimulation with αApo-1. DAPI (blue) and P-GSK3β (red) was used to visualize the nuclei and the cytosol, respectively in T98G cells. (G and H) 24 h after transient transfection of T98G with the b-Catenin/TCF transcriptional reporter (TOP-FLASH; G), the control plasmid (FOP-FLASH; G), or the NFkB-reporter construct (NFkB-Luc; H) cells were treated with CD95L-T4 (G and H), LiCl (G) or left untreated (G and H). Luciferase activity was assayed 12 h (G) or 8 h (H) afterwards and normalized to renilla luciferase expression. Results are expressed as mean±S.E., *P<0.05; P<0.001; *P<0.0001 and are representative of two independent experiments. P: phosphorylated, T: total.

Figure 14:
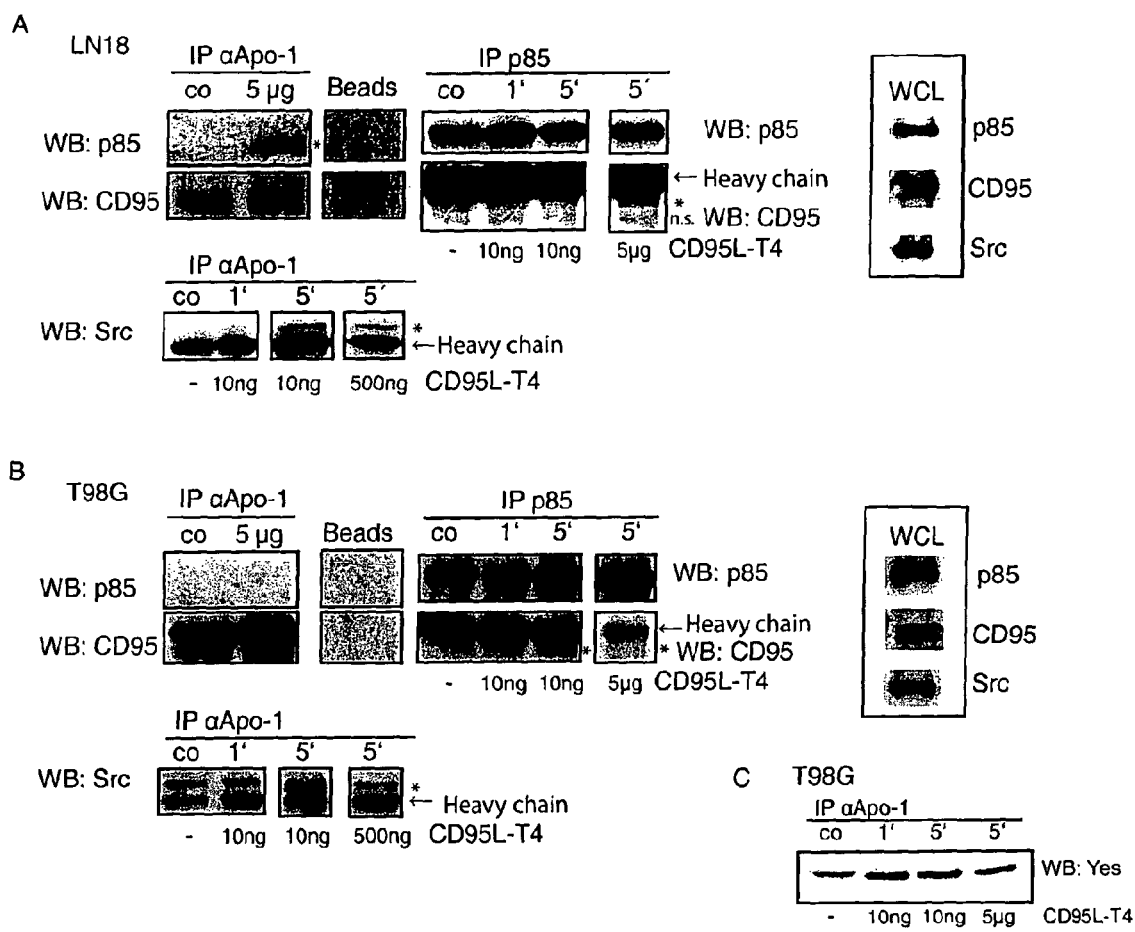
Figure 14:
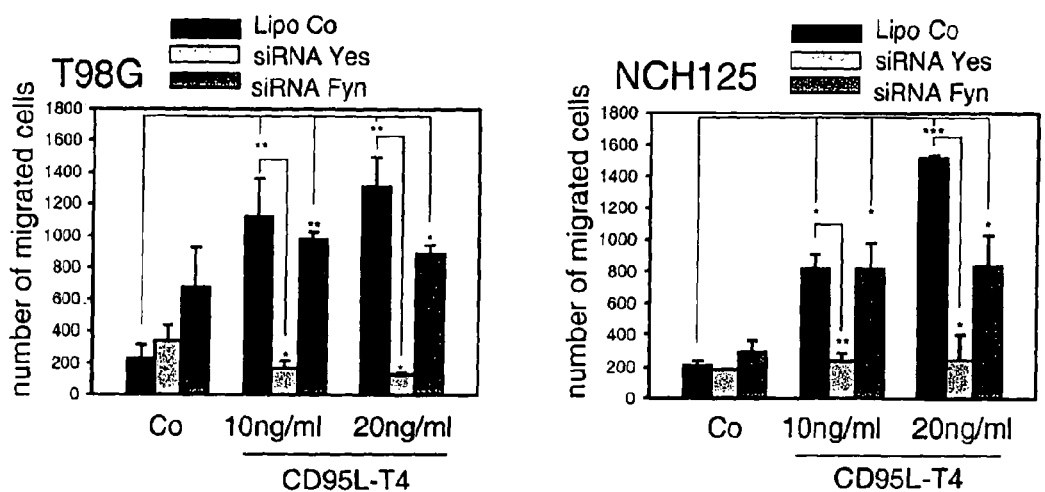
Figure 14:
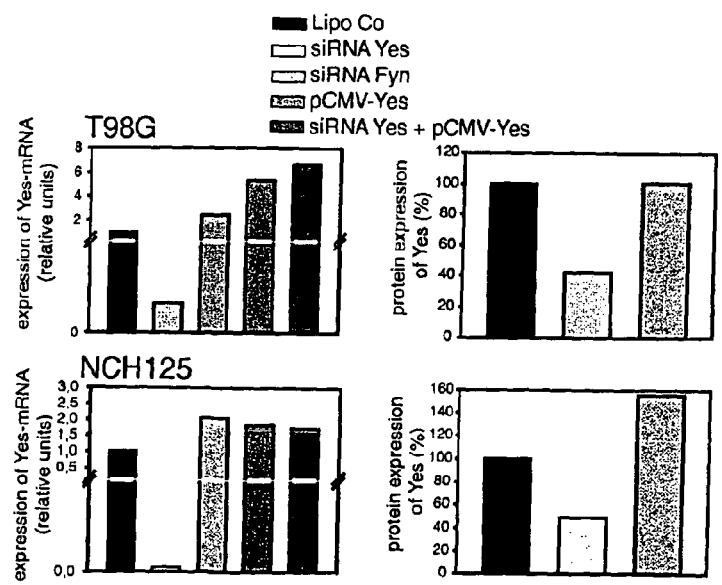
Figure 14:
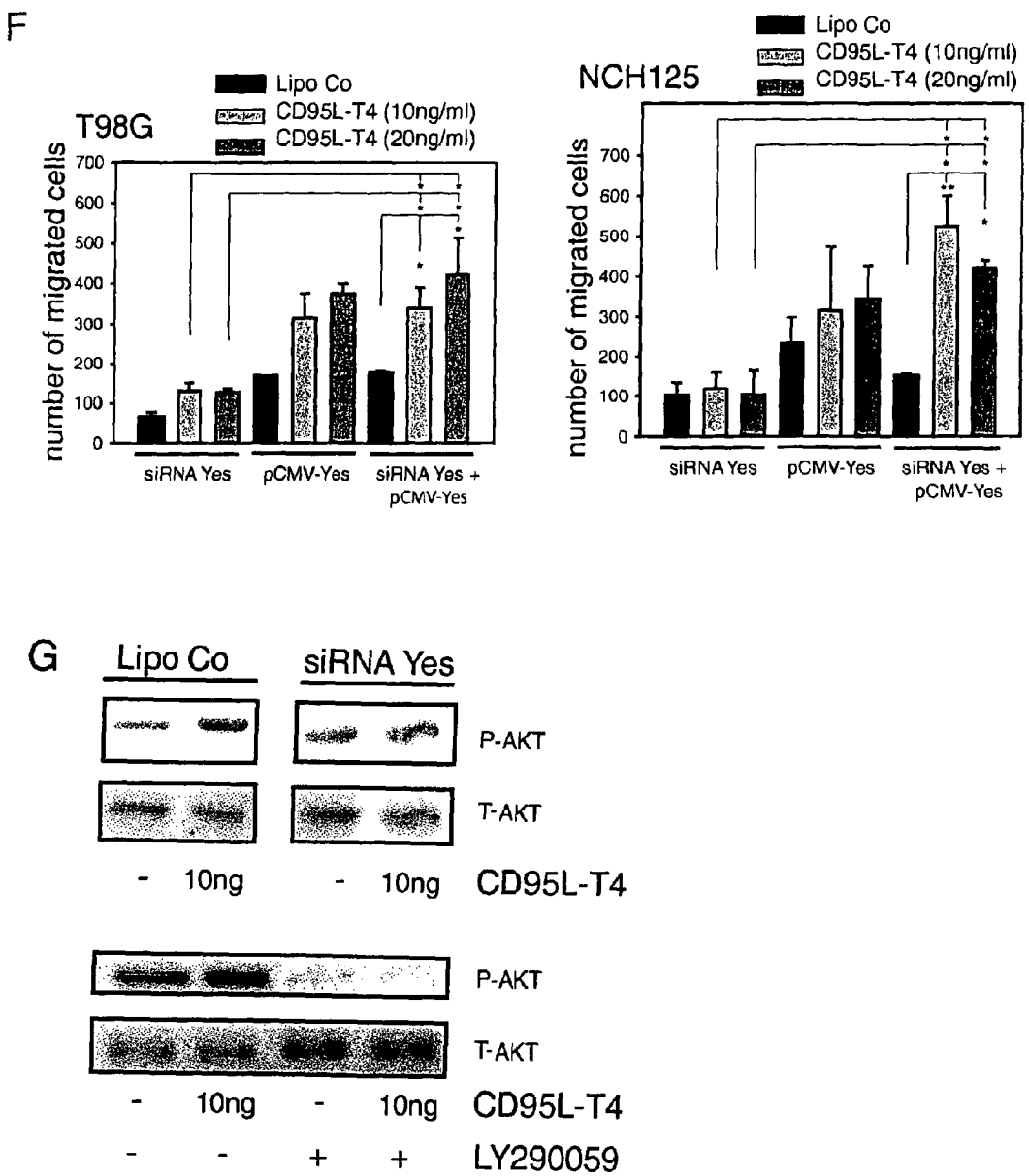

FIG. 14: Src and p85 associate to CD95 to activate AKT (A and B) LN18 and T98G cells were stimulated with CD95L-T4 for the indicated time points and concentrations. On the left panels CD95 was immunoprecipitated and the immunoprecipitates immunoblotted with anti-p85, anti-CD95, and anti-Src antibodies. On the middle panels, p85 was immunoprecipitated and the immunoprecipitates probed with anti-p85 and anti-CD95 antibodies. Protein-A beads are included as a negative control. Whole cellular lysates (WCL) probed with anti-p85, anti-CD95 and anti-Src are shown on the right pannels. (C) T98G cells were treated for the indicated times and concentrations with CD95L-T4. CD95 was immunoprecipitated and immunoprecipitates were immunoblotted with anti-Yes antibody. (D) T98G and NCH125 cells were transfected with siRNA against Yes or Fyn or with Lipofectamine alone (Lipo). 72 h after transfection, cells were treated with CD95L-T4, 24 h afterwards migration was measured in a two dimensional migration assay. (E) Expression of Yes-mRNA as measured by quantitative-RT-PCR and Yes protein levels as assessed by FACS analysis is shown. (F) T98G and NCH125 cells were transfected with siRNA against Yes, a Yes overexpression plasmid (pCMV-Yes) or both. 72 h after transfection, cells were treated with CD95L-T4, 24 h afterwards migration was measured in a two dimensional migration assay. (G) Yes siRNA and the PI3K inhibitor (LY 290059) blocked CD95-induced phosphorylation of AKT. P: phosphorylated; T: total; *: specific band; n.s.: unspecific band.

Figure 15:
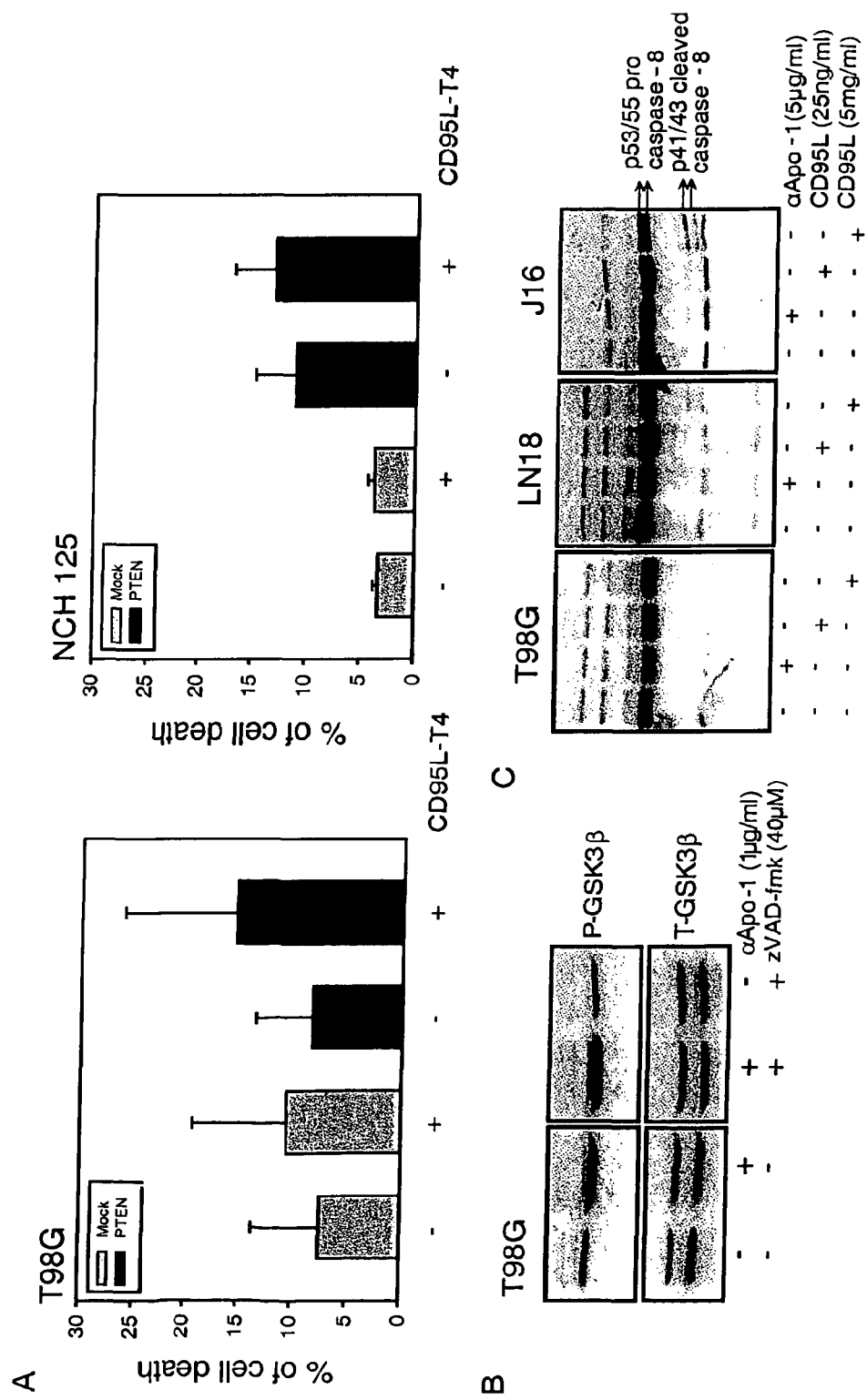
Figure 15:
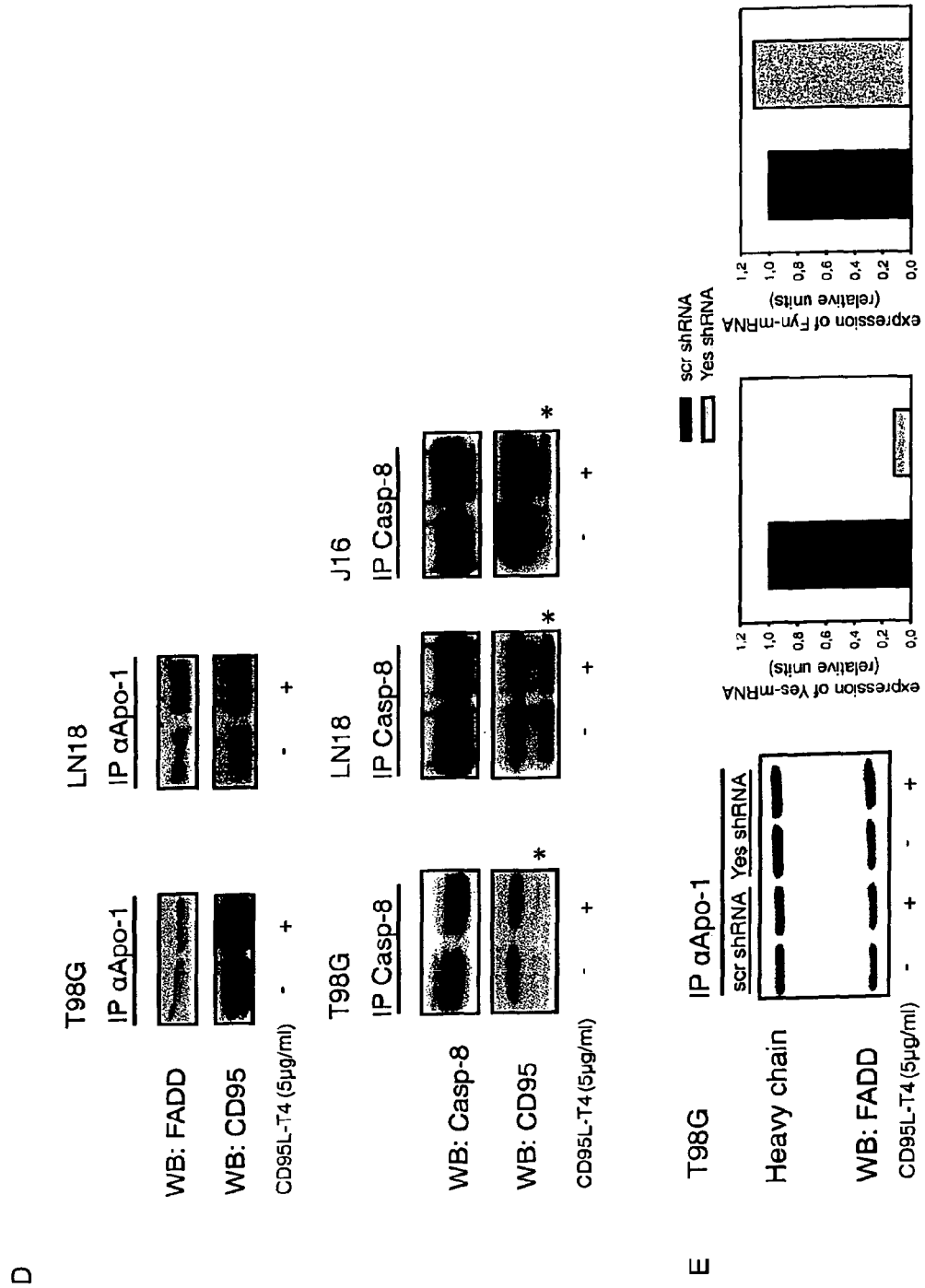
Figure 15:
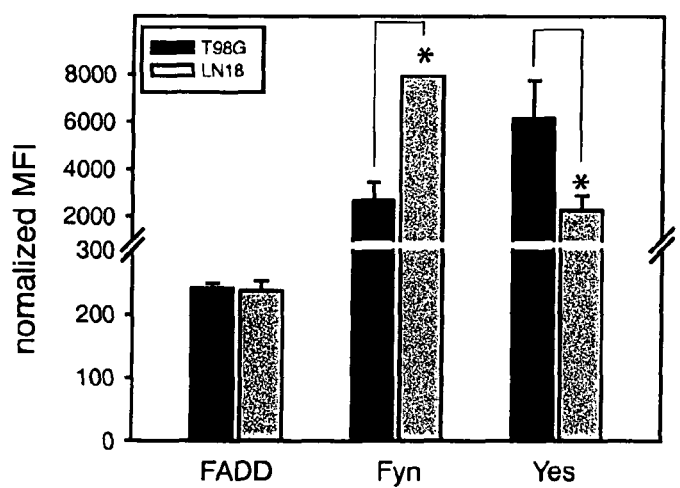
Figure 16:
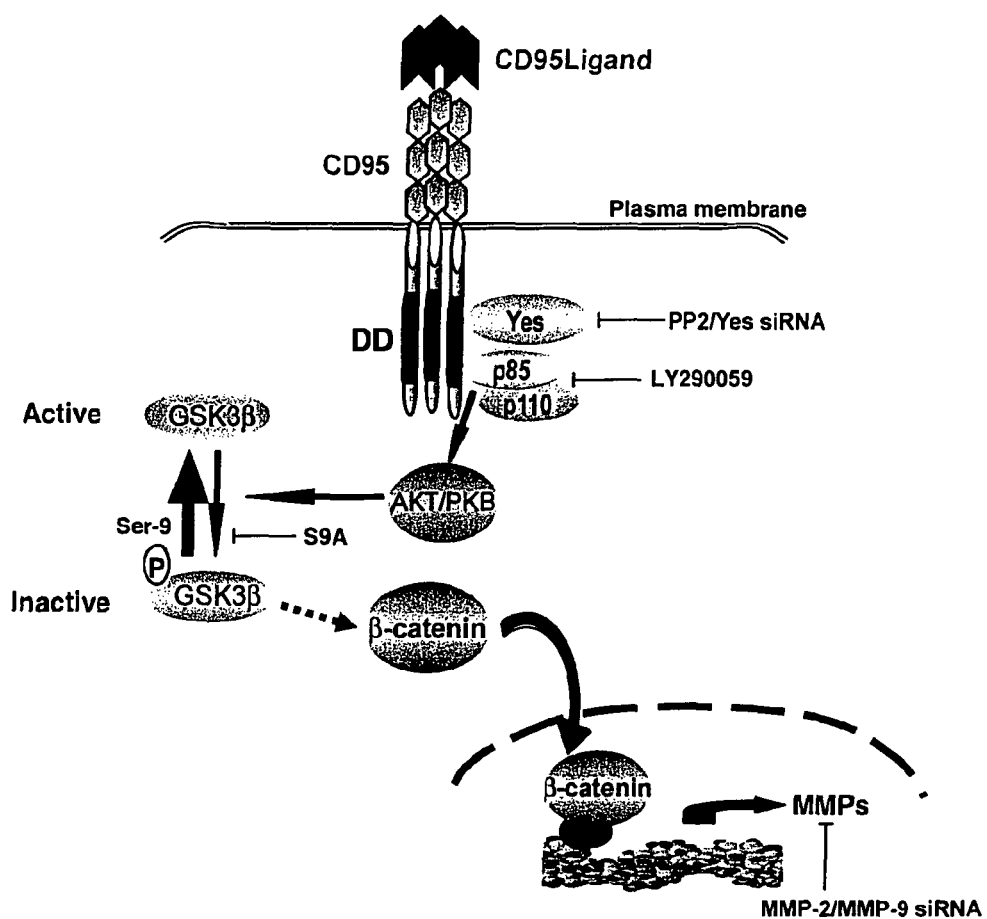

FIG. 15: Inefficient DISC formation in apoptosis resistant glioma cells (A) 48 h after transient transfection of T98G and NCH125 with either a HA-PTEN (PTEN) or the empty vector (Mock), cells were treated with CD95L-T4 (500 ng/ml). To detect cell death in PTEN-overexpressing cells, an intracellular FACS staining against the HA-tag was performed. Thereafter forward side scatter analysis was performed in HA-positive cells. Results are expressed as mean±S.E. and are representative of two independent experiments. (B) T98G cells were treated for 1 h with αApo-1, zVAD-fmk, a combination of zVAD-fmk and αApo-1 or left untreated (Co). Phosphorylation of GSK3β was analyzed by Western Blot. (C) Cleavage of caspase-8 in T98G, LN18 and Jurkat 16 (J16) was detected by Western Blot analysis at 5 min after CD95 stimulation. (D) In T98G and LN18 cells treated with CD95LT4 for 5 min, either CD95 (upper panels) or caspase-8 (lower panels) were immunoprecipitated. The immunoprecipitates were immunoblotted with anti-FADD antibody and anti-CD95 (upper panels) and with anti-CD95 and anti-caspase-8 (lower panels). Jurkat cells were included as a positive control. (E) T98G cells were transfected with either Yes shRNA or a non-targeting shRNA as a negative control. After 72 h, cells were treated with CD95L-T4 or left untreated and immunoprecipitation of CD95 was performed, the immunoprecipitates were then immunoblotted with anti-FADD antibody, the IgG heavy chain serves as loading control. On the right, knockdown efficiency assessed by quantitative-RTPCR is shown. (F) Quantitative expression of FADD, Yes and Fyn in T98G and LN18 cells was measured by FACS analysis. Results are expressed as mean±S.D., *P<0.05 and are representative of three independent experiments. MFI: mean fluorescence intensity P: phosphorylated; T: total FIG. 16: Schematic model for CD95 signalling of invasion in glioblastoma CD95L induces recruitment of the Src family member Yes and the p85 subunit of PI3K (depicted here by its two subunits: p85 and p110) to CD95, thereby activating AKT. Activated AKT phosphorylates and inactivates GSK3b, allowing b-catenin translocation into the nucleus, where it induces transcription of MMPs. This signalling pathway could be blocked by siRNA against Yes, or MMP-2 and -9, the PI3K-specific inhibitor (Ly290059) or by lentiviral infection with a dominant active mutant of GSK3β (S9A).

Figure 17:
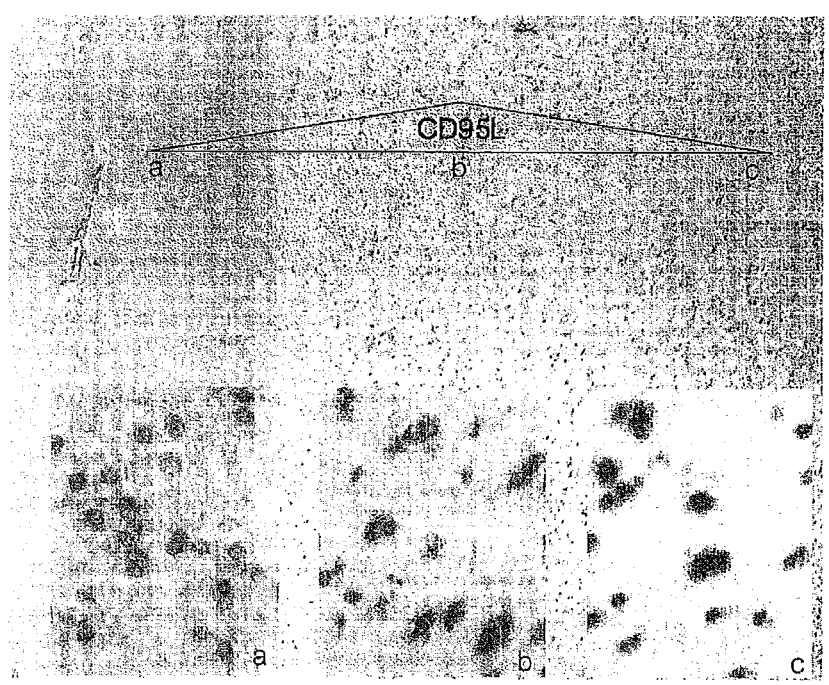
Figure 17:
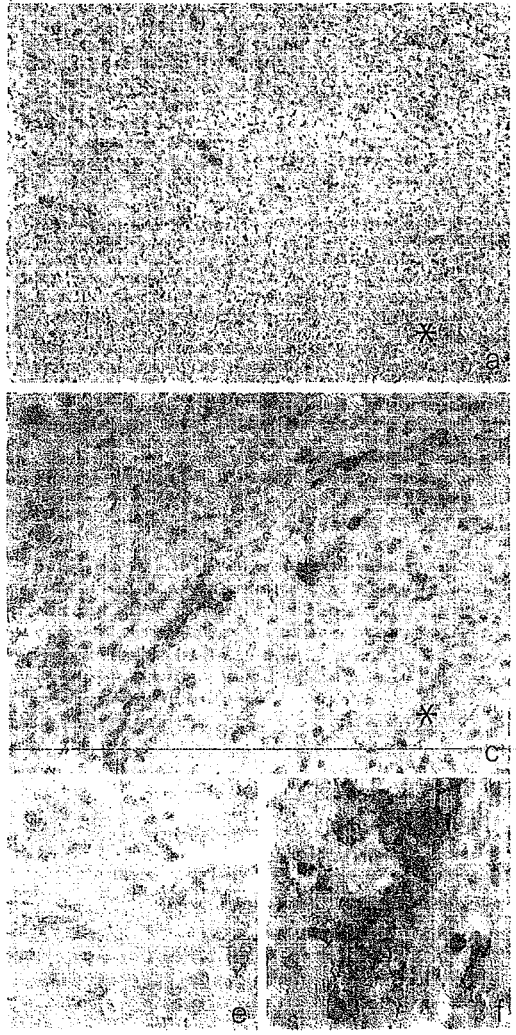
Figure 17:
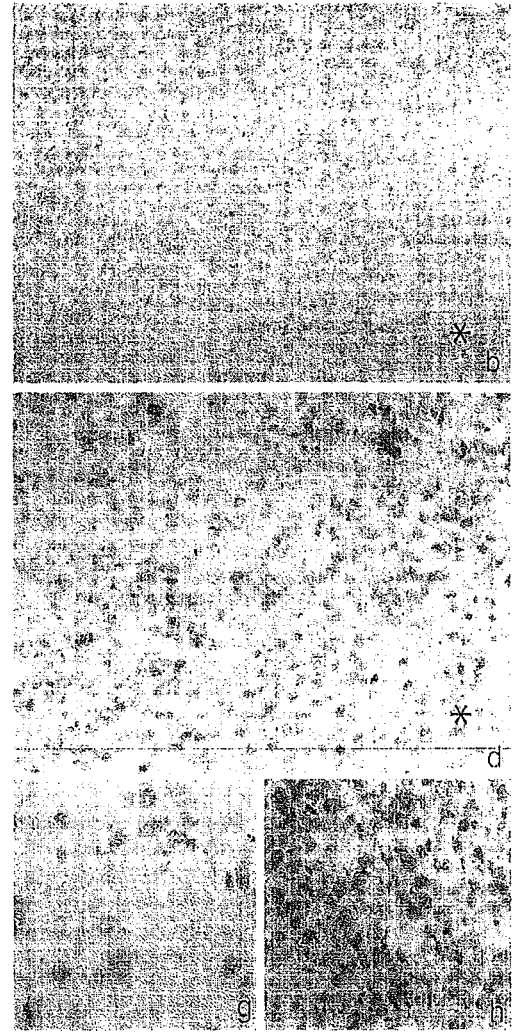

FIG. 17: Expression of CD95L, Yes and Phospho-Src in clinical samples of GBM (A) Representative immunohistochemical staining of CD95L (red) in primary human GBM. Note the increased expression of CD95L at the tumor/host interface (A.b) compared to more solid tumor areas (A.a*) or brain parenchyma (A.c). (B) Immunohistochemical staining of phosphorylated Src family kinases (p-Src; B.a,c,e,f) and Yes (B.b,d,g,h). B.a-d, Overview of tumor infiltration zone, note robust phosphorylation of Src and expression of Yes in zone of tumor/host interaction (to the left) and reduced or no p-Src in solid tumor areas (to the right*). Yes expression was found at the tumor/host interface (B.b, d and g) and in scattered solid tumor areas (B.h). Strong phosphorylation of Src in tumor cells in solid tumor areas (B.f) and infiltration zone (B.e).

Figure 18:
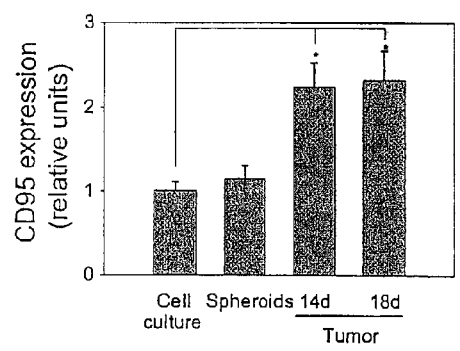
Figure 18:
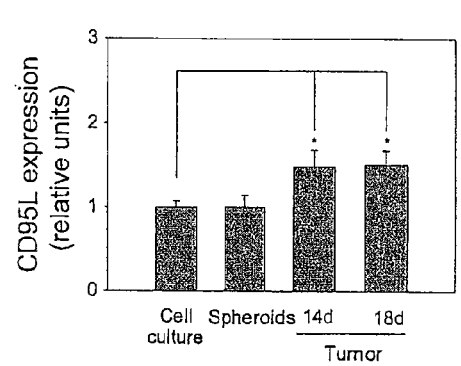
Figure 18:
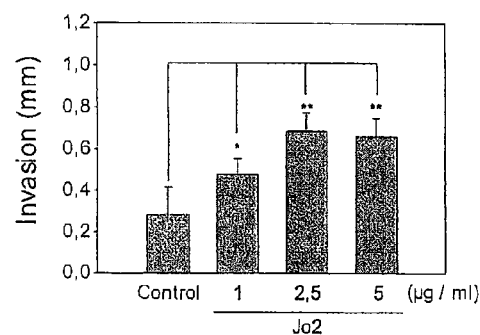
Figure 18:
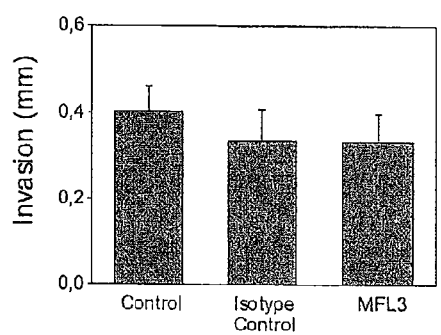

FIG. 18: CD95 and CD95L are upregulated on murine glioma cells in vivo and induce migration (A and B) CD95 and CD95L surface expression on the murine glioma cell line SMA-560 was determined under normal cell culture conditions, after the formation of spheroids or following intracranial implantation. Changes were normalized to cell culture conditions levels. Results represent three independent experiments and are expressed as mean±S.D., *P<0.05. (C) Spheroid cultures were embedded into a collagen matrix and treated with antibodies to CD95 (Jo2), a neutralizing antibody to CD95L (MFL3) or the appropriate isotype control antibody at the indicated concentrations. The migration of cells was monitored over 48 h and the distance of cells to the spheroid's border is depicted (n=10 cells, 3 spheroids per treatment). (D) Experimental scheme. Migration of tumor explants into collagen after treatment with either MFL3 or the appropriate istoype control is depicted as described above (n=10, 3 spheroids per treatment). (E) Representative pictures of GFP-immunostained Isotype- or MFL3-treated SMA-tumors. The tumor-bearing (ipsilateral) and contralateral hemisphere are shown. Numbers of SMA-560 cells (GFP-positive) in the contralateral hemisphere of Vm/Dk mice either treated with MFL3 or the isotype control antibody were counted and normalized to tumor area. Shown results are representative of two independent experiments and expressed as mean±S.D., *P<0.05, **P<0.001. Scale bar: 100 μm FIG. 19: Generation of CD95L-T4

Localization of the N- and C-terminal amino acids within the TRAIL-RBD, forming an antiparallel.beta.(A) Enlargement of the TRAIL-RBD-structure (N-ter-minus: green; C-terminus: red). (B) Position of the N- and C-terminus within the structure of the TRAIL-RBD. Upper row: side view of the central axis of the TRAIL-RBD. Lower row: top view of the central axis of the TRAIL-RBD. Left to right: mono-, di- and trimer. (C) CD95L-T4 amino acid sequence (SEQ ID NO:26). The signal peptide is underlined (Met1-Gly20). The N-terminal (green arrow) and C-terminal amino acids (red arrow) of the CD95L-RBD are proposed to form an antiparallel.beta.-strand. The T4-Foldon sequence is printed in blue (italics). (D) Model of TRAIL-T4-DR5 complex. Upper Row: side view of TRAIL-DR5 co-complex with the T4-Foldon (light blue) positioned above the TRAIL-RBD (dark blue). The DR5 chains are colored in dark red. The N-terminal amino acids of the TRAIL-RBD and the T4-Foldon are colored in green; the C-terminal amino acids are colored in red. Upper row: side view of the central axis of the TRAIL-RBD. Lower row: top view of the central axis of the TRAIL-RBD. Left: ribbon model. Right: surface model. (E) Affinity purification of CD95L-T4. CD95L-T4 containing supernatant from transiently transfected Hek293T cells was affinity purified using Streptactin Sepharose. Proteins specifically eluted by desthiobiotin were subsequently analyzed by SDS-PAGE and silver staining. The position of CD95L-T4 is indicated by an arrow. CD95L-T4 shows an apparent molecular weight of approximately 30 kDa. The difference towards the theoretical molecular weight of 23 kDa is probably due to glycosylation. (F) Analysis of purified CD95L-T4 by size exclusion chromatography (SEC). For determination of the native apparent molecular weight CD95L-T4 was separated by SEC using a Superdex 200 column. The graph shows the elution profile (OD 280 nm) of Streptactin-purified CD95L-T4. Fraction B3-C2 collected from SEC (see B) was analyzed by SDS-PAGE and silver staining. (G) Determination of the apparent molecular weight. Calibration curve of the Superdex 200 column based on retention volumes of the indicated proteins. The apparent native molecular weight of CD95L-T4 is 90.3 kDa, indicating a stable trimeric protein. AP-G101 antagonizes the apoptosis inducing activity of CD95L-T4 in Jurkat cells. (H) CD95L-T4 induces apoptosis in Jurkat cells in a dose dependent manner, as shown by an increase in Caspase 3/7 activity.

Addition of 10 µg/ml anti-StrepMAB, an anti-body crosslinking the CD95L-T4 trimers, augments the extent of apoptosis. (I) The apoptosis inducing activity of 250 ng/ml CD95L-T4 in Jurkat cells is antagonized by APG101 in a dose dependent manner.

Figure 20:
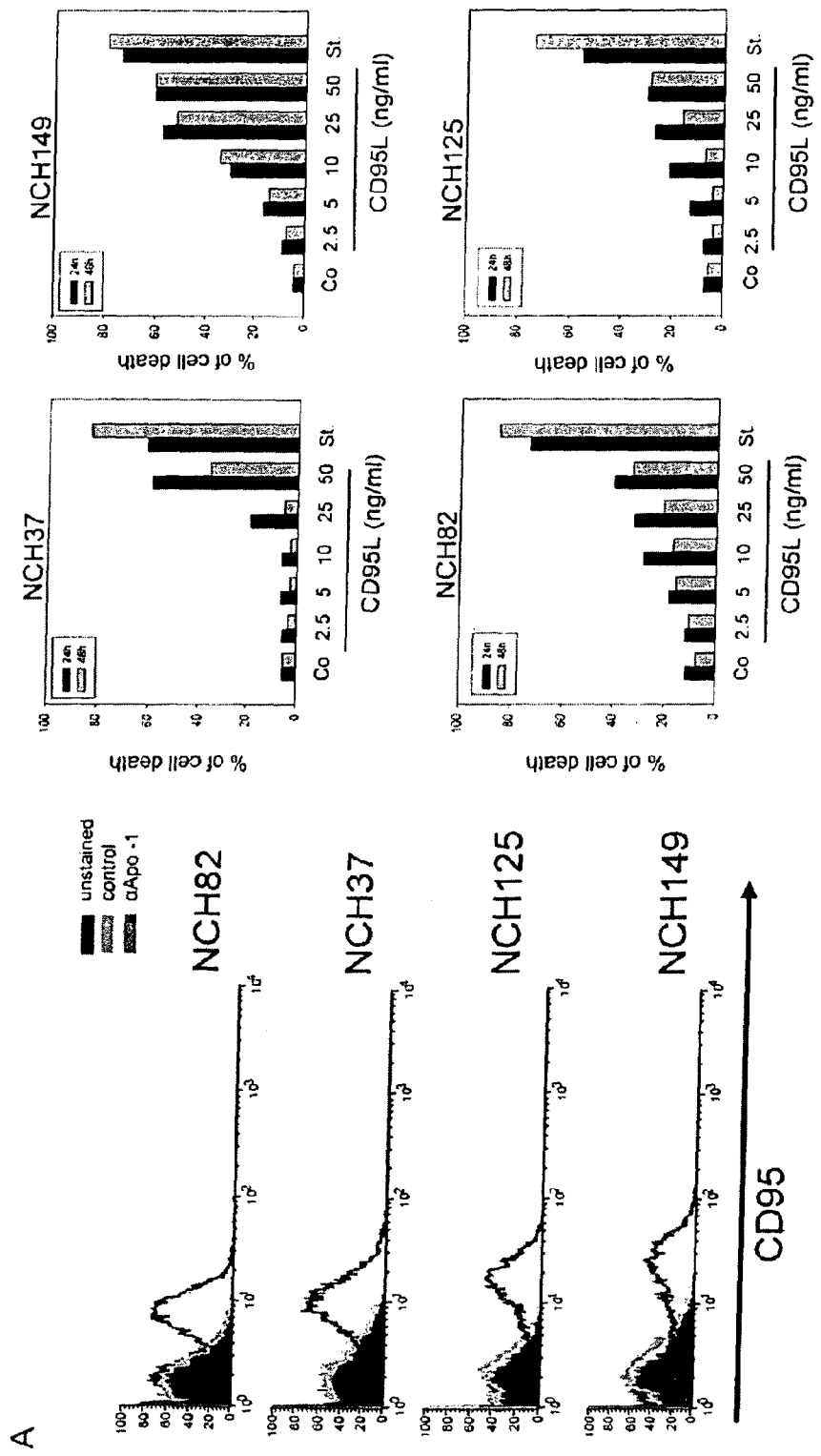
Figure 20:
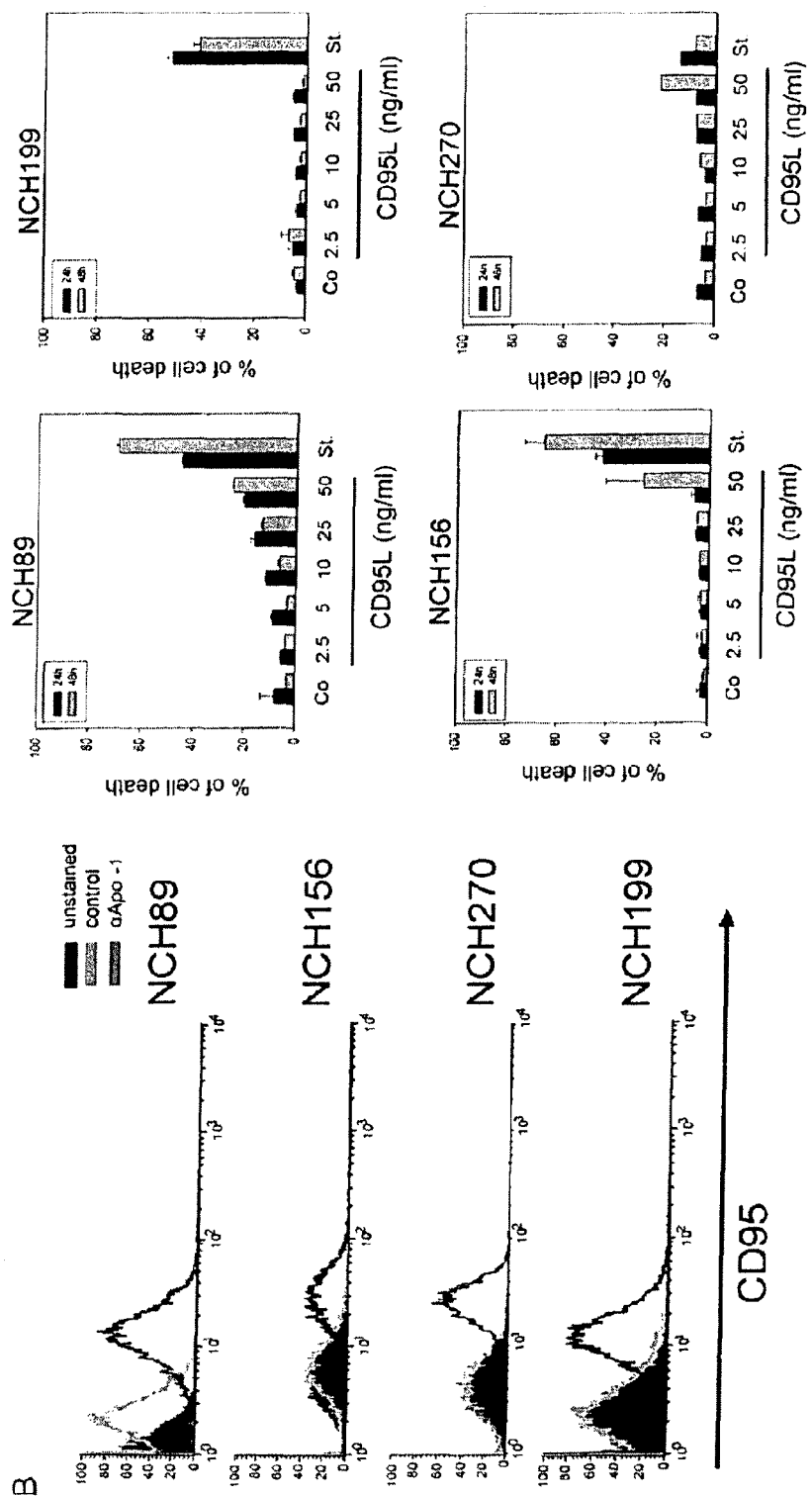
Figure 20:
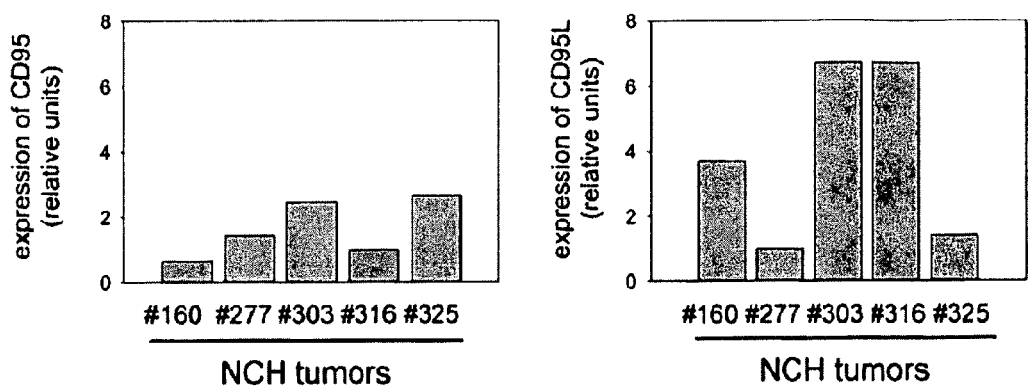

FIG. 20: CD95/CD95L system and sensitivity to apoptosis in primary glioblastomas (A and B) FACS analysis of CD95 surface expression in primary glioblastoma cell lines (NCH82, 37, 125, 149, 89, 156, 270 and 199) with high passages ($\geq$50). For DNA fragmentation cells were treated with indicated doses of CD95L (ng/ml) for 24 h and 48 h and analyzed by FACS. Results are given as mean±S.D. and are representative of two independent experiments. (C) mRNA levels of CD95 and CD95L in human tumor tissue, determined by quantitative real-time PCR. Results are representative of two independent experiments.

Figure 21:
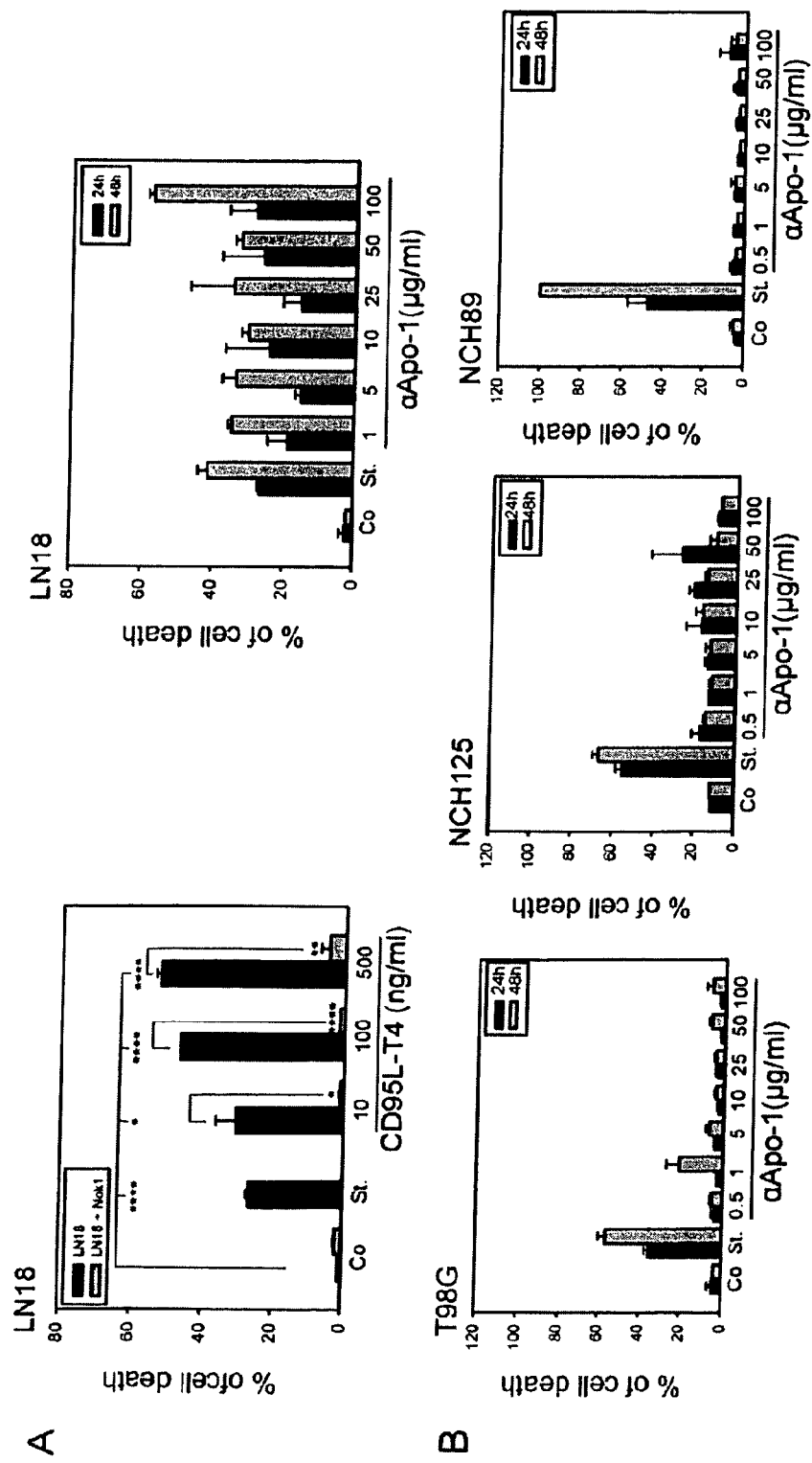
Figure 21:
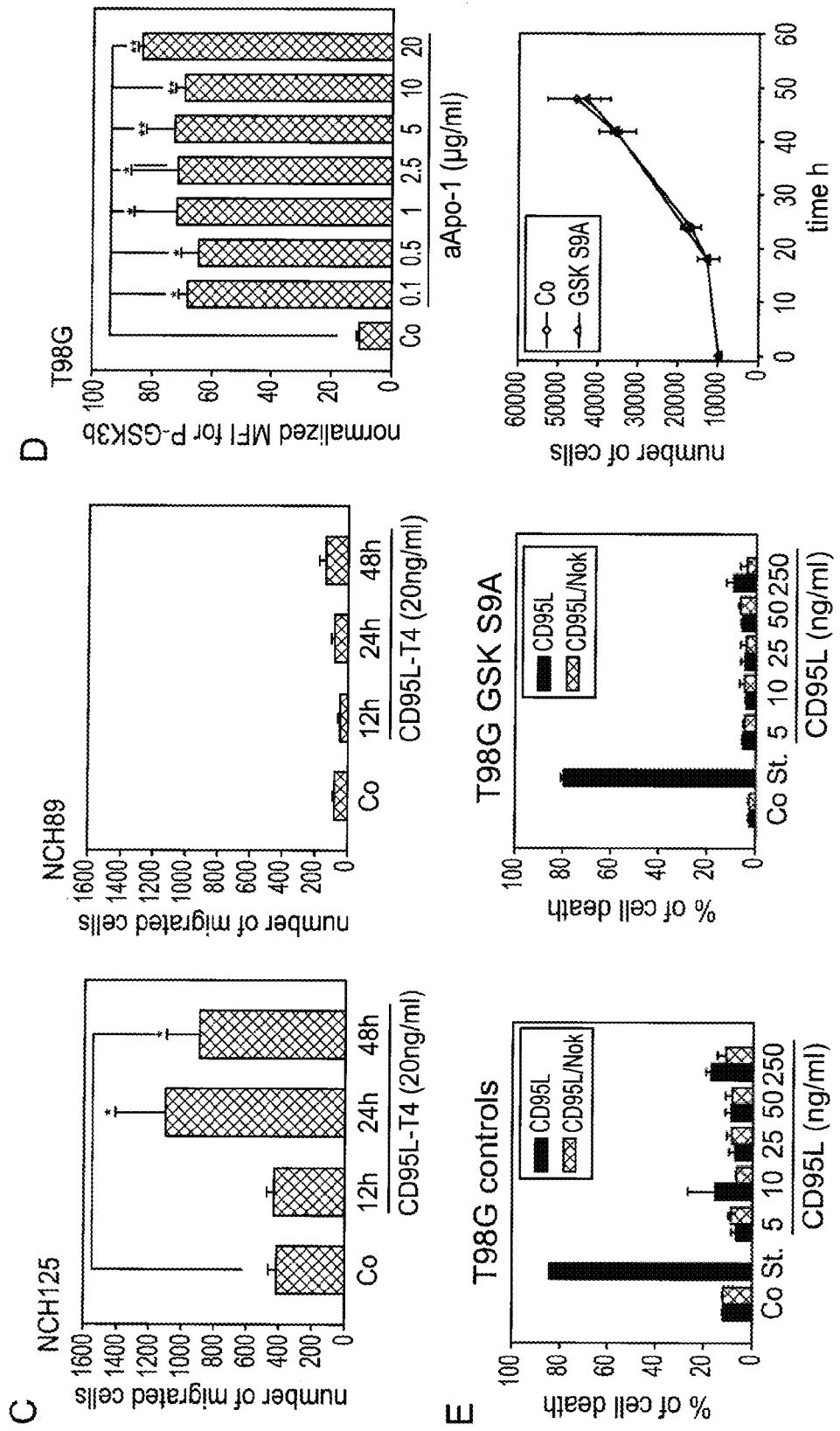
Figure 21:

FIG. 21: Modulators of CD95-mediated PI3K activation (A) LN18 cells were incubated with the indicated concentrations of CD95L-T4 with or without a neutralizing antibody to CD95L (Nok1), αAPO-1, Staurosporin (St., 1 µM), or left untreated (Co). After 24 h and 48 h DNA fragmentation was analyzed by FACS (B) T98G and the short term cultured cell lines, NCH89 and 125 were incubated with the indicated concentrations of αApo-1, Staurosporin (St., 1 µM), or left untreated (Co). After 24 h and 48 h DNA fragmentation was analyzed by FACS. (C) NCH125 and NCH270 cells were treated for 48 h with CD95L-T4 or left untreated, to detect single cell migration through a Boyden chamber with 8 µm pore size. (D) GSK phosphorylation in T98G cells measured by intracellular FACS staining. (E) GSK S9A-infected T98G cells and the respective controls were stimulated with the indicated doses of CD95L (ng/ml) for 48 h and DNA fragmentation was analyzed by FACS. Growth curves of T98G Co and GSK S9A are shown. (F) T98G and NCH125 cells were transfected with siRNA against Yes or Fyn or with Lipofectamine alone (Lipo). Expression of Fyn as measured by quantitative-RT-PCR is shown. Results are expressed as mean±S.E., *$P<0.05$; $P<0.001$; *$P<0.0001$.

FIG. 22: Table 1

DETAILED DESCRIPTION

It is generally appreciated that the CD95/CD95L complex induces apoptosis [18]. However, there is growing evidence that CD95 can mediate apoptosis-independent processes such as proliferation, angiogenesis, fibrosis, and inflammation [19,20]. Over-expression of CD95 in Lewis lung carcinoma cells resulted in a survival advantage of tumor cells in vivo [21]. Along the same lines, triggering of CD95 has been reported to drive cell cycle progression in glioma cells [22]. In malignant astrocytoma, CD95 ligation promoted expression of pro-inflammatory chemokines and angiogenesis [23-25]. Here we report that triggering of CD95 in glioblastomas initiates a cascade of signaling events ultimately leading to increased invasiveness. CD95-induced migration was first observed in cultured renal tubular cells [26] and has recently been reported for ovary, breast, lung and kidney tumor cells [13]. In the latter study, a serum-gradient was added to the CD95 stimulus in order to instigate and direct cell migration [13]. Glioblastoma cells, on the contrary, are characterized by their invasion-prone phenotype and do migrate in the absence of an additional stimulus.

Thus, the present invention concerns methods for blocking in vitro, ex-vivo and in vivo the highly invasive glioblastoma behaviour by the sole neutralization of CD95 activity. The present invention contemplates any method or mechanism for neutralizing or otherwise blocking CD95 activity, such as by using an antibody that binds to it or by downregulating or inhibiting CD95 gene expression or CD95 mRNA transcript translation.

To invade and spread into the surrounding normal brain, tumor cells need to digest components of the extracellular matrix, including fibronectin, laminin, and type IV collagen. The best characterized family of ECM-degrading enzymes is the MMP family. MMP9deficient glioblastomas are less invasive in vitro and in vivo [27]. Glioblastomas produce significantly higher levels of MMP9 than do lower-grade gliomas and normal brain tissue [27]. Levels of MMP9 increased during the growth of glioblastoma cells that had been implanted intracranially in nude mice [28]. These proteases have also a role in establishing and maintaining a microenvironment that facilitates tumor-cell survival. Accordingly, MMPs regulate tumor angiogenesis and inhibition of MMP9 reduced capillary-like structures in mixed-cultures of endothelial and glioma cells [27]. The same features apply to CD95L expression: (i) levels positively correlate with the degree of malignancy [23,29,30]; (ii) levels increase after intracranial inoculation; (iii) in human specimens of GBM one of its preferential localization is at the tumor vessels.

Here the present inventions demonstrates that triggering of CD95 increases mRNA expression of MMP9 and MMP2 in established glioblastoma cell lines and primary cultures and knockdown of MMP2 and MMP2 blocks CD95-induced migration.

The promoter region of MMP9 contains putative binding sites for AP-1, NFκB, Sp1 and AP-2 [31]. The AP-1 transcription complex plays an essential role in stimulating transcription of MMP9 [31,32]. AP-1 driven transcription of MMP9 in glioblastoma cells has been previously reported to be downstream of the PI3K/ILK/GSK pathway [9,10] or instead may require ERK and JNK activity [33].

c-Jun, a putative component of the AP-1 transcription complex, has been identified as one of the most highly induced TCF/β-catenin target genes [36,37]. Inhibition of GSK3β, as reported here, allows unphosphorylated β-catenin to accumulate and translocate into the nucleus, where it functions as a cofactor for transcription factors of the TCF/Lef family [35]. In addition, activity of NFκB was concomitantly observed. Since CD95L-T4 decreases ERK activity, we believe that in T98G cells AKT regulates NFκB activity through phosphorylation/activation of the IKK kinase, which in turn phosphorylates IκB and allows the release of activated NFκB [66]. Alternatively, IκB can transactivate the p65 subunit [64]. In contrast, the induction of motility and invasiveness previously reported for tumor cell lines of endodermal or mesodermal origin involves ERK, NFκB and Caspase-8 activity [13].

In contrast, treatment of glioblastoma cells with CD95L did neither trigger ERK activation nor caspase-8 cleavage. CD95-mediated invasion of glioblastoma cells could not be blocked by an ERK or a general caspase inhibitor. Instead, in these cells from neuroectodermal origin invasiveness was regulated via the PI3K/ILK/GSK pathway, as it could be blocked by a PI3K-, an ILK-inhibitor and by a dominant-active form of GSK3β. PI3K activity is also required for association of the epidermal growth factor receptor (EGFR) which then increases expression of MMP9 via ERK [34]. Thus, CD95-mediated activity of PI3K facilitates an additional increase in MMP9 activity by EGFR. Thus, activation of CD95 induces migration/invasion through the PI3K/AKT/GSK3β/β-catenin/MMP and/or the PI3K/AKT/NFκB/MMP pathway.

GKS3β is found in a multiprotein complex with the adenomatous polyposis colon (APC) tumor suppressor protein, axin and β-catenin. In unstimulated cells, GSK3β phosphorylates β-catenin, marking it for ubiquitination and subsequent degradation[35]. Inhibition of GSK3β destabilizes this degradation complex, allowing unphosphorylated β-catenin to accumulate and translocate to the nucleus where it functions as a cofactor for transcription factors of the T-cell factor/lymphoid enhancing factor (TCF/LEF) family[35]. C-Jun, a putative component of the AP-1 transcription complex, has been identified as one of the most highly induced TCF/β-catenin target genes[36,37].

Phosphorylated c-Jun has recently been found to interact with TCF4 and, thereby, regulate intestinal tumorigenesis by integrating the JNK and GSK pathways. We hypothesize that high basal ERK and JNK activities together with GSK3β inhibition determine the tumorigenic activity of CD95. In this respect, the present inventors found that high basal levels of phosphorylated GSK3β positively correlate with the ability of CD95 to increase migration (data not shown) while the levels of CD95-surface expression did not have any influence. Accordingly, malignant gliomas exhibit greater free pools of unphosphorylated β-catenin than less malignant ones (own unpublished data).

In the past, several reports have pointed out an important role for tyrosine phosphorylation in CD95-induced signalling[56,59]. These preliminary reports, however, suggested that CD95-induced tyrosine phosphorylation is a prerequisite for CD95-mediated apoptosis[56, 60, 69]. Along this line, the phosphatases SHP-1, SHP-2 and SHIP were found to associate with CD95 to counteract survival factors-initiated pathways[54]. Just recently, Src-induced tyrosine phosphorylation of caspase-8 was found to impair CD95-induced apoptosis[53]. We now describe a novel association of the Sr-cfamily member Yes and p85 with CD95. TRANCE, another TNF family member, activates PI3K through a signalling complex involving c-Src and TRAF6[71]. Inhibition of Fyn, another Src family member, decreased CD95-induced migration of glioblastoma cells, although not significantly. This can be explained by the fact that Fyn is involved in EGFR-mediated signalling in neural cells and EGFR is a very important receptor for glioma invasion that has been found in association with CD95. Thus inhibition of CD95-mediated signalling might affect EGFR mediated signalling and vice versa. Whether another adaptor molecule is still missing in CD95's PI3K-activation complex (PAC) remains subject of future studies. Alternatively, Yes and p85 might directly interact with CD95 through the previously identified phosphotyrosine containing motif in the DD of CD95[54]. Accordingly, in T98G cells, knockdown of Yes enabled CD95L-T4-induced recruitment of FADD to CD95 indicating that Yes and FADD might compete for binding to CD95. Along this line, analysis of Yes expression levels revealed a much higher expression in T98G than in LN18 cells. Most importantly, expression of Yes and phosphorylation of Src family kinases was consistently found at the site of tumor/host interaction in clinical samples of GBM, indicating its involvement in tumor invasion.

Barnhart et al. (2004)[13] previously showed that exogenous CD95L induces migration of tumor cells from endodermal origin in vitro. In these cells CD95L induces migration via caspase-8 and ERK[13]. These authors speculate that CD95L might be involved in the tumor's escape to chemo- and radio-therapy, since both treatments increase expression of CD95L. In our study we found that CD95L also induces migration of GBM cells. Beyond this, the present study represents a significant conceptual advance in the field of tumor biology since it shows for the first time that: (i) the sole interaction of tumor cells with the surrounding parenchyma induces expression of CD95L in tumor and host cells; (ii) in GBM cells CD95L signals invasion via Yes/PI3K/MMPs and not via caspase-8/ERK as it is the case in tumor cells of endodermal origin; (iii) neutralization of CD95 activity blocks the basal migration of GBM cells in vivo in a mouse syngenic model of GBM that mimics the clinical situation. In addition, this study shows that the molecular stoichiometry of the PI3K signalling components seems to determine the cellular response to CD95.

In summary, the present data indicate that WHO Grade IV tumors are resistant to CD95-induced apoptosis but increased their invasion capacity upon stimulation of CD95.

Despite the known clinical resistance to irradiation of GBM, the current therapy for GBM encompasses surgery followed by irradiation and adjuvant chemotherapy. The standard irradiation regimen uses an optimal dose of 60 Gy usually given in daily fractions of 1.8 to 2 Gy for approximately 6 weeks with concomitant focally directed radiotherapy. The target area is the enhanced area typically seen on MRI with an additional 2 to 3 cm margin[38]. This regimen has been developed based on the knowledge that the principal treatment failure in malignant gliomas is tumor recurrence within 2 cm of the original tumor site, occurring in approximately 80% to 90% of cases[38]. Radiation induces damage by direct interaction with the cellular target or indirectly through interaction with other atoms or molecules (e.g., water) within the cell to produce free radicals that secondarily affect critical structures. In addition, irradiation has been shown to increase expression of death receptors and death ligands, which in some cases kill the cell via apoptosis[3]. The present invention confirms that irradiation of glioblastoma cells greatly increases the levels of CD95 and CD95L. Nevertheless, cells remain resistant to radiation-induced damage. Instead, we show that irradiated cells exhibit a higher CD95Ldependent migration potential. Even cells that did not increasingly migrate after the sole stimulation of CD95 did so after irradiation. Thus, an additional irradiation-mediated increase of CD95 levels or possible changes in the overall kinase activity might render cells sensitive to CD95-induced migration. Along this line, therapeutic X-irradiation is the only environmental factor unequivocally linked to a higher risk of brain tumors, including glioma, often within ten years after therapy[39]. Most importantly, in contrast to the original tumors where CD95 and CD95L were barely expressed within the tumor, in recurrent GBM expression of CD95 and CD95L dramatically increased. In line with the in vitro data, we did not detect apoptotic cells near CD95L-positive cells, but instead an increased expression of MMP9.

Current experimental strategies to block glioblastoma invasion focus on inhibition of MMP activity by expression of the natural inhibitors TIMP2 and TIMP4 or rely on direct gene targeting of MMP mRNA by antisense strategies. However, while TIMP2 decreases angiogenesis and invasion it also protects tumor cells from apoptosis[40]. Other strategies to inhibit MMP production employs targeting the signal-transduction pathways leading to their expression which are similarly not only involved in the induction of tumor invasion but also in some basic neural functions, thus, making these stratigies less attractive for clinical application.

By contrast, while CD95 activity is required for neurite remodeling during embryonic brain development[41] and for the clearance of damaged brain cells in the diseased brain [42-45] no CD95 activity is detectable in the adult healthy brain. brain. Thus, targeting CD95 should have fewer side effects than other migration-inducing factors that are normally involved in normal brain function.

Thus, CD95 appears as a very potent and attractive target for the front-line therapy of human glioblastoma.

EXAMPLES

Example 1

Reagents and General Procedures

Following antibodies were used: anti human-CD95L G247-4 (1:200), the neutralizing antibody to CD95L (Nok1), the anti murine-CD95 (Jo2), the anti murine-CD95L (MFL3) and the appropriate isotype control, a hamster IgG1, λ1, were purchased from Becton Dickinson. Antibodies against CD95 (α-Apo-1) was generated as described previously[46], phosphorylated GSK3β (P-Ser9-GSK3β, 1:1000), phosphorylated AKT (P-Ser473-KT, 1:1000), total AKT (T-AKT, 1:1000), Src family kinases (Src, 1:1000), phosphorylated Src (P-Tyr416 1:50) and total β-Catenin (1:1000) were purchased from New England Biolabs. Antibodies against CD95 (CD95, 1:1000), total GSK3β (T-GSK3β, 1:1000), phosphorylated ERK1/2 (P-ERK, 1:1000), total Yes (Yes, 1:1000 or 1:200), total Fyn (1:200) and total ERK (T-ERK, 1:1000) were purchased from Santa Cruz. Anti-GFAP (1:200) was purchased from Chemicon, anti-PI3K (p85 N-SH2 domain, 1:1000), anti-FADD (FADD, 1:1000) and active-β-Catenin (P-Ser37 or P-Thr41; 1:800) were purchased from Upstate, anti-MMP9 GE-213 (1:100) was purchased from Oncogene, anti-GFP (1:400) was purchased from Molecular Probes, anti-GADPH was purchased from Abcam and the anti-Caspase-8 antibody (1:10) was generated in our laboratory from hybridoma supernatant[47]. The anti-PED antibody (1:2000) was kindly provided by Dr. Herve Chneiweiss. For visualizing specific antibodies on histological stainings streptavidine-alkaline Phosphatase/FastRed both purchased from Dako were used. For immunofluorescence studies the monoclonal anti odies Alexa Fluor 488 (1:500; Molecular Probes) and anti-Rhodamine (1:200; Dianova) were used.

The MAPK inhibitor, PD98059 (25 μM), the PI3K inhibitor Ly 290059 (25 μM) and the pancaspase inhibitor zVAD-fmk (40 μM) were purchased from Calbiochem. The ILK inhibitor (20 μM) was kindly provided from S. Dedhar. Cells were preincubated with inhibitors 30 minutes (LY 290059 and zVAD-fmk) prior to treatment with either CD95L-T4 or αApo-1. Generation of Leucinezipper-CD95L (LZ-CD95L) was performed as previously described[41]. The blocking agents (zVAD-fmk, PD98059, LY 290059 and KP-SD1) were given 30 minutes before treatment with LZ-CD95L or αApo-1. Cells were lysed for further biochemical analysis. Protein extraction and immunoblotting was performed as previously described[41].

Example 2

Primary Samples

Tissue specimens of NCH tumors were obtained intraoperatively after informed consent of the patients and approval of the local ethics committee. Fresh tissue was divided into two parts, one part to establish primary tumor cultures and the other for RNA extraction. Clinical data of the respective patients concerning tumor classification, age at surgery and sex are summarized in Table I (FIG. 22).

Example 3

Animal Experiments

Animal experiments were approved by the German Cancer Research Center institutional animal care and use committee and the Regierungspäsidium Karlsruhe. For intracranial injections, 8- to 12-week-old inbred Vm/Dk mice were used. 5.000 SMA-560 cells were harvested by trypsinization, resuspended in 1 μl Dulbeccos modified eagle medium (DMEM supplemented with 10% fetal bovine serum (FCS), 1% Penicilin/Streptomycin (PS) and 1% L-Glutamine 200 mM) and loaded into a 10 μl Flexilfil syringe (WPI, Berlin, Germany). A burr hole was drilled 2.75 mm lateral to the bregma and the needle was introduced to a depth of 3 mm. Mice were sacrificed 7, 14 or 18 days after injections.

Example 4

Tumor Explants

Fourteen days after tumor inoculation, mice sacrificed and the tumors extracted. Tumor explants were then incubated for 1 hour in either medium, medium plus isotype control antibody (10 μg/ml) or medium with MFL3 (10 μg/ml). Following embedding of the explants into collagen, cell invasion was recorded over 72 hours with a time-lapse microscope (Olympus, Germany).

Example 5

Cells and Spheroid Cultures

The established glioblastoma cell lines A172, T98G and LN18 and the primary glioblastoma cells (NCHs) were cultured in DMEM (supplemented with 10% FCS and 1% PS) in a CO2incubator at 36.5° C. and 90% humidity. The NCH cell lines have been established in the laboratory of C. Herold-Mende as decribed[48]. For biochemical and molecular analysis $1 \times 10^6$ cells were plated onto 10 cm culture dishes in medium and incubated as described before. Spheroids were produced as previously described[49]. In brief, T98G and LN18 cells ($2\text{-}3 \times 10^4$) were plated in hanging drops (20 μl) onto the lids of 10 cm culture dishes containing 10 ml DMEM. After 48 h the cellular aggregates were harvested and transferred onto a base-coated 2% agar dish filled with medium. After additional 48 h spheroids were embedded in a three-dimensional-collagen-gel for invasion analysis.

Example 6

Collagen-Invasion-Assay

A physiological model for investigating invasion is the three-dimensional-collagen-gel-assay. Spheroids were treated 1 h before being embedded into a collagen gel solution (Vitrogen 3 mg/ml stock solution; final concentration 2.4 mg/ml) with αApo-1 (2 μg/ml), LZ-CD95L (5 ng/ml) or Nok1 (50 ng)/LZ-CD95L (5 ng/ml). After polymerization of the collagen gel (3060 min at 37° C.) DMEM was put on top of the gels. The invasion of cells into the collagen matrix was documented with a time-lapse microscope (Olympus, Germany). The distance of single invading cells to the spheroid border (n=10 per spheroid; 3 spheroids per treatment) was determined with Image J 1.34 software (based on NIH Image).

Example 7

Homogenization of Tissue

For FACS analysis, tumors were removed at indicated time points, trypsinized for 20 min at 37° C., washed thrice in PBS/10% FCS, triturated with glass Pasteur pipettes, filtered through a 100 μm nylon mesh (BD Falcon) and resuspended in PBS/10% FCS for Fluorescence Activated Cell Sorter (FACS, Becton Dickinson) analysis.

Example 8

Migration-Assay

Migration of the glioma cells in vitro was measured by the migration through Collagen I-coated (Chemicon) transwell inserts (Falcon). $5 \times 10^4$ cells were plated in 200 μl medium onto collagen-coated (50 μg/ml) transwell inserts with 8 μm pore size. Cells were either γ-irradiated before plating or treated after plating with α-Apo1 (2 μg/ml or 0.1 μg/ml+ ProteinA for cross linking), LZ-CD95L (5 ng/ml), Nok1 (50 ng)/LZ-CD95L (5 ng/ml), Nok1 (50 ng) LZ-Supernatant (SN, 5 ng/ml), CD95L (10 ng/ml) and CD95L-T34. Preferably 24 h after plating the cells were starved with basal DMEM for additional 24 h before they were treated. The number of completely migrated cells was counted at 12 h, 24 h and 36 h after treatment. In every experiment triplicates were counted for each treatment.

Example 9

Tumor Scoring and Analysis

Scoring of CD95L in original and recurrent gliomas was performed by analysis of three areas (250-fold magnification) from each CD95L-stained tumor. Positive cells were counted in a double blind manner and scores assigned according to the number of positive cells.

For analysis of CD95-induced migration in vivo, a suspension of 5.000 SMA-560 cells and 3 μg of MFL3 or the appropriate isotype antibody was injected into the left striatum of Vm/Dk mice. After one week, mice were sacrificed and the brains extracted. Following immunohistochemical staining, GFP positive cells in the contralateral hemisphere of three representative areas per sample were counted and normalized to the surface of the tumor as assessed by Cell^R software (Olympus, Germany).

Example 11

γ-Irradiation $2.5 \times 10^5$ cells were plated onto 6 cm culture dishes 12 h prior to irradiation. Cells were irradiated with 1, 3, 10 and 50 Gy at room temperature using a $^{137}$Cs source (Gamma Cell 1000, Atomic Energy of Canada, Ltd., ON) at 10.23 Gy/min. Cells were treated with Nok1 (10 μg/ml) or left untreated directly after irradiation. Thereafter cells were used for migration-assays, RNA extraction or Nicoletti-assay.

Example 12

Statistical Analysis

Statistical analysis of migration and mRNA expression data was performed using the nonparametric Student t test to compare differences between treatment groups and controls. Confidence intervals were determined at 95%, and *P values<0.05, P value<0.01. *P value<0.005 were considered statistically significant.

Example 13

Immunoprecipitation $2 \times 10^7$ cells were either treated with 10, 500 and 5 μg/ml CD95L-T4 for 1 and 5 minutes (unless otherwise indicated) at 37° C. or left untreated, washed twice in PBS plus phosphatase inhibitors (NaF, NaN3, pNPP, NaPPi, β-Glycerolphosphate, 10 mM each and 2 mM orthovanadate), and subsequently lysed in buffer A (20 mM Tris/HCl, pH 7.5, 150 mM NaCl, 2 mM EDTA, 1 mM phenylmethylsulfonyl fluoride, protease inhibitor cocktail [Roche], 1% Triton X-100 [Serva, Heidelberg, Germany], 10% glycerol, and phosphatase inhibitors [NaF, NaN3, pNPP, NaPPi, β-Glycerolphosphate, 10 mM each and 2 mM orthovanadate]) (stimulated condition) or lysed without treatment (unstimulated condition). Protein concentration was determined using BCA kit (Pierce). 1 mg of protein was immunoprecipitated overnight with either anti-caspase-8 as previously described[58], 5 μg αApo-1 or 2.5 μg anti-p85 and 30 μl protein-A Sepharose. Beads were washed 5 times with 20 volumes of lysis buffer. The immunoprecipitates were analyzed on either 15% or 7.5% SDS-PAGE. Subsequently, the gels were transferred to Hybond nitrocellulose membrane (Amersham Pharmacia Biotech, Freiburg, Germany), blocked with 2% BSA in PBS/Tween (PBS plus 0.05% Tween 20) for 1 hour, and incubated with primary antibodies in 2% BSA PBS/Tween at 4° C. overnight. Blots were developed with a chemoluminescence method following the manufacturer's protocol (PerkinElmer Life Sciences, Rodgan, Germany).

Example 14

Cell Analysis by Flow Cytometry

Extracellular Staining:

Expression of CD95 on the surface of single cells was analyzed by FACS. $1 \times 10^6$ cells/ml in phosphate-buffered saline containing 10% fetal calf serum (PBS 10% FCS) were incubated with αApo-1 (0.01 μg/μl) for 20 minutes on ice, followed by the secondary antibody (1:30 goat-anti-mouse phycoerythrin-conjugated; Dianova) for 30 minutes. Flowcytometric analysis was performed on a FACSCalibur (Becton Dickinson) using Cell Quest Software. A minimum of 10.000 cells per sample was analyzed.

Intracellular FACS Staining:

To measure either the overexpression efficiency of PTEN, the knockdown efficiency of Yes or the basal levels of FADD, Fyn and Yes, intracellular FACS stainings were performed. Cells were trypsinized, supernatant was discarded and the pellet was resuspended in 4% paraformaldehyde in PB-buffer for 15 minutes on ice. After incubation the fixed cells were centrifuged (3.000 rpm, 4° C., 5 minutes) supernatant was discarded and the pellet was washed twice with PBS/0.1% Saponin and 10% FCS. Samples were incubated on ice for 30 minutes with the first antibody (α-HA 1:1000 Roche, α-Yes 1:200 or α-Fyn 1:200 Santa Cruz), followed by two washing steps with PBS/0.1% Saponin and 10% FCS before addition of the secondary antibody (α-mouse-PE 1:33 Pharmingen or α-rabbit-Alexa488® 1:250 Molecular Probes) for additional 20 minutes. Stained cells were washed twice with PBS/0.1% Saponin and 10% FCS and the pellet resuspended in the same buffer. Cells were then analyzed by FACS. Values were given as normalized mean fluorescent intensity (MFI) for the specific antigen.

Example 15

Detection of Apoptosis (Nicoletti Assay)

To quantify DNA fragmentation, cells detached with trypsin/EDTA (Gibco) were centrifuged at 200×g and fixed with 70% ethanol at −20° C. for 1 h. Fixed cells were stained with propidium iodide solution (50 μg/ml; 0.0025% sodium citrate and 0.0025% Triton-X-100) for 1 h or overnight at 4° C. and analyzed by FACS.

Example 16

Gelatin Zymography for MMP-2 and -9

Conditioned medium of untreated or treated (CD95L-T4 10 ng/ml and 20 ng/ml) T98G cells were loaded under non-reducing conditions onto a 10% SDS-polyacrylamide gel containing 1 mg/mL gelatin. After electrophoresis and washing the gel with Triton X-100 (2.5% v/v, twice for 30 min), the gel was incubated in MMP reaction buffer [50 mmol/L Tris-HCl (pH 7.8), 200 mmol/L NaCl, 5 mmol/L CaCl2] at 37° C. for 16 h. Gelatinolytic activity was detected as transparent bands on staining with Coomassie Brilliant Blue G-250 solution and incubation in destaining solution (10% acetic acid, 20% methanol).

Example 17

Immunohistochemistry

T98G cells were fixed with 4% PFA at 37° C. for 15 minutes, incubated with 50 mM ammonium chloride and permeabilized with 0.1% Triton X-100 in PBS for 5 minutes. After blocking, cells were incubated with the respective primary antibodies, and immunoreactivities were visualized with a monoclonal or polyclonal antibody coupled to rhodamine or fluorescein isothiocyanate (FITC).

Clinical samples from GBM WHO IV were fixed with 4% PFA and paraffin-embedded. Consecutive sections of 5 μm thickness were immunostained with mouse antibodies against CD95L, Yes and phospho-Src (Tyr416). For validation of the anti-CD95L and anti-CD95 antibodies, human tonsils were used. After incubation with biotin-coupled secondary antibodies followed by incubation with streptavidine-alkaline phosphatase (Dako) sections were developed with FastRed (Dako) and embedded with Glycergel (Dako).

Murine tumors were fixed with 4% PFA. After paraffin embedding, consecutive slices of 5 μm thickness were immunostained with rabbit anti-GFP.

Example 18

Lentivirus Infection

T98G and LN18 cells were infected with the lentiviral vector pEIGW and pEIGW-GSK3βS9A at a multiplicity of infection (MOI) of 5. The plasmids were constructed by replacing the eGFP sequence between the EF1a promotor and the WPRE element in pWPTSeGFP (kindly provided by D. Trono, Geneva) with the IRES-eGFP cassette from pIRES2-eGFP (Clontech, Germany). The recombinant lentiviral vector pEIGW-GSK3βS9A was constructed using pcDNA3 HA-GSK3βS9A (kindly provided by Trevor C. Dale). This vector encodes a constitutively active GSK3b mutant containing a serine-to-alanine substitution at residue 9 (GSK3βS9A). All lentiviruses were propagated using previously described methods[41]. Expression of all transgenes was confirmed in infected cells by FACS analysis of GFP expression. The percentage of infected cells was 80-90%.

Example 19

Real Time PCR

RNA from cells treated either with.alpha.Apo-1 (1 μg/ml) or left untreated was extracted with the Qiagen RNeasy Mini Kit at 48 h unless otherwise stated. After the reverse transcription, target mRNA was detected by Taqman real-time PCR with the following gene-specific primers: CD95-forw. 5'-ACT GTG ACC CTT GCA CCA AAT-3' (SEQ ID NO:2); CD95-rev. 5'-GCC ACC CCA AGT TAG ATC TGG-3' (SEQ ID NO:3); CD95-probe 5'-AAT CAT CAA GGA ATG CAC ACT CAC CAG CA-3' (SEQ ID NO:4); CD95L-forw. 5'-AAA GTG GCC CAT TTA ACA GGC-3'(SEQ ID NO:5); CD95L-rev. 5'-AAA GCA GGA CAA TTC CAT AGG TG-3' (SEQ ID NO:6); CD95L-probe 5'-TCC AAC TCA AGG TCC ATG CCT CTG G-3' (SEQ ID NO:7); MMP-9-forw. 5'-GAT CCA AAA CTA CTC GGA AGA CTT G-3' (SEQ ID NO:8); MMP-9-rev. 5'-GAA GGC GCG GGC AAA-3' (SEQ ID NO:9); MMP-9-probe 5'-CGC GGG CGG TGA TTG ACG AC-3' (SEQ ID NO:10); MMP-2-forw. 5'-GGA CAC ACT AAA GAA GAT GCA GAA GT-3' (SEQ ID NO:11); MMP-2-rev. 5'-CGC ATG GTC TCG ATG GTA TTC-3' (SEQ ID NO:12); MMP-2-probe 5'-AGT GCC CCA GCA AGG TGA TCT TGA CC-3' (SEQ ID NO:13); b-Actin-forw. 5'-ACC CAC ACT GTG CCC ATC TAC GA-3' (SEQ ID NO:14); b-Actin-rev. 5'-CAG CGG AAC CGC TCA TTG CCA ATG G-3' (SEQ ID NO:15); b-Actinprobe 5'-ATG CCC TCC CCC ATG CCA TCC TGC GT-3' (SEQ ID NO:16). To proof the knockdown of Yes, target mRNA was detected by SybrGreen real-time PCR with the use of the following primers of the Src kinase family: Yes-forw. 5'-TAT GGC TGC CAG ATT GCT G-3' (SEQ ID NO:17); Yesrev. 5'-ZZC AGG AGC TGT CCA TTT GA-3' (SEQ ID NO:18); Fyn-forw. 5'-TGA ACA GCT CGG AAG GAG AT-3' (SEQ ID NO:19); Fyn-rev. 5'-GGT TTV ACT CTC CGC GAT AA-3' (SEQ ID NO:20); as housekeeping gene Gapdh was used with the following sequences: Gapdh-forw. 5'-GGT CGG AGT CAA CGG ATT TGG TCG-3' (SEQ ID NO:21); Gapdh-rev. 5'-CCT CCG ACG CCT GCT TCA CCA C-3' (SEQ ID NO:22). The realtime PCR was measured in a ABIPRISM-7300i (Applied Biosystems, USA).

Example 20

PTEN Overexpression

Overexpression plasmids for PTEN (pBP-PTEN-HA) and the empty vector (pBP) were kindly provided by Frank Furnari (San Diego, USA)[59]. T98G cells were transfected with pBP-PTEN-HA and pBP (6 μg) using JetPei. Transfected cells were cultured for an additional 48-72 h before treatment.

Example 21

Knockdown Experiments

Knockdown experiments were performed by transient transfection with Lipofectamine 2000™ (Invitrogen Life Technologies) following the instruction manual. Migration experiments were performed using either validated siRNA against Yes (Qiagen SI00302218), and a second siRNA, targeting a different member of the Src family kinases, Fyn (Qiagen SI00605451), which was used as a negative control or pools of validated shRNAmir-pGIPZvectors for Yes, MMP-2 and MMP-9 and a non-targeting shRNAmir-pGIZ vector as a negative control (RHS 4430-98843955, -98820654, -99161516, -98514235, -98709361, -99137419, -99291751, -99298712, -99138418 and RHS4346-OB respectively, Open Biosystems, USA). After transient transfection with the different siRNAs cells were cultured for 72 h before treated with CD95LT4 (10 ng/ml and 20 ng/ml), migration was analyzed 24 h after treatment with a two dimensional migration assay. The knockdown was controlled by quantitative real-time PCR and FACS. To exclude off-target effects of Yes-siRNA, cells were transfected with siRNA against Yes, a Yes overexpression plasmid (p-CMV-Yes) or both and cultured for 48 h before being transferred to a migration plate. After additional 48 h cells were treated with CD95L-T4 (10 ng/ml and 20 ng/ml). Migration was measured 24 h after treatment in a two dimensional migration assay.

For immunoprecipitation studies, transfected cells were cultured for 72 h prior to treatment.

Example 22

Luciferase Reporter Gene Assays

Luciferase reporter vectors were kindly provided from the following sources: pTOPFLASH and pFOPFLASH (Randall T. Moon, Howard Hughes Medical Institute of Washington; USA) and the NFκB plasmid with six NFκB-binding sites (Min Li-Weber, German Cancer Research Center Heidelberg, Germany). Transfection experiments were carried out using Lipofectamine 2000™ reagent (Invitrogen Life Technologies), according to the manufacturer's instructions. Cells were seeded in 24-well plates at a density of 5×104 cells per well 24 h prior to transfection. The Firefly-Luciferase constructs were cotransfected with a CMV-Renilla-Luciferase plasmid (10 ng) to normalize the luciferase values. Luciferase activity was measured 24 h after transfection depending on the construct by using commercially available kits from Promega (Madison, Wis., USA). Luminescence was quantified using a Ascient 96-well microplate luminometer. All transfections were carried out in quadruplicates on at least two independent occasions, and error bars represented as s.e.m.

Example 23

Generation of CD95L-T4

Genetic Engineering of Human CD95-Ligand-T4 (CD95L-T4)

The TRAIL/DR5 complex as well as the TNF-.alpha. structure were used as models to develop expression strategies for the human CD95L-receptor binding domain (CD95L-RBD). Provided that the structure of trimeric human CD95L-RBD is in principle similar to the TNF-.alpha.- or TRAIL-RBD-structures (PDB-entries: 1TNF and 1 D0G/1 DU3, respectively.sup.51, 55, 62), the following observations were taken into account: [0136]
  1. The N- and C-terminal amino acids of the RBD from TRAIL and TNF-α form an antiparallel.beta.-strand. [0137]
  2. The terminal amino acids of this.beta.-strand are located next to each other at the same site of the molecule close to the central axis of the TRAIL-RBD trimer (see FIG. 19).

This means, that for steric reasons, the use of N- and C-termini in the same molecule for the fusion of protein domains (e.g. for the addition of stabilization motifs or tags) is mutually exclusive. The ideal stabilisation motif should be a small, well defined trimer located close to the central axis of the CD95L-trimer with its N- and C-terminus at opposite sites of the stabilisation motif in order to minimize its risk of interference with the ligand/receptor interaction sites. An appropriate trimeric protein domain fulfilling these criteria is the T4-Foldon motif from the fibritin of the bacteriophage T4.sup.61, 65. According to the above mentioned considerations the T4-Foldon was fused C-terminally to the human CD95L-RBD (Glu142-Leu281 of CD95L). Between the CD95L-RBD and the T4-Foldon, a flexible linker element (GSSGSSGSSGS; SEQ ID NO: 23) was placed and a hexa-histidine tag and a streptag-II (HHHHH-HSAWSHPQFEK; SEQ ID NO:24) was added C-terminally. This affinity tag was linked to the T4-Foldon by a flexible linker element (SGPSSSSS; SEQ ID NO:25). To allow for secretory based expression, a signal peptide from human Igk was fused to the N-terminus (Glu142). The proposed signal peptide cleavage site formed by the fusion of the Iv leader to the CD95LRBD is expected to release a final product with a N-terminal located Glutamine, corresponding to Glu142 of human CD95L. The amino acid sequence of the CD95L-T4-construct shown in FIG. 19C was backtranslated and its codon usage optimized for mammalian cell-based expression. Gene synthesis was done by ENTELECHON GmbH (Regensburg, Germany). The final expression cassette was subcloned into pCDNA4-HisMaxbackbone, using unique Hind-III- and Not-I-sites of the plasmid. A schematic summary, including all features described above, is shown exemplarily for the TRAIL-T4-DR5-complex (FIG. 19D).

Expression and Purification of CD95L-T4

Hek 293T cells grown in DMEM+GlutaMAX (GibCo) supplemented with 10% FBS, 100 units/ml Penicillin and 100 µg/ml Streptomycin were transiently transfected with a plasmid encoding CD95L-T4. Cell culture supernatant containing recombinant CD95L-T4 was harvested three days post transfection and clarified by centrifugation at 300 g followed by filtration through a 0.22 µm sterile filter. For affinity purification 1 ml Streptactin Sepharose (IBA GmbH, Göttingen, Germany) was packed to a column and equilibrated with 15 ml buffer W (100 mM Tris-HCl, 150 mM NaCl pH 8.0). The cell culture supernatant was applied to the column with a flow rate of 4 ml/min. Subsequently, the column was washed with buffer W and bound CD95L-T4 was eluted stepwise by addition of 7×1 ml buffer E (100 mM Tris-HCl, 150 mM NaCl, 2.5 mM Desthiobiotin, pH 8.0). The protein content of the eluate fractions was analysed by SDS-PAGE and silver staining (FIG. 19E). Fractions E2-E5 were subsequently concentrated by ultrafiltration and further analysed by size exclusion chromatography (SEC). SEC was performed on a Superdex 200 column using an Äkta chromatography system (GEHealthcare). The column was equilibrated with phosphate buffered saline and the concentrated, streptactin purified CD95L-T4 (E2-E5) was loaded onto the SEC column at a flow rate of 0.5 ml/min. The elution of CD95L-T4 was monitored by absorbance at 280 nm. The apparent molecular weight of purified CD95L-T4 was determined based on calibration of the Superdex 200 column with gel filtration standard proteins (FIGS. 19F and G) (Bio-Rad GmbH, München, Germany).

Apoptosis Assay

A cellular assay with a Jurkat A3 permanent human T-cell line (cat. no. CRL2570, ATCC) was used to determine the apoptosis inducing activity of CD95L-T4. Jurkat cells were grown in flasks with RPMI 1640-medium+GlutaMAX (GibCo) supplemented with 10% FBS (Biochrom), 100 units/ml Penicillin and 100 μg/ml Streptomycin (GibCo). Prior to the assay, 100,000 cells were seeded per well into a 96-well microtiterplate. The addition of different concentrations of CD95L-T4 to the wells (final volume: 200 μl) was followed by a 3 h incubation at 37° C. Cells were lysed by adding 20 μl lysis buffer (250 mM HEPES, 50 mM $MgCl_2$, 10 mM EGTA, 5% Triton-X-100, 100 mM DTT, 10 mM AEBSF, pH 7.5) and plates were put on ice for 30 minutes. Apoptosis is paralleled by an increased activity of caspase-3 and caspase-7. Hence, cleavage of the specific caspase-3/-7 substrate Ac-DEVD-AFC (Biomol) was used to determine the extent of apoptosis. In fact, Caspase activity correlates with the percentage of apoptotic cells determined morphologically after staining the cells with propidium iodide and Hoechst-33342 (data not shown). For the Caspase activity assay, 20 μl cell lysate was transferred to a black 96-well microtiterplate. After the addition of 80 μl buffer containing 50 mM HEPES, 1% Sucrose, 0.1% CHAPS, 50 μM Ac-DEVD-AFC, and 25 mM DTT, pH 7.5, the plate was transferred to a Tecan Infinite F500 microtiter-plate reader and the increase in fluorescence intensity was monitored (excitation wavelength 400 nm, emission wavelength 505 nm) (FIG. 19H).

This apoptosis assay was also used for the determination of biological activity of the biopharmaceutical agent APG101. APG101—a fusion protein of the extracellular domain of the human CD95-receptor (the in vivo binding partner of CD95 ligand) with human Fc—antagonizes the apoptosis inducing effect of CD95L. Prior to the addition of CD95L-T4 to the Jurkat cells, CD95L-T4 at a constant concentration was incubated for 30 minutes at 37° C. with different concentrations of APG101 (FIG. 19I).

Example 24

CD95 Mediates Invasion of Glioblastoma Cells Resistant to Apoptosis

Figure 1:
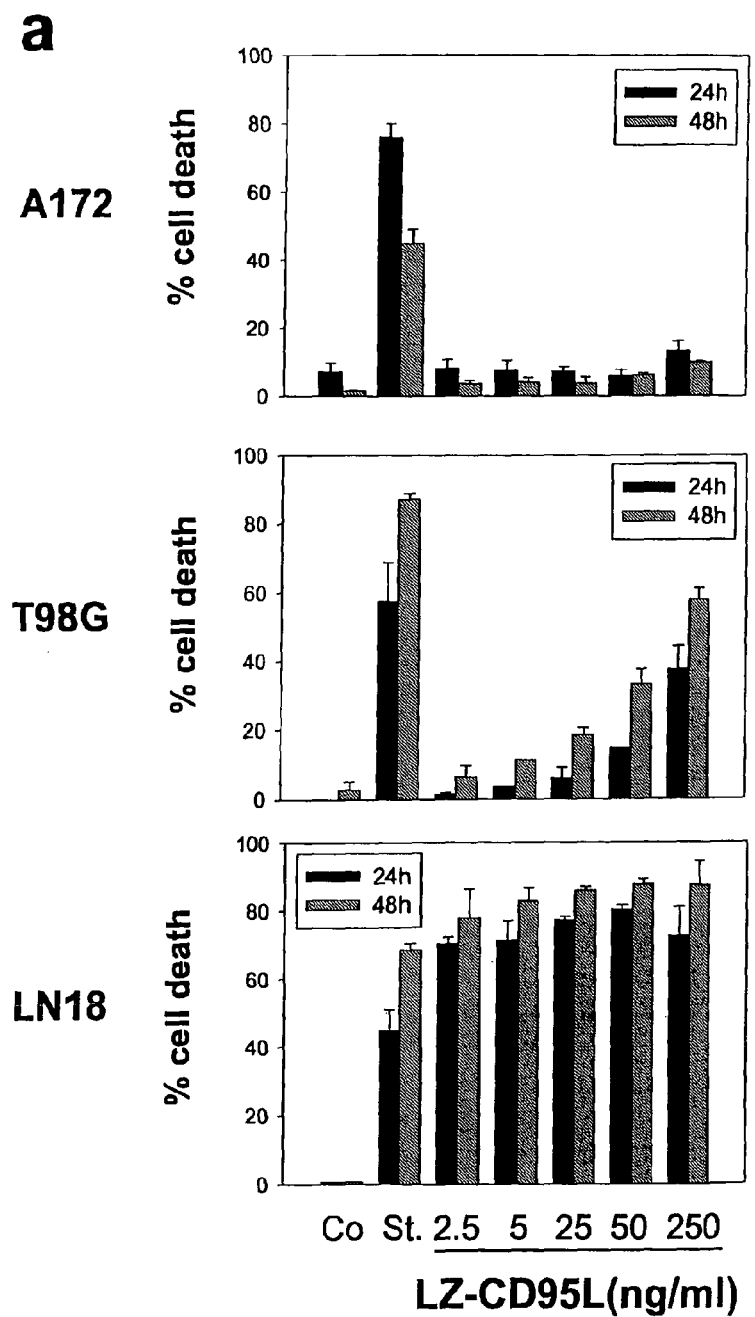
FIG. 1: Sensitivity to CD95-induced death and expression of CD95.
Figure 1:
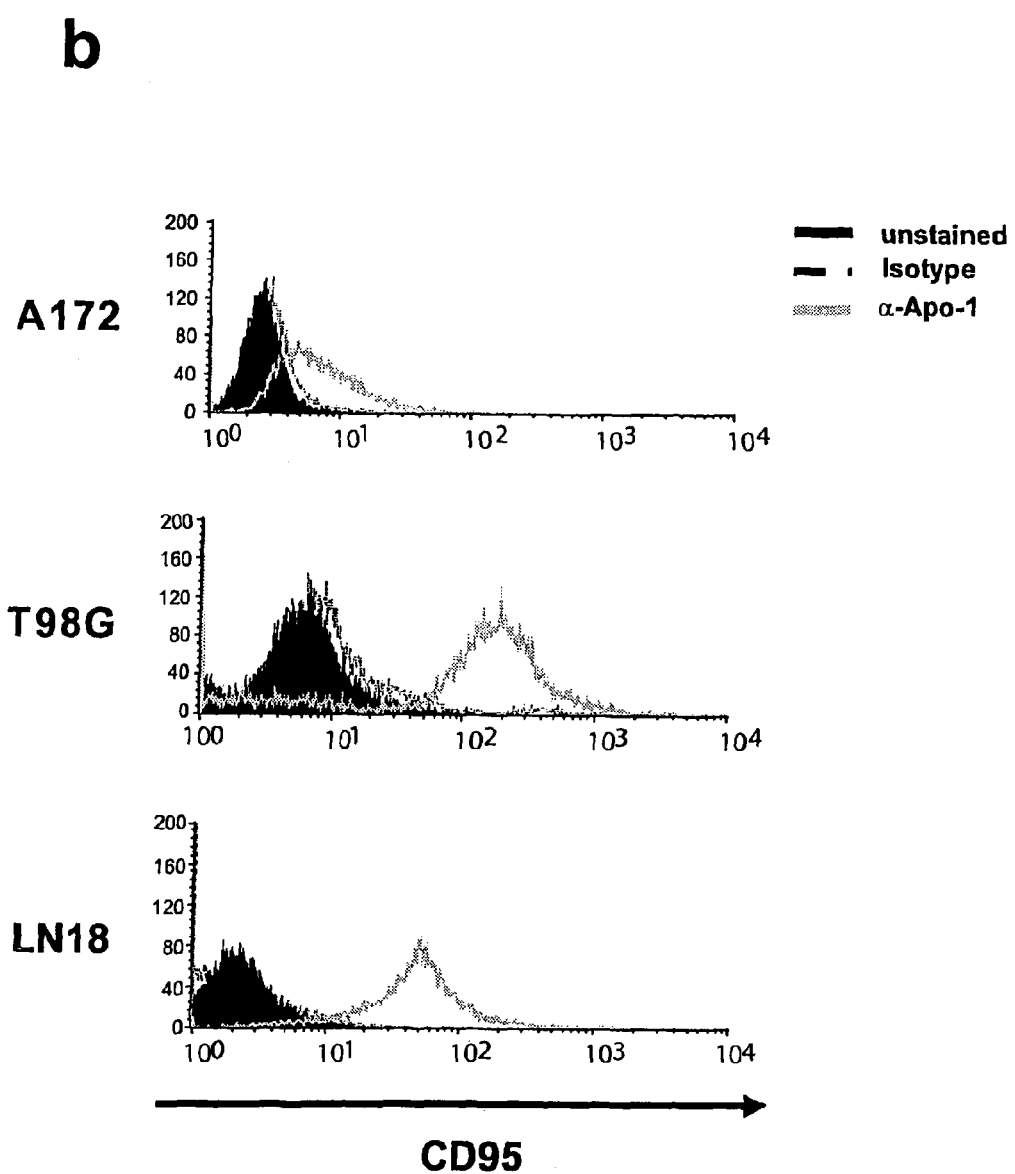
Figure 1:
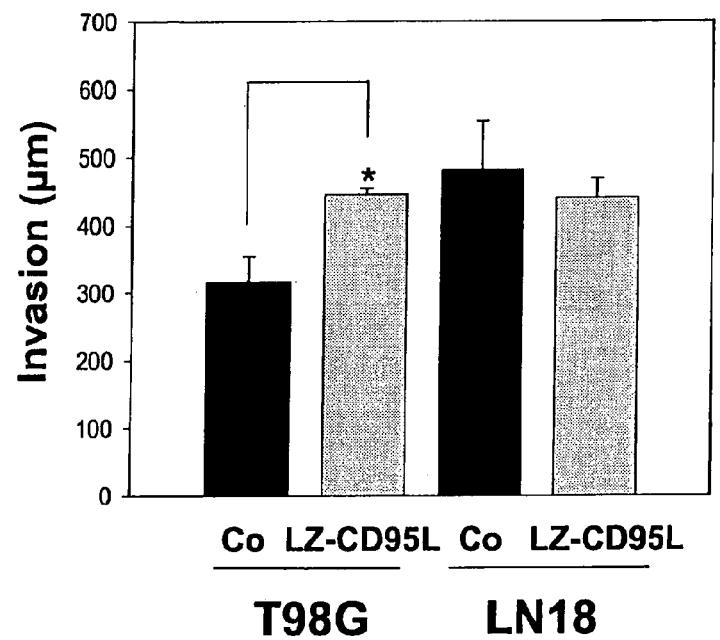
Figure 1:
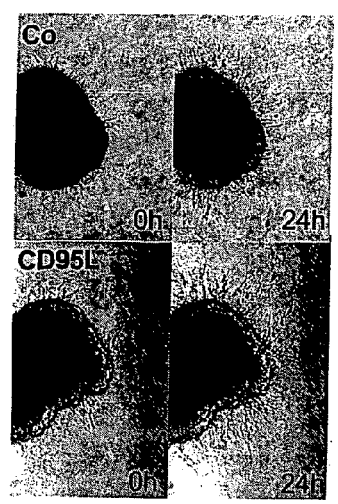

In long-term human malignant glioma cell lines, we first examined the induction of apoptosis upon triggering of CD95. Treatment with leucine zipper (LZ)-CD95L elicited variable effects in different glioma cell lines: LZ-CD95L did not induce apoptosis in A172 cells, caused apoptosis only at high doses in T98G cells or mediated apoptosis already at low doses in LN18 cells (FIG. 1*a*). Specificity of LZ-CD95L-induced death was proven by the neutralization of apoptosis by an antibody to CD95L (NOK1; data not shown). The resistance of A172 to CD95-induced apoptosis could be attributed to the low level of CD95 surface expression (FIG. 1*b*). LN18 and T98G cell lines, however, exhibited different sensitivity to apoptosis while showing comparably high levels of CD95 surface expression (FIG. 1*b*).

Figure 19:
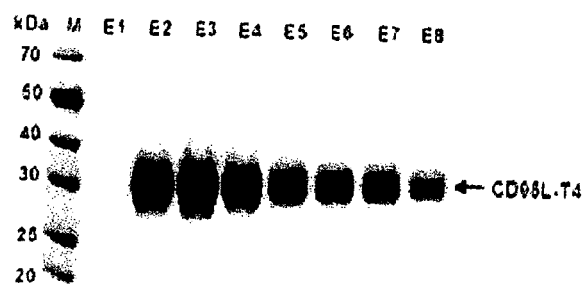
Figure 19:
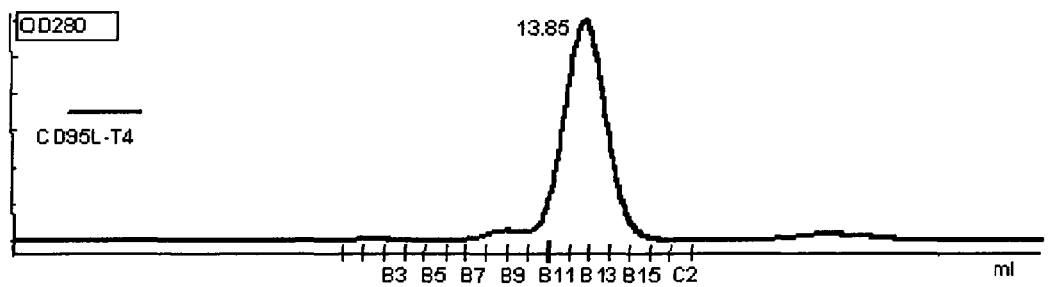
Figure 19:
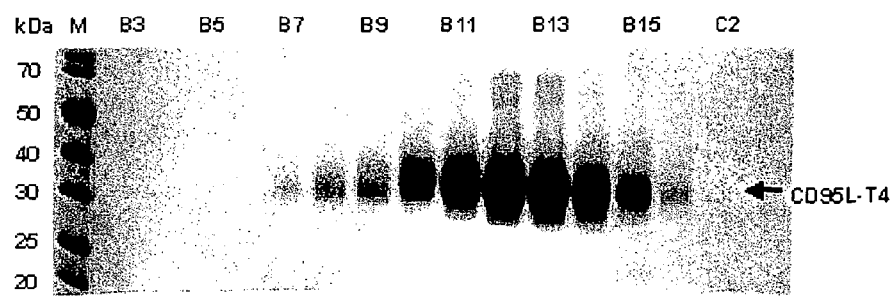
Figure 19:
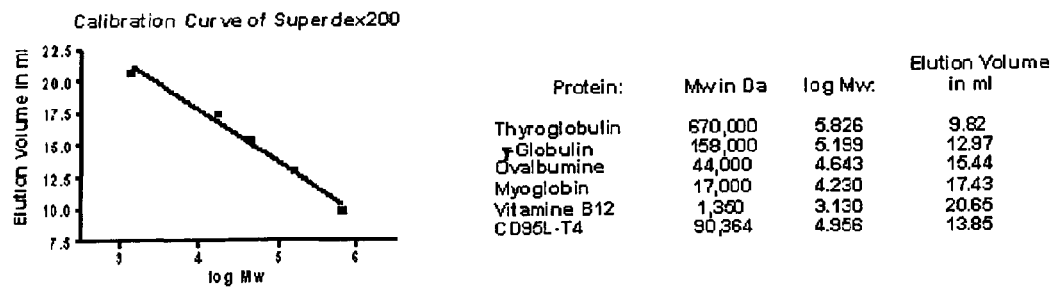
Figure 19:
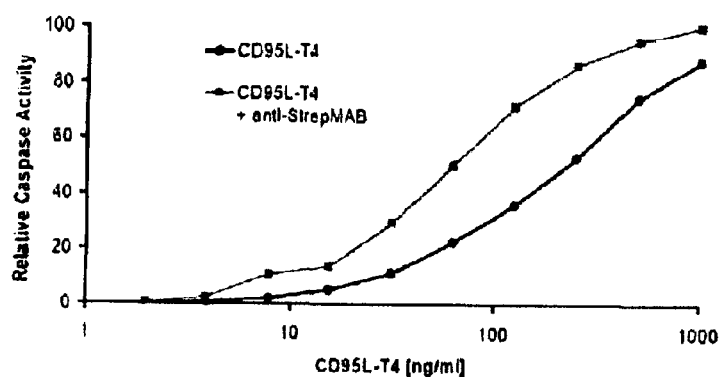
Figure 19:
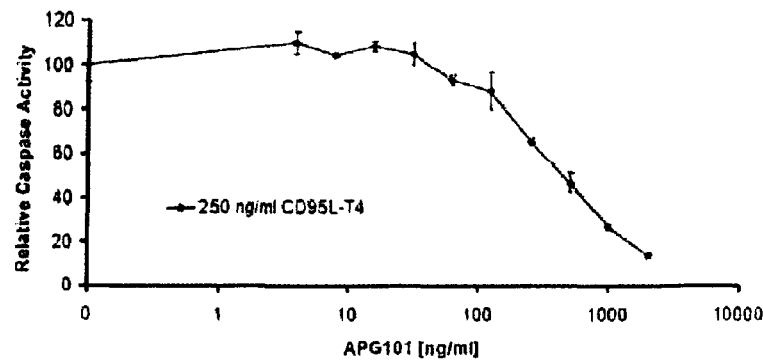

The potency to activate CD95 proportionally correlates with the degree of oligomerization of CD95L. Since the available CD95L has a tendency to form aggregates, we engineered a human CD95L with a stable trimer building capacity, the CD95L-T4 (FIG. 19). Different glioma cell lines exhibited different sensitivities to treatment with CD95L-T4: Apoptosis was induced already at low concentrations in LN18 cells but not in T98G cells (FIG. 11A). Specificity of CD95L-T4-induced death was tested by the neutralization of apoptosis by an antibody to CD95L (NOK1; FIG. 21). Both LN18 and T98G cell lines, however, exhibited comparably high levels of CD95 surface expression (FIG. 11A). These cell lines also expressed other molecules necessary for CD95-mediated apoptosis, such as FADD, caspase-8 or caspase-3 (FIGS. 15C and D)[63, 72].

Malignant glioma cells are characterized by their replicative potential, induction of angiogenesis, migration/invasion and evasion of apoptosis. Stimulation of CD95 did not alter the proliferation rate of T98G cells (data not shown). To test the invasion behavior we generated spheroid cultures of T98G and LN18 cells and plated them within a collagen matrix. Treatment with LZ-CD95L increased invasion of migrating cells into the surrounding matrix to a higher extent in T98G than in LN18 cells (FIG. 1*c*, FIG. 11B). This was also the case when the cells were plated in the upper chamber of two chambers separated by a collagen-coated membrane. The highly apoptosis-sensitive LN18 cells did not react on CD95 activation with increase migration. T98G cells, in contrast, increased their migration potential upon treatment with LZ-CD95L or a stimulating antibody to CD95 (αAPO-1) (FIG. 3*b*).

The migration of glioma cells requires cleavage of extracellular matrix components through MMPs. In T98G cells, MMP-9 activity, as assessed by gel zymography, increased upon treatment with CD95L-T4 (FIG. 11C). Accordingly, stimulation of CD95 increased expression of MMP-2 and MMP-9 mRNA levels in the migration-prone T98G but not in the apoptosis-sensitive LN18 cells (FIGS. 11D and E). Most importantly, CD95-induced migration of T98G cells could be blocked with siRNA pool against MMP-2 and -9, indicating that these MMPs are required for CD95-induced migration (FIGS. 1F and G).

In a further series of experiments we used short-term glioma cultures derived from patients' tumors. These cells exhibited the typical GBM-genetic aberrations including single copy losses of the PTEN and CDKN2a loci and single copy gain of the EGFR locus, as assessed by array-CGH analyses (Bernhard Radlwimmer, personal communication). Every primary GBM-derived culture examined here exhibited high CD95 surface expression (n=18) and similar or higher levels of resistance to CD95-induced apoptosis (n=8) compared to the ones observed in the invasion-prone T98G cell line (FIG. 12A, FIG. 20 and data not shown). Both the levels of CD95 surface expression and the resistance to CD95-mediated apoptosis were not affected by the number of passages in culture (data not shown). We further examined CD95-induced invasion in the GBM-derived cultures NCH89, NCH125 and NCH270. Triggering of CD95 in NCH125 and NCH270 increased expression of MMP-2 and MMP-9 and subsequently induced migration (FIG. 12B to D). Stimulation of CD95 in NCH89 cells neither increased migration nor expression of MMP-9 (FIG. 12B to D). Thus, the migration response to CD95 does not strictly correlate with the degree of resistance to apoptosis. Along the same line, expression of CD95 and CD95L mRNA differed among the highly invasive primary GBM tumors tested (FIG. 20). MMPs are required for CD95L-T4-induced migration of NCH125, as a siRNA pool to MMP-2 and -9 significantly blocked migration (FIG. 12E).

Example 25

CD95 Mediates Invasion Via the PI3K/ILK/GSK/MMP Pathway in a Caspase-Independent Manner The invasion of glioma cells requires cleavage of extracellular matrix components through matrix metalloproteinases (MMP) as already outlined above. Accordingly, mRNA levels of MMP9 and MMP-2 greatly increased upon CD95 triggering in the migration-prone T98G but not in the apoptosisresistant LN18 cells (FIG. 2). The integrin-linked kinase (ILK)

has recently been reported to mediate MMP9 expression via inhibition of glycogen synthase kinase-3β (GSK3β)[9,10]. Inhibition of GSK3β via phosphorylation at its serine-9 (phospho-ser9) residue was observed in T98G cells upon treatment with LZ-CD95L or αAPO-1 antibody (FIG. 3a and FIG. 8). Phosphorylation of GSK3β was also found in LN18 cells, but with different kinetics (FIG. 3a and FIG. 8). The migration-prone T98G cells exhibited higher basal phospho-ser9-GSK3β levels and gradually increasing long-lasting phosphorylation of GSK3β upon triggering of CD95 (FIG. 3a and FIG. 8). The apoptosis-prone LN18 cells showed a transient (5-10 min) phosphorylation of GKS3β upon triggering of CD95 (FIG. 3a). Overexpression of a constitutively active GSK3β mutant (GSK S9A) blocked CD95-induced migration of T98G cells (FIG. 3b). GSK S9A-expressing T98G cells and their wild-type counterparts exhibited comparable levels of sensitivity to CD95-induced apoptosis and of growth rate (FIG. 3c-d). Thus, inhibition of migration by constitutively active GSK3β in T98G cells cannot be attributed to a different proliferation rate. Consequently, pre-treatment with the ILK inhibitor KP-SD-1 blocked CD95-mediated migration of T98G cells without affecting basal migration (FIG. 3e). ILK activates protein kinase B (PKB/AKT) and inhibits GSK3β activity in a phosphatidylinositol-3-kinase (PI3K)-dependent manner[11]. Accordingly, inhibition of PI3K by LY294002 blocked CD95-induced AKT activity and ser9 phosphorylation of GKS3β in T98G cells without changing the phosphorylation status of the extracellular receptor kinase (ERK) (FIG. 3f).

β-catenin forms a complex together with active GSK3β, the adenomatous polyposis coli (APC) and axin proteins—the degradation complex. Phosphorylation of β-catenin by GSK3β targets it for proteasomal degradation. As a consequence of GSK3β inhibition, β-catenin accumulates and translocates into the nucleus where it engages the N-terminus of DNA-binding proteins of the TCF/Lef family[12] inducing expression of different target-genes including MMPs. In T98G cells, triggering of CD95 induced nuclear translocation of active β-catenin, not phosphorylated in the GSK-targeted serine 37 or Threonine 41 (FIG. 3g). Taken together, activation of CD95 induces migration/invasion through the PI3K/ILK/GSK3β/β-catenin/MMP pathway.

CD95 transduces the apoptotic signal through activation of caspases. It has recently been reported that CD95 mediates migration via activation of caspase-8, NFκB and ERK in mesenchymal tumor cells lines resistant to CD95-induced apoptosis[13]. In contrast to LN18 cells, CD95 stimulation of T98G cells did not induce cleavage of caspase-8 (FIG. 3h). Accordingly, pre-treatment of T98G cells with a broad-spectrum caspase inhibitor, benzoyl-VAD.fluoromethyl ketone (zVAD.fmk) did not block ser9 phosphorylation of GSK3β in T98G cells (FIG. 8). Pre-treatment of T98G cells with the MEK inhibitor PD98059 also did not interfere with CD95-induced migration (FIG. 3i).

In addition to caspases, the phosphoprotein enriched in diabetes/phosphoprotein enriched in astrocytes-15 kDa (PED/PEA-15) has a DED and can, therefore, interact with other molecules at the DISC. Overexpression of PED has been reported to block CD95- and TNFR-1-induced apoptosis through simultaneous activation of ERK and inhibition of Jun N-terminal kinase (JNK)[14,15]. The anti-apoptotic activity of PED increases if phosphorylated by AKT[16]. In T98G cells, short interference (si)-RNA to PED but not a control siRNA decreased PED levels and its reported activation of ERK, but not the CD95-mediated inactivation of GSK3β (FIG. 8). In addition the levels of FLIPL, another molecule that can be recruited to the DISC and inhibit apoptosis, remained unaffected upon treatment with LZCD95L (data not shown).

One of the best described inducers of GBM invasion is EGF. Its binding to EGFR promotes MMP-9 expression through activation of the MAPK/ERK and the PI3K pathway[27]. PI3K activates AKT/PKB, which in turn is able to phosphorylate GSK3β leading to its inactivation. To test if PI3K or MAPK signalling could be responsible for the observed invasion we determined phosphorylation of ERK and AKT. Stimulation of T98G and LN18 cells with CD95L-T4 activated AKT but not ERK (FIG. 13A). Interestingly, ERK activity was even blocked with increasing time following stimulation (FIG. 13A). In the invasionprone T98G, NCH125 and NCH270 cells, phosphorylation of AKT exhibited a concentrationdependent bell-shaped curve (FIG. 13B). In contrast, in NCH89 cells, which did not react to CD95 with increased invasion, CD95L-T4 did not activate AKT above basal levels (FIG. 13B). Inhibition of GSK3β via phosphorylation at its serine-9 (phospho-ser9) was observed in T98G cells upon treatment with CD95L-T4 or αApo-1 antibody by Western Blot and FACS staining (FIG. 13C and FIG. 21).

Overexpression of a constitutively active GKS3β mutant (GSK S9A) via lentiviral infection blocked CD95-induced migration of T98G cells (FIG. 13D). GSK S9A-expressing T98G cells and their wild-type counterparts exhibited comparable growth rate and levels of sensitivity to CD95-induced apoptosis (FIG. 21). Thus, inhibition of migration by constitutively active GSK3β in T98G cells cannot be attributed to a different proliferation rate. Active GSK3β forms a complex with β-catenin, the adenomatous polyposis coli (APC) and axin proteins—the degradation complex. Phosphorylation of β-catenin by GSK3β targets it for proteasomal degradation. As a consequence of GSK3β inhibition, β-catenin accumulates and translocates into the nucleus, where it engages the N-terminus of DNA-binding proteins of the TCF (T-cell factor)/Lef (lymphoid enhancing factor) family[12], inducing expression of different target genes including c-Jun, an essential transcription factor for MMP-9 expression[31,32]. Alternatively, inhibition of GSK3β activity can directly increase AP-1 expression[10]. To study whether stimulation of CD95 triggers β-catenin's transcriptional activity we examined expression of cytoplasmic and nuclear β-catenin and β-catenin's transcriptional reporter activity. LiCl, a known inhibitor of GSK3β and inducer of β-catenin's transcriptional activity was used as a positive control. In T98G cells, triggering of CD95 induced cytoplasmic accumulation of β-catenin 30 minutes after stimulation with CD95L-T4 (FIG. 13E). Further, nuclear translocation of active β-catenin, non-phosphorylated on the GSK targeted Ser 37 or Thr 41 was observed (FIG. 13F). TCF/Lef-reporter activity (TOP-FLASH) was also significantly induced upon CD95L-T4 (FIG. 13G). Mutation of the TCF/Lef binding domain abolished CD95L-T4 induction of luciferase activity (FOP-FLASH; FIG. 13G). Additionally, activity of NFκB increased significantly 8 h after stimulation with 20 but not 10 ng/ml CD95L-T4 (FIG. 13H). Taken together, activation of CD95 induces migration/invasion through the PI3K/AKT/GSK3β/β-catenin/MMP and possibly the PI3K/AKT/NFκB/MMP pathway.

Example 26

CD95-Induced Migration is Also Detected in Primary Glioma Cultures Resistant to Apoptosis In a further series of experiments we used short term glioma cultures derived from patients' tumors. Cells from diffuse astrocytoma (WHO II) exhibited high CD95 surface expression and were relatively sensitive to CD95-mediated apoptosis (FIG. 4). In contrast, cells originating from oligodendroglioma (WHO III) or glioblastoma (WHO IV) were highly resistant to CD95-mediated apoptosis despite high CD95 surface expression (FIG. 4 and FIG. 9). Every primary GBM-derived culture examined here exhibited high CD95 surface expression (n=18) and similar or higher levels of resistance to CD95-induced apoptosis (n=8) in comparison to the ones observed in the invasion-prone T98G cell line (FIG. 9). Both the levels of CD95 surface expression and the resistance to CD95-mediated apoptosis were not affected by the number of passages in culture (data not shown). We further tested three GBM-derived cultures which were relatively (NCH125) or highly resistant (NCH89 and NCH270) to CD95-induced apoptosis. Triggering of CD95 in NCH125 and NCH270 increased expression of MMP9 and MMP-2 and subsequently migration (FIG. 5a-c). Stimulation of CD95 in NCH89 cells neither increased migration nor expression of MMP9 and MMP-2 (FIG. 5b-c). Thus, the migration response to CD95 does not strictly correlate with the degree of resistance to apoptosis. Along the same line, expression of CD95 and CD95L mRNA was very different among the highly invasive primary GBM tumors tested (FIG. 9).

Example 27

Irradiation Increases Invasiveness via the CD95/CD95L System

In the clinical setting, invading cells that escape surgery are the targets of radiotherapy and adjuvant chemotherapy. γ-irradiation has been reported to increase expression of CD95 and CD95L and thereby induce apoptosis[3]. Considering our present data we wanted to address whether irradiation-induced CD95 and CD95L could also increase invasiveness of glioma cells. First, we showed that irradiation of T98G cells increases expression of CD95 and CD95L mRNA (FIG. 6a). The highest expression of CD95 and CD95L mRNA was found at a dose of 3 Grays (Gy). At the same dose, MMP-2 mRNA was significantly induced (FIG. 6b). MMP9 mRNA was also significantly upregulated at 3 and 10 Gy but to a lower extent (FIG. 6b). Most importantly, MMP expression was mirrored by a higher migration rate of irradiated cells that could be reverted by neutralization of CD95L (FIG. 6c). Primary GBM cultures also exhibited a more invasive phenotype following irradiation (FIG. 6d and FIG. 10). Irradiation-induced migration was fully CD95L-dependent (FIG. 6d). Interestingly, even in NCH89 cultures that did not exhibit an invasive phenotype after direct triggering of CD95, 10 Gy irradiation increased the number of migrating cells via CD95L (FIG. 6d). Irradiation significantly induced migration in a CD95-dependent manner in nine out of the ten GBM-derived primary cultures examined here (FIG. 6d and FIG. 10). The only culture that failed to exhibit a significant tendency to migrate upon CD95 stimulation had lower CD95 surface expression levels (NCH 417; FIG. 10). We further studied expression of these molecules in recurrent-tumors arising after surgery and irradiation of the original tumor. Expression levels of CD95L within the tumor were scored from 0 to 4 (FIG. 6e). While levels in the first detected glioma were never above 0 (1-24 CD95L-positive cells per field), a dramatic increase of CD95L expression following radiotherapy was detected in eight of the nine recurrent tumors studied (FIG. 6e). CD95L was detected in GFAP-positive tumor cells (FIG. 6f). Additional expression of CD95 and MMP9 was detected in the same region in consecutive slices (FIG. 6f). Importantly, apoptotic cells were not observed near CD95L-expressing cells (data not shown).

Example 28

PI3K is Activated Via Recruitment of Src to CD95

Src connects CD95 to PI3K activity as shown by co-immunoprecipitation experiments (FIG. 14A to C). Indeed, treatment of T98G and LN18 cells with CD95L-T4 induced recruitment of Src and the p85 subunit of PI3K to CD95. Association of p85 with CD95 was examined by immunoprecipitating either CD95 or p85. The degree of association of p85 with CD95 inversely correlated with the concentration of CD95L-T4 in T98G cells (FIG. 14B). However, in LN18 cells p85 recruitment to CD95 was only detected at high concentrations of CD95L-T4 (FIG. 14A). Immunoprecipitation of CD95 allowed detection of a Src-family member at five minutes after treatment with low concentration of CD95L-T4 (FIGS. 14A and B). Src association decreased at a higher concentration (FIGS. 14A and B). Thus, at low concentrations of CD95L-T4 both Src and p85 associated at detectable levels with CD95 in T98G cells but in LN18 cells only Src was detected. Further, after a screening with antibodies to several SFKs, such as Fyn, Lyn, pp60 and Yes, we identified Yes as the Src-family member which links CD95 to PI3K (FIG. 14C). To validate the role of Yes in the migration of glioma cells, knockdown experiments were performed. In cells transfected with Yes siRNA, expression of Yes, as assessed by FACS and qRT-PCR, was reduced while Fyn expression, another Src-family member, remained unaffected (FIG. 14E). siRNA to Yes but not to Fyn, significantly abolished CD95L-T4-induced migration of T98G and of NCH125 cells (FIG. 14D). This block of migration was rescued by Yes overexpression in T98G and LN18 cells (FIG. 14F). Like the PI3K inhibitor LY290059, siRNA to Yes also inhibited CD95-induced phosphorylation of AKT (FIG. 14G).

Example 29

Inefficient DISC Formation in Apoptosis Resistant Glioma Cells

The role of the PI3K pathway repressor PTEN (MMAC1, TEP1) was examined. While the apoptosis prone LN18 cells have an intact PTEN, T98G cells carry a point mutation (codon 42 CTT to CGT; Glycine to Glutamine) in one allele and lack of the second allele of PTEN and a total loss of one of the chromosome 10[57, 59]. PTEN overexpression, however, did not sensitize T98G nor NCH125 cells to CD95-mediated apoptosis (FIG. 15A).

We further questioned whether caspases were involved in CD95-induced activation of PI3K. Inhibition of caspases by the general caspase inhibitor zVAD-fmk did not prevent GSK3β phosphorylation (FIG. 15B). Likewise, CD95-induced cleavage of caspase-8 could only be detected in LN18 but not in T98G cells (FIG. 15C). To investigate if DISC components were efficiently recruited in these cells we analyzed FADD recruitment in CD95-immunoprecipitates. Whereas upon stimulation with CD95L-T4 recruitment of FADD to CD95 increased in LN18 cells, no increase was detected in T98G cells (FIG. 15D). Accordingly, caspase-8 recruitment to CD95 increased upon stimulation with CD95L-T4 in LN18 and J16 cells but not in T98G cells (FIG. 15D). Most importantly, in T98G cells, siRNA knockdown of Yes enabled CD95L-T4 induction of FADD recruitment to CD95 (FIG. 15E). Along this line, while expression levels of FADD were similar in LN18 and T98G cells, Yes levels were significantly higher in T98G cells (FIG. 15F). As opposed to Yes, Fyn expression was significantly higher in LN18 cells (FIG. 15F).

Example 30

The CD95/CD95L System is an Important Mediator of Glioma Invasion in vivo

Expression of CD95L in patients suffering from Glioblastoma multiforme showed a triangle-like distribution of CD95L in every tumor examined (FIGS. 7a, 17A). Inside the tumor, only small amounts of CD95L were expressed (FIGS. 7a.1, 17A.a). Expression increased at the tumor-parenchyma interface (FIG. 7a.2), peaked in the brain parenchyma adjacent to the tumor (FIGS. 7a.3, 17A.b) and decreased again with increasing distance to the glioma (FIGS. 7a.4, 17A.c). CD95L was detected in glioma cells, neurons and macrophages (data not shown). Additional expression of CD95L within the tumor was observed in glioma cells surrounding tumor vessels. Likewise, phosphorylation of Src family kinases (pSrc) and Yes expression were consistently found at the tumor-host interface in every examined sample, suggesting a role in tumor invasion (FIG. 17B). Within solid tumor areas, expression of Yes highly varied between tumor samples, from very high to expression only in scattered tumor cells. In this highly Yes-expressing areas phosphorylation of Src was either not detected or rather limited (FIG. 17B).

For translation of our findings into a more physiological in vivo setting we examined the role of the CD95/CD95L system in a mouse model of Glioblastoma multiforme. For these studies, the established murine glioma cell line SMA-560 was injected intracranially into a syngenic Vm/Dk host as described. The use of a syngenic tumor model was important to allow tumor's induction of CD95L expression in surrounding brain tissue.

SMA-560 cells expressed only low levels of CD95 receptor on their surface (FIGS. 7b, 18A) and no CD95L at all (FIGS. 7c, 18B) when kept under cell culture conditions. As reported by others[17] we found SMA-560 cells to be resistant to CD95-induced apoptosis (Data not shown). Following the formation of spheroids, the levels of CD95 slightly increased (FIGS. 7b, 18A), whereas FACS analysis failed to identify CD95L at the cell surface (FIGS. 7c, 18B). Despite the relatively low amount of CD95 surface levels, spheroids formed from these cells display increased migration in the collagen invasion assay after CD95 stimulation in a dose-dependant manner (FIGS. 7d, 18C). In accordance with our finding that spheroids do not express CD95L (FIGS. 7c, 18B), blockage of CD95L using the CD95L neutralizing antibody MFL3 did not alter invasion (FIGS. 7d, 18C).

Interestingly, FACS analysis of the surface levels of CD95 and CD95L showed a significant increase of both molecules (FIGS. 7b and 7c, 18A and 18B) when cells isolated from solid tumors were analysed 14 and 18 days after inoculation. This indicates the requirement of tumor-host interaction and, therefore, a cross-talk between host factors and tumor cells as given in the case of murine GBM.

For a more detailed analysis of the functional significance of this increase, we extracted fragments from solid tumors 14 days after intracranial injection of cells and preincubated these for one hour with either medium alone, medium with MFL3 or the appropriate isotype antibody, respectively. After embedding into collagen gels, migration was monitored for a period of 72 hours (FIGS. 7e, 18D). Strikingly, preincubation with the CD95L neutralizing antibody MFL3, but not with the isotype or medium alone, reduced migration of cells out of the tumor core by approximately 50% (FIGS. 7e, 18D).

Figure 18E:
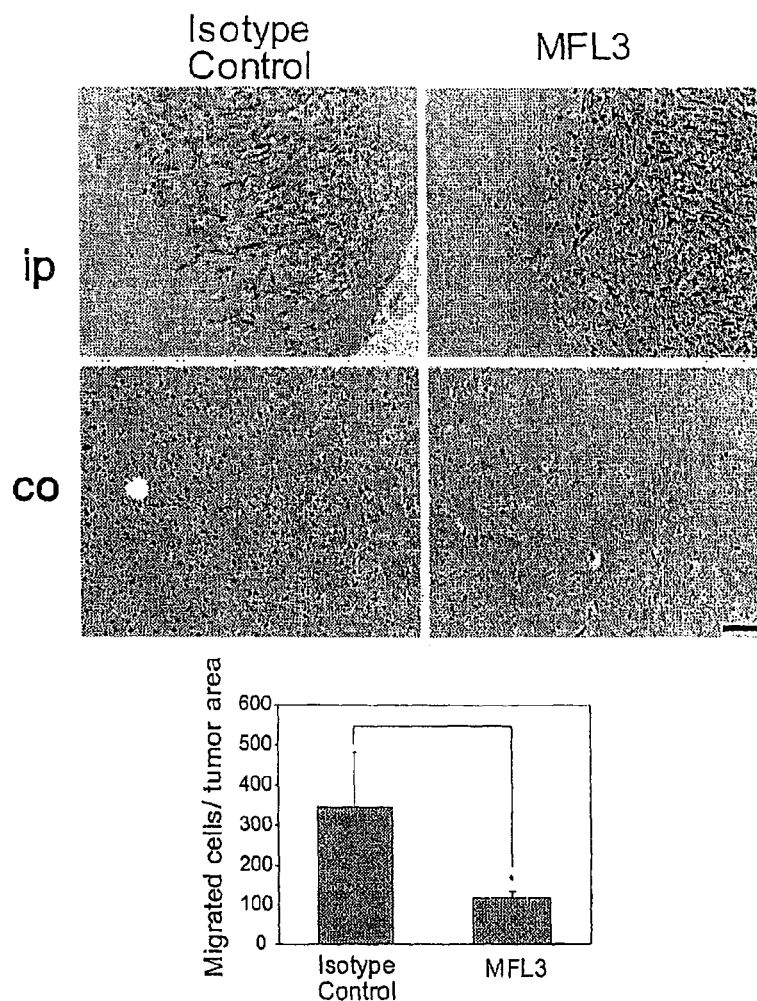

To verify these results in vivo, we injected GFP-positive SMA-560 cells and MFL3 or the appropriate isotype antibody into the left striatum of Vm/Dk. Treatment of mice with MFL3 significantly reduced migration of tumor cells into the contralateral hemisphere (FIGS. 7f, 18E) We conclude from these data that the CD95/CD95L system is a major mediator of malignant glioma invasion into the surrounding brain in vivo.

REFERENCE LIST

All literature cited in this application are incorporated herein by reference.

1. Kleihues, P., Burger, P. C., & Scheithauer, B. W. The new WHO classification of brain tumours *Brain Pathol.* 3, 255-268 (1993).
2. Friesen, C., Herr, I., Krammer, P. H., & Debatin, K. M. Involvement of the CD95 (APO-1/FAS) receptor/ligand system in drug-induced apoptosis in leukemia cells. *Nat Med* 2, 574-7 (1996).
3. Fulda, S. et al. Activation of the CD95 (APO-1/Fas) pathway in drug- and gamma-irradiation-induced apoptosis of brain tumor cells. *Cell Death Differ* 5, 88493 (1998).
4. Kischkel, F. C. et al. Cytotoxicity-dependent APO-1 (Fas/CD95)-associated proteins form a death-inducing signaling complex (DISC) with the receptor. *Embo J* 14, 5579-88 (1995).
5. Kischkel, F. C. et al. Death receptor recruitment of endogenous caspase-10 and apoptosis initiation in the absence of caspase-8 *J. Biol. Chem.* 276, 46639-46646 (2001).
6. Boldin, M. P. et al. A novel protein that interacts with the death domain of Fas/APO1 contains a sequence motif related to the death domain. *J Biol Chem* 270, 7795-8 (1995).
7. Medema, J. P. et al. FLICE is activated by association with the CD95 death-inducing signaling complex (DISC). *Embo J* 16, 2794-804 (1997).
8. Scaffidi, C. et al. Two CD95 (APO-1/Fas) signaling pathways. *Embo J* 17, 1675-87 (1998).
9. Troussard, A. A., Tan, C., Yoganathan, T. N., & Dedhar, S. Cell-extracellular matrix interactions stimulate the AP-1 transcription factor in an integrin-linked kinase- and glycogen synthase kinase 3-dependent manner. *Mol. Cell Biol.* 19, 7420-7427 (1999).
10. Troussard, A. A. et al. The integrin linked kinase (ILK) induces an invasive phenotype via AP-1 transcription factor-dependent upregulation of matrix metalloproteinase 9 (MMP-9). *Oncogene* 19, 5444-5452 (2000).
11. Delcommenne, M. et al. Phosphoinositide-3-OH kinase-dependent regulation of glycogen synthase kinase 3 and protein kinase B/AKT by the integrin-linked kinase *Proc. Natl. Acad. Sci. U.S.A* 95, 11211-11216 (1998).
12. Eastman, Q. & Grosschedl, R. Regulation of LEF-1/TCF transcription factors by Wnt and other signals. *Curr. Opin. Cell Biol.* 11, 233-240 (1999).
13. Barnhart, B. C. et al. CD95 ligand induces motility and invasiveness of apoptosis-resistant tumor cells. *EMBO J.* 23, 3175-3185 (2004).
14. Condorelli, G. et al. PED/PEA-15: an anti-apoptotic molecule that regulates FAS/TNFR1-induced apoptosis *Oncogene* 18, 4409-4415 (1999).

15. Condorelli, G. et al. Multiple members of the mitogen-activated protein kinase family are necessary for PED/PEA-15 anti-apoptotic function *J. Biol. Chem.* 277, 11013-11018 (2002).
16. Trencia, A. et al. Protein kinase B/Akt binds and phosphorylates PED/PEA-15, stabilizing its antiapoptotic action *Mol. Cell Biol.* 23, 4511-4521 (2003).
17. Ashley, D. M., Kong, F. M., Bigner, D. D., & Hale, L. P. Endogenous expression of transforming growth factor beta1 inhibits growth and tumorigenicity and enhances Fas-mediated apoptosis in a murine high-grade glioma model. *Cancer Res.* 58, 302-309 (1998).
18. Krammer, P. H. CD95's deadly mission in the immune system. *Nature* 407, 789-795 (2000).
19. Biancone, L. et al. Development of inflammatory angiogenesis by local stimulation of Fas in vivo *J. Exp. Med.* 186, 147-152 (1997).
20. Hohlbaum, A. M., Saff, R. R., & Marshak-Rothstein, A. Fas-ligand—iron fist or Achilles' heel? *Clin. Immunol.* 103, 1-6 (2002).
21. Lee, J. K., Sayers, T. J., Back, T. C., Wigginton, J. M., & Wiltrout, R. H. Lack of FasL-mediated killing leads to in vivo tumor promotion in mouse Lewis lung cancer *Apoptosis.* 8, 151-160 (2003).
22. Shinohara, H., Yagita, H., Ikawa, Y., & Oyaizu, N. Fas drives cell cycle progression in glioma cells via extracellular signal-regulated kinase activation *Cancer Res.* 60, 1766-1772 (2000).
23. Choi, C. et al. Fas-induced expression of chemokines in human glioma cells: involvement of extracellular signal-regulated kinase 1/2 and p38 mitogen-activated protein kinase *Cancer Res.* 61, 3084-3091 (2001).
24. Choi, C., Gillespie, G. Y., Van Wagoner, N. J., & Benveniste, E. N. Fas engagement increases expression of interleukin-6 in human glioma cells *J. Neurooncol.* 56, 13-19 (2002).
25. Choi, K., Benveniste, E. N., & Choi, C. Induction of intercellular adhesion molecule-1 by Fas ligation: proinflammatory roles of Fas in human astroglioma cells *Neurosci. Lett.* 352, 21-24 (2003).
26. Jarad, G. et al. Fas activation induces renal tubular epithelial cell beta 8 integrin expression and function in the absence of apoptosis *J. Biol. Chem.* 277, 4782647833 (2002).
27. Rao, J. S. Molecular mechanisms of glioma invasiveness: the role of proteases *Nat. Rev. Cancer* 3, 489-501 (2003).
28. Sawaya, R. et al. Elevated levels of Mr 92,000 type IV collagenase during tumor growth in vivo. *Biochem. Biophys. Res. Commun.* 251, 632-636 (1998).
29. Frei, K., Ambar, B., Adachi, N., Yonekawa, Y., & Fontana, A. Ex vivo malignant glioma cells are sensitive to Fas (CD95/APO-1) ligand-mediated apoptosis *J. Neuroimmunol.* 87, 105-113 (1998).
30. Weller, M. et al. Anti-Fas/APO-1 antibody-mediated apoptosis of cultured human glioma cells. Induction and modulation of sensitivity by cytokines *J. Clin. Invest* 94, 954-964 (1994).
31. Sato, H. & Seiki, M. Regulatory mechanism of 92 kDa type IV collagenase gene expression which is associated with invasiveness of tumor cells *Oncogene* 8, 395-405 (1993).
32. Gum, R. et al. Stimulation of 92-kDa gelatinase B promoter activity by ras is mitogen-activated protein kinase kinase 1-independent and requires multiple transcription factor binding sites including closely spaced PEA3/ets and AP-1 sequences *J. Biol. Chem.* 271, 10672-10680 (1996).
33. Lakka, S. S. et al. Downregulation of MMP-9 in ERK-mutated stable transfectants inhibits glioma invasion in vitro *Oncogene* 21, 5601-5608 (2002).
34. Ellerbroek, S. M. et al. Phosphatidylinositol 3-kinase activity in epidermal growth factor-stimulated matrix metalloproteinase-9 production and cell surface association. *Cancer Res.* 61, 1855-1861 (2001).
35. Reya, T. & Clevers, H. Wnt signalling in stem cells and cancer *Nature* 434, 843-850 (2005).
36. Mann, B. et al. Target genes of beta-catenin-T cell-factor/lymphoid-enhancer-factor signaling in human colorectal carcinomas *Proc. Natl. Acad. Sci. U.S.A* 96, 16031608 (1999).
37. Staal, F. J. et al. Wnt target genes identified by DNA microarrays in immature CD34+ thymocytes regulate proliferation and cell adhesion *J. Immunol.* 172, 10991108 (2004).
38. Burton, E. C. & Prados, M. D. Malignant gliomas *Curr. Treat Options. Oncol.* 1, 459-468 (2000).
39. Ohgaki, H. & Kleihues, P. Epidemiology and etiology of gliomas *Acta Neuropathol. (Berl)* 109, 93-108 (2005).
40. Valente, P. et al. TIMP-2 over-expression reduces invasion and angiogenesis and protects B16F10 melanoma cells from apoptosis. *Int. J. Cancer* 75, 246-253 (1998).
41. Zuliani, C. et al. Control of neuronal branching by the death receptor CD95 (Fas/Apo-1). *Cell Death. Differ.* 13, 31-40 (2006).
42. Demjen, D. et al. Neutralization of CD95 ligand promotes regeneration and functional recovery after spinal cord injury. *Nat. Med.* 10, 389-395 (2004).
43. Martin-Villalba, A. et al. CD95 ligand (Fas-L/APO-1L) and tumor necrosis factor-related apoptosis-inducing ligand mediate ischemia-induced apoptosis in neurons. *J Neurosci* 19, 3809-17 (1999).
44. Martin-Villalba, A. et al. Therapeutic neutralization of CD95L and TNF attenuates brain damage in stroke. *Cell Death and Differentiation* 8, 679-686 (2001).
45. Mattson, M. P. Apoptosis in neurodegenerative disorders *Nat. Rev. Mol. Cell Biol.* 1, 120-129 (2000).
46. Trauth, B. C. et al. Monoclonal antibody-mediated tumor regression by induction of apoptosis. *Science* 245, 301-5 (1989).
47. Scaffidi, C., Medema, J. P., Krammer, P. H., & Peter, M. E. FLICE is predominantly expressed as two functionally active isoforms, caspase-8/a and caspase-8/b. *J Biol Chem* 272, 26953-8 (1997).
48. Ninck, S. et al. Expression profiles of angiogenic growth factors in squamous cell carcinomas of the head and neck *Int. J. Cancer* 106, 34-44 (2003).
49. Del Duca, D., Werbowetski, T., & Del Maestro, R. F. Spheroid preparation from hanging drops: characterization of a model of brain tumor invasion *J. Neurooncol.* 67, 295-303 (2004).
50. Boggon, T. J. and Eck, M. J. (2004). Structure and regulation of Src family kinases. Oncogene 23, 7918-7927.
51. Cha, S. S., Shin, H. C., Choi, K. Y., and Oh, B. H. (1999). Expression, purification and crystallization of recombinant human TRAIL. Acta Crystallogr D Biol Crystallogr 55, 1101-4.
52. Choi, K., Benveniste, E. N., and Choi, C. (2003). Induction of intercellular adhesion molecule-1 by Fas ligation: proinflammatory roles of Fas in human as troglioma cells. Neurosci. Lett. 352, 21-24.
53. Cursi, S., Rufini, A., Stagni, V., Condo, I., Matafora, V., Bachi, A., Bon ifazi, A. P., Coppola, L., Superti-Furga, G., Testi, R., and Barila, D. (2006). Src kinase phosphorylates Caspase-8 on Tyr380: a novel mechanism of apop tosis suppression. EMBO J. 25, 1895-1905.
54. Daigle, I., Yousefi, S., Colonna, M., Green, D. R., and Simon, H. U. (2002). Death receptors bind SHP-1 and block cytokine-induced anti-apoptotic sig naling in neutrophils. Nat. Med. 8, 61-67.
55. Eck, M. J. and Sprang, S. R. (1989). The structure of tumor necrosis factor-alpha at 2.6 A resolution. Implications for receptor binding. J Biol Chem 264, 17595-605.
56. Eischen, C. M., Dick, C. J., and Leibson, P. J. (1994). Tyrosine kinase activa tion provides an early and requisite signal for Fas-induced apoptosis. J Im munol 153, 1947-54.
57. Fan, X., Aalto, Y., Sanko, S. G., Knuutila, S., Klatzmann, D., and Castresana, J. S. (2002). Genetic profile, PTEN mutation and therapeutic role of PTEN in glioblastomas. Int. J. Oncol. 21, 1141-1150.
58. Feig, C., Tchikov, V., Schutze, S., and Peter, M. E. (2007). Palmitoylation of CD95 facilitates formation of SDS-stable receptor aggregates that initiate apop tosis signaling. EMBO J. 26, 221-231.
59. Furnari, F. B., Lin, H., Huang, H. S., and Cavenee, W. K. (1997). Growth suppression of glioma cells by PTEN requires a functional phosphatase catalytic domain. Proc. Natl. Acad. Sci. U.S.A 94, 12479-12484.
60. Gulbins, E., Hermisson, M., Brenner, B., Grassme, H. U., Linderkamp, O., Dichgans, J., Weller, M., and Lang, F. (1998). Cellular stimulation via CD95 involves activation of phospho-inositide-3-kinase. Pflugers Arch. 435, 546-554.
61. Guthe, S., Kapinos, L., Moglich, A., Meier, S., Grzesiek, S., and Kiefha ber, T. (2004). Very fast folding and association of a trimerization domain from bacteriophage T4 fibritin. J. Mol. Biol. 337, 905-915.
62. Hymowitz, S. G., Christinger, H. W., Fuh, G., Ultsch, M., O'Connell, M., Kelley, R. F., Ashkenazi, A., and de Vos, A. M. (1999). Triggering cell death: the crystal structure of Apo2L/TRAIL in a complex with death receptor 5 [In Pro cess Citation]. Mol Cell 4, 563-71.
63. Kugler, W., Erdlenbruch, B., Junemann, A., Heinemann, D., Eibl, H., and Lakomek, M. (2002). Erucylphosphocholine-induced apoptosis in glioma cells: involvement of death receptor signalling and caspase activation. J. Neurochem. 82, 1160-1170.
64. Madrid, L. V., Wang, C. Y., Guttridge, D. C., Schottelius, A. J., Baldwin, A. S., Jr., and Mayo, M. W. (2000). Akt suppresses apoptosis by stimulating the trans activation potential of the RelA/p65 subunit of NF-kappaB. Mol. Cell Biol. 20, 1626-1638.
65. Meier, S., Guthe, S., Kiefhaber, T., and Grzesiek, S. (2004). Foldon, the natural trimerization domain of T4 fibritin, dissociates into a monomeric A-state form containing a stable beta-hairpin: atomic details of trimer dissocation and ocal betahairpin stability from residual dipolar couplings 1. J. Mol. Biol. 344, 1051-1069.
66. Ozes, O. N., Mayo, L. D., Gustin, J. A., Pfeffer, S. R., Pfeffer, L. M., and Don ner, D. B. (1999). NF-kappaB activation by tumour necrosis factor requires the Akt serine-threonine kinase. Nature 401, 82-85.
67. Park, C. M., Park, M. J., Kwak, H. J., Lee, H. C., Kim, M. S., Lee, S. H., Park, I. C., Rhee, C. H., and Hong, S. I. (2006). Ionizing Radiation Enhances Matrix Metalloproteinase-2 Secretion and Invasion of Glioma Cells through Src/Epidermal Growth Factor Receptor-Mediated p38/Akt and Phos phatidylinositol 3-Kinase/Akt Signaling Pathways. Cancer Res. 66, 8511-8519.
68. Patt, S. and Cervos-Navarro, J. (1992). Combined erbB gene overexpres sion and decreased H-ras gene expression in human gliomas. Acta Histo chem. Suppl 42, 131-138.
69. Schlottmann, K. E., Gulbins, E., Lau, S. M., and Coggeshall, K. M. (1996). Activation of Srcfamily tyrosine kinases during Fas-induced apoptosis. J. Leukoc. Biol. 60, 546-554.
70. Thomas, S. M. and Brugge, J. S. (1997). Cellular functions regulated by Src family kinases 1. Annu. Rev. Cell Dev. Biol. 13, 513-609.
71. Wong, B. R., Besser, D., Kim, N., Arron, J. R., Vologodskaia, M., Hanafusa, H., and Choi, Y. (1999). TRANCE, a TNF family member, activates Akt/PKB through a signalling complex involving TRAF6 and c-Src. Mol. Cell 4, 1041-1049.
72. Karmakar, S., Weinberg, M. S., Banik, N. L., Patel, S. J., and Ray, S. K. (2006). Activation of multiple molecular mechanisms for apoptosis in human malignant glioblastoma T98G and U87MG cells treated with sulforaphane. Neuroscience 141, 1265-1280.

What is claimed is:

1. A method for treating an individual with high grade glioma, comprising administering an agent that neutralizes CD95 activity to an individual with high grade glioma, wherein said agent is a CD95 ligand (CD95L) inhibitor comprising
a fusion protein comprising the extracellular domain of CD95 and a human Fc domain.

2. The method of claim 1, wherein the fusion protein is a fusion protein of the extracellular domain of the human CD95 with human IgG1-Fc (APG101).

3. The method of claim 1, wherein the high grade glioma is a WHO Grade III or IV glioma.

4. The method of claim 1, wherein the high grade glioma is a WHO Grade IV glioma.

5. The method of claim 1, wherein an interaction between CD95 and the protein p85 of PI3K is inhibited.

6. The method according to of claim 1, wherein said agent is administered in an amount sufficient to reduce glial cell migration and/or invasion.

* * * * *

SEQUENCE LISTING

```
<160> NUMBER OF SEQ ID NOS: 26

<210> SEQ ID NO 1
<211> LENGTH: 400
<212> TYPE: PRT
<213> ORGANISM: Homo sapiens
<220> FEATURE:
<221> NAME/KEY: SIGNAL
<222> LOCATION: (1)..(16)
<220> FEATURE:
<221> NAME/KEY: DOMAIN
<222> LOCATION: (17)..(172)
<223> OTHER INFORMATION: CD95R-ECD
<220> FEATURE:
<221> NAME/KEY: DOMAIN
<222> LOCATION: (173)..(400)
<223> OTHER INFORMATION: IgG1-Fc

<400> SEQUENCE: 1
```

```
Met Val Gly Ile Trp Thr Leu Leu Pro Leu Val Leu Thr Ser Val Ala
1               5                   10                  15

Arg Leu Ser Ser Lys Ser Val Asn Ala Gln Val Thr Asp Ile Asn Ser
            20                  25                  30

Lys Gly Leu Glu Leu Arg Lys Thr Val Thr Val Glu Thr Gln Asn
            35                  40                  45

Leu Glu Gly Leu His His Asp Gly Gln Phe Cys His Lys Pro Cys Pro
50                  55                  60

Pro Gly Glu Arg Lys Ala Arg Asp Cys Thr Val Asn Gly Asp Glu Pro
65                  70                  75                  80

Asp Cys Val Pro Cys Gln Glu Gly Lys Glu Tyr Thr Asp Lys Ala His
                85                  90                  95

Phe Ser Ser Lys Cys Arg Arg Cys Arg Leu Cys Asp Glu Gly His Gly
            100                 105                 110

Leu Glu Val Glu Ile Asn Cys Thr Arg Thr Gln Asn Thr Lys Cys Arg
            115                 120                 125

Cys Lys Pro Asn Phe Phe Cys Asn Ser Thr Val Cys Glu His Cys Asp
    130                 135                 140

Pro Cys Thr Lys Cys Glu His Gly Ile Ile Lys Glu Cys Thr Leu Thr
145                 150                 155                 160

Ser Asn Thr Lys Cys Lys Glu Glu Gly Ser Arg Ser Cys Asp Lys Thr
                165                 170                 175

His Thr Cys Pro Pro Cys Pro Ala Pro Glu Leu Leu Gly Gly Pro Ser
            180                 185                 190

Val Phe Leu Phe Pro Pro Lys Pro Lys Asp Thr Leu Met Ile Ser Arg
            195                 200                 205

Thr Pro Glu Val Thr Cys Val Val Val Asp Val Ser His Glu Asp Pro
210                 215                 220

Glu Val Lys Phe Asn Trp Tyr Val Asp Gly Val Glu Val His Asn Ala
225                 230                 235                 240

Lys Thr Lys Pro Arg Glu Glu Gln Tyr Asn Ser Thr Tyr Arg Val Val
                245                 250                 255

Ser Val Leu Thr Val Leu His Gln Asp Trp Leu Asn Gly Lys Glu Tyr
            260                 265                 270

Lys Cys Lys Val Ser Asn Lys Ala Leu Pro Ala Pro Ile Glu Lys Thr
            275                 280                 285

Ile Ser Lys Ala Lys Gly Gln Pro Arg Glu Pro Gln Val Tyr Thr Leu
    290                 295                 300

Pro Pro Ser Arg Glu Glu Met Thr Lys Asn Gln Val Ser Leu Thr Cys
305                 310                 315                 320

Leu Val Lys Gly Phe Tyr Pro Ser Asp Ile Ala Val Glu Trp Glu Ser
                325                 330                 335

Asn Gly Gln Pro Glu Asn Asn Tyr Lys Thr Thr Pro Pro Val Leu Asp
            340                 345                 350

Ser Asp Gly Ser Phe Phe Leu Tyr Ser Lys Leu Thr Val Asp Lys Ser
            355                 360                 365

Arg Trp Gln Gln Gly Asn Val Phe Ser Cys Ser Val Met His Glu Ala
370                 375                 380

Leu His Asn His Tyr Thr Gln Lys Ser Leu Ser Leu Ser Pro Gly Lys
385                 390                 395                 400

<210> SEQ ID NO 2
<211> LENGTH: 21
```

```
<212> TYPE: DNA
<213> ORGANISM: Artificial Sequence
<220> FEATURE:
<223> OTHER INFORMATION: Primer (CD95 forw)

<400> SEQUENCE: 2
actgtgaccc ttgcaccaaa t                                              21

<210> SEQ ID NO 3
<211> LENGTH: 21
<212> TYPE: DNA
<213> ORGANISM: Artificial Sequence
<220> FEATURE:
<223> OTHER INFORMATION: Primer (CD95 rev)

<400> SEQUENCE: 3
gccaccccaa gttagatctg g                                              21

<210> SEQ ID NO 4
<211> LENGTH: 29
<212> TYPE: DNA
<213> ORGANISM: Artificial Sequence
<220> FEATURE:
<223> OTHER INFORMATION: Primer (CD95 probe)

<400> SEQUENCE: 4
aatcatcaag gaatgcacac tcaccagca                                      29

<210> SEQ ID NO 5
<211> LENGTH: 21
<212> TYPE: DNA
<213> ORGANISM: Artificial Sequence
<220> FEATURE:
<223> OTHER INFORMATION: Primer (CD95L-forw)

<400> SEQUENCE: 5
aaagtggccc atttaacagg c                                              21

<210> SEQ ID NO 6
<211> LENGTH: 23
<212> TYPE: DNA
<213> ORGANISM: Artificial Sequence
<220> FEATURE:
<223> OTHER INFORMATION: Primer (CD95L-rev)

<400> SEQUENCE: 6
aaagcaggac aattccatag gtg                                            23

<210> SEQ ID NO 7
<211> LENGTH: 25
<212> TYPE: DNA
<213> ORGANISM: Artificial Sequence
<220> FEATURE:
<223> OTHER INFORMATION: Primer (CD95L-probe)

<400> SEQUENCE: 7
tccaactcaa ggtccatgcc tctgg                                          25

<210> SEQ ID NO 8
<211> LENGTH: 25
<212> TYPE: DNA
<213> ORGANISM: Artificial Sequence
<220> FEATURE:
<223> OTHER INFORMATION: Primer (MMP-9 forw)

<400> SEQUENCE: 8
```

```
gatccaaaac tactcggaag acttg                                          25

<210> SEQ ID NO 9
<211> LENGTH: 15
<212> TYPE: DNA
<213> ORGANISM: Artificial Sequence
<220> FEATURE:
<223> OTHER INFORMATION: Primer (MMP-9 rev)

<400> SEQUENCE: 9
gaaggcgcgg gcaaa                                                     15

<210> SEQ ID NO 10
<211> LENGTH: 20
<212> TYPE: DNA
<213> ORGANISM: Artificial Sequence
<220> FEATURE:
<223> OTHER INFORMATION: Primer (MMP-9 probe)

<400> SEQUENCE: 10
cgcgggcggt gattgacgac                                                20

<210> SEQ ID NO 11
<211> LENGTH: 26
<212> TYPE: DNA
<213> ORGANISM: Artificial Sequence
<220> FEATURE:
<223> OTHER INFORMATION: Primer (MMP-2 forw)

<400> SEQUENCE: 11
ggacacacta aagaagatgc agaagt                                         26

<210> SEQ ID NO 12
<211> LENGTH: 21
<212> TYPE: DNA
<213> ORGANISM: Artificial Sequence
<220> FEATURE:
<223> OTHER INFORMATION: Primer (MMP-2 rev)

<400> SEQUENCE: 12
cgcatggtct cgatggtatt c                                              21

<210> SEQ ID NO 13
<211> LENGTH: 26
<212> TYPE: DNA
<213> ORGANISM: Artificial Sequence
<220> FEATURE:
<223> OTHER INFORMATION: Primer (MMP-2 probe)

<400> SEQUENCE: 13
agtgccccag caaggtgatc ttgacc                                         26

<210> SEQ ID NO 14
<211> LENGTH: 23
<212> TYPE: DNA
<213> ORGANISM: Artificial Sequence
<220> FEATURE:
<223> OTHER INFORMATION: Primer (b-actin forw)

<400> SEQUENCE: 14
acccacactg tgcccatcta cga                                            23

<210> SEQ ID NO 15
<211> LENGTH: 25
<212> TYPE: DNA
<213> ORGANISM: Artificial Sequence
```

-continued

```
<220> FEATURE:
<223> OTHER INFORMATION: Primer (b-actin rev)

<400> SEQUENCE: 15
cagcggaacc gctcattgcc aatgg                                         25

<210> SEQ ID NO 16
<211> LENGTH: 26
<212> TYPE: DNA
<213> ORGANISM: Artificial Sequence
<220> FEATURE:
<223> OTHER INFORMATION: Primer (b-actin probe)

<400> SEQUENCE: 16
atgccctccc ccatgccatc ctgcgt                                        26

<210> SEQ ID NO 17
<211> LENGTH: 19
<212> TYPE: DNA
<213> ORGANISM: Artificial Sequence
<220> FEATURE:
<223> OTHER INFORMATION: Primer (Yes forw)

<400> SEQUENCE: 17
tatggctgcc agattgctg                                                19

<210> SEQ ID NO 18
<211> LENGTH: 20
<212> TYPE: DNA
<213> ORGANISM: Artificial Sequence
<220> FEATURE:
<223> OTHER INFORMATION: Primer (Yes rev)

<400> SEQUENCE: 18
ttcaggagct gtccatttga                                               20

<210> SEQ ID NO 19
<211> LENGTH: 20
<212> TYPE: DNA
<213> ORGANISM: Artificial Sequence
<220> FEATURE:
<223> OTHER INFORMATION: Primer (Fyn forw)

<400> SEQUENCE: 19
tgaacagctc ggaaggagat                                               20

<210> SEQ ID NO 20
<211> LENGTH: 20
<212> TYPE: DNA
<213> ORGANISM: Artificial Sequence
<220> FEATURE:
<223> OTHER INFORMATION: Primer (Fyn rev)

<400> SEQUENCE: 20
ggtttcactc tccgcgataa                                               20

<210> SEQ ID NO 21
<211> LENGTH: 24
<212> TYPE: DNA
<213> ORGANISM: Artificial Sequence
<220> FEATURE:
<223> OTHER INFORMATION: Primer (GAPDH forw)

<400> SEQUENCE: 21
ggtcggagtc aacggatttg gtcg                                          24
```

-continued

<210> SEQ ID NO 22
<211> LENGTH: 22
<212> TYPE: DNA
<213> ORGANISM: Artificial Sequence
<220> FEATURE:
<223> OTHER INFORMATION: Primer (GAPDH rev)

<400> SEQUENCE: 22
cctccgacgc ctgcttcacc ac                                              22

<210> SEQ ID NO 23
<211> LENGTH: 11
<212> TYPE: PRT
<213> ORGANISM: Artificial Sequence
<220> FEATURE:
<223> OTHER INFORMATION: Synthetic linker

<400> SEQUENCE: 23

Gly Ser Ser Gly Ser Ser Gly Ser Ser Gly Ser
1               5                   10

<210> SEQ ID NO 24
<211> LENGTH: 16
<212> TYPE: PRT
<213> ORGANISM: Artificial Sequence
<220> FEATURE:
<223> OTHER INFORMATION: Hexahistidine Tag and a Streptag-II

<400> SEQUENCE: 24

His His His His His His Ser Ala Trp Ser His Pro Gln Phe Glu Lys
1               5                   10                  15

<210> SEQ ID NO 25
<211> LENGTH: 8
<212> TYPE: PRT
<213> ORGANISM: Artificial Sequence
<220> FEATURE:
<223> OTHER INFORMATION: Synthetic Linker

<400> SEQUENCE: 25

Ser Gly Pro Ser Ser Ser Ser Ser
1               5

<210> SEQ ID NO 26
<211> LENGTH: 222
<212> TYPE: PRT
<213> ORGANISM: Homo sapiens

<400> SEQUENCE: 26

Met Glu Thr Asp Thr Leu Leu Leu Trp Val Leu Leu Leu Trp Val Pro
1               5                   10                  15

Gly Ser Thr Gly Glu Leu Arg Lys Val Ala His Leu Thr Gly Lys Ser
            20                  25                  30

Asn Ser Arg Ser Met Pro Leu Glu Trp Glu Asp Thr Tyr Gly Ile Val
        35                  40                  45

Leu Leu Ser Gly Val Lys Tyr Lys Lys Gly Gly Leu Val Ile Asn Glu
    50                  55                  60

Thr Gly Leu Tyr Phe Val Tyr Ser Lys Val Tyr Phe Arg Gly Gln Ser
65                  70                  75                  80

Cys Asn Asn Leu Pro Leu Ser His Lys Val Tyr Met Arg Asn Ser Lys
                85                  90                  95

Tyr Pro Gln Asp Leu Val Met Met Glu Gly Lys Met Met Ser Tyr Cys
            100                 105                 110

```
Thr Thr Gly Gln Met Trp Ala Arg Ser Ser Tyr Leu Gly Ala Val Glu
        115             120             125

Asn Leu Thr Ser Ala Asp His Leu Tyr Val Asn Val Ser Glu Leu Ser
    130             135             140

Leu Val Asn Phe Glu Glu Ser Gln Thr Phe Phe Gly Leu Tyr Lys Leu
145             150             155             160

Gly Ser Ser Gly Ser Ser Gly Ser Ser Gly Ser Gly Tyr Ile Pro Glu
            165             170             175

Ala Pro Arg Asp Gly Gln Ala Tyr Val Arg Lys Asp Gly Glu Trp Val
            180             185             190

Leu Leu Ser Thr Phe Leu Ser Gly Pro Ser Ser Ser Ser His His
        195             200             205

His His His His Ser Ala Trp Ser His Pro Gln Phe Glu Lys
    210             215             220
```